(12) United States Patent
Rousselle et al.

(10) Patent No.: US 8,431,686 B2
(45) Date of Patent: Apr. 30, 2013

(54) MONOCLONAL ANTIBODIES DIRECTED AGAINST LG4-5 DOMAIN OF ALPHA3 CHAIN OF HUMAN LAMININ-5

(75) Inventors: Patricia Rousselle, Lyon (FR); Francois Letourneur, Sainte Foy les Lyon (FR)

(73) Assignees: Centre National de la Recherche Scientifique (CNRS), Paris (FR); Universite Claude Bernard Lyon I, Villeurbanne (FR)

( * ) Notice: Subject to any disclaimer, the term of this patent is extended or adjusted under 35 U.S.C. 154(b) by 0 days.

(21) Appl. No.: 13/140,579

(22) PCT Filed: Dec. 18, 2009

(86) PCT No.: PCT/EP2009/067597
§ 371 (c)(1),
(2), (4) Date: Oct. 5, 2011

(87) PCT Pub. No.: WO2010/070134
PCT Pub. Date: Jun. 24, 2010

(65) Prior Publication Data
US 2012/0034229 A1     Feb. 9, 2012

(30) Foreign Application Priority Data
Dec. 18, 2008   (EP) .................................... 08305975

(51) Int. Cl.
*C07K 16/00*    (2006.01)
(52) U.S. Cl.
USPC .................. 530/387.1; 530/387.3; 530/388.1; 530/388.25
(58) Field of Classification Search ........................ None
See application file for complete search history.

(56) References Cited

U.S. PATENT DOCUMENTS

| 7,323,551 | B2 | 1/2008 | Marinkovich | |
| 7,875,277 | B2 * | 1/2011 | Marinkovich | ............. 424/130.1 |

FOREIGN PATENT DOCUMENTS

| EP | 2 198 884 A1 | 6/2010 |
| WO | WO 00/26342 A1 | 5/2000 |
| WO | WO 2005/040219 A1 | 5/2005 |
| WO | WO 2005/052003 A2 | 6/2005 |
| WO | WO 2005/056598 A2 | 6/2005 |
| WO | WO 2005/073254 A2 | 8/2005 |
| WO | WO 2008/005828 A2 | 1/2008 |

OTHER PUBLICATIONS

Sigle et al. Globular domains 4/5 of the laminin α3 chain mediate deposition of precursor laminin 5. J. Cell Sci. 117, 4481-4494.*
International Search Report issued in application No. PCT/EP2009/067597 on Mar. 2, 2010.
Okamoto et al., "Normal Human Keratinocytes Bind to the αLG4/5 Domain of Unprocessed Laminin-5 through the Receptor Syndecan-1," The Journal of Biological Chemistry, vol. 278, No. 45, pp. 44168-44177, 2003.
Tsubota et al., "Regulation of Biological Activity and Matrix Assembly of Laminin-5 by COOH-terminal, LG4-5 Domain of α3 Chain," The Journal of Biological Chemistry, vol. 280, No. 15, pp. 14370-14377, 2005.
Sulka et al., "Tyrosine Dephosphorylation of the Syndecan-1 PDZ Binding Domain Regulates Syntenin-1 Recruitment," The Journal of Biological Chemistry, vol. 284, No. 16, pp. 16059-10671, Apr. 17, 2009.
Tran et al., "Targeting a Tumor-Specific Laminin Domain Critical for Human Carcinogenesis," Cancer Research, vol. 68, No. 8, pp. 2885-2894, Apr. 15, 2008.
Ogawa et al., "The Short Arm of Laminin γ2 Chain of Laminin-5 (Laminin-332) Binds Syndecan-1 and Regulates Cellular Adhesion and Migration by Suppressing Phosphoryation of Integrin β4 Chain," Molecular Biology of the Cell, vol. 18, pp. 1621-1633, May 2007.
Carpenter et al., "Motility Induction in Breast Cancer Carcinoma by Mammary Epithelial Laminin 332 (Laminin 5)," Molecular Cancer Research, vol. 7, No. 4, pp. 462-475, Apr. 2009.
Bachy et al., "Syndecan-1 Interaction With the LG4/5 Domain in Laminin-332 is Essential for Keratinocyte Migration," Journal of Cellular Physiology, vol. 214, pp. 238-249, 2008.
Baker et al., "Laminin-5 and hemidesmosomes: role of the α3 chain subunit in hemidesmosome stability and assembly," J Cell Sci, 1996, pp. 2509-2520, vol. 109.
Carter et al., "Epiligrin, a New Cell Adhesion Ligand for Integrin α3β1 in Epithelial Basement Membranes," Cell, May 1991, pp. 599-610, vol. 65.
Champliaud et al., Human Amnion Contains a Novel Laminin Variant, Laminin 7, Which Like Laminin 6 Covalently Associates with Laminin 5 to Promote Stable Epithelial-Stromal Attachment, J. Cell Biol, Mar. 1996, pp. 1189-1198, vol. 132, No. 6.
Chen et al., "NC1 Domain of Type VII Collagen Binds to the β3 Chain of Laminin 5 Via a Unique Subdomain Within the Fbronectin-Like Repeats," J. Invest. Dermatol., Feb. 1999, 177-183, vol. 112, No. 2.
Decline et al., "Keratinocyte migration requires α2β1 integrin-mediated interaction with the laminin 5 γ2 chain," J. Cell Sci. 2001, 811-823, vol. 114, No. 4.
Frank et al., "Laminin 5 deposition regulates keratinocyte polarization and persistent migration," J Cell Sci. 2004, 1351-1363, vol. 117, No. 8.
Franzke et al., "C-terminal Truncation Impairs Glycosylation of Transmembrane Collagen XVII and Leads to Intracellular Accumulation," J. Biol. Chem., Oct. 2006, pp. 30260-30268, vol. 281, No. 40.
Goldfinger et al., "The α3 laminin subunit, α6β4 and α3β1 integrin coordinately regulate wound healing in cultured epithelial cells and in the skin," J Cell Sci., 1999, pp. 2615-2629, vol. 112.

(Continued)

*Primary Examiner* — Maher Haddad
(74) *Attorney, Agent, or Firm* — Foley & Lardner LLP

(57) ABSTRACT

The present invention relates to a monoclonal antibody binding to the LG4/5 domain of chain alpha3 of human protein laminin-5, wherein said monoclonal antibody inhibits the binding of syndecan-1 to said laminin-5 alpha3 chain LG4/5 domain, in particular 1H12 monoclonal antibody produced by the hybridoma cell line named 1H12 deposited on Jan. 8, 2008 at the C. N. C. M. under number I-3890, as well as chimerized, humanized derivatives and fragments thereof, and nucleic acid sequences encoding them, as well as vectors and host cells expressing them. The invention further relates to the medical application of such antibodies, in particular for treating cancer.

8 Claims, 23 Drawing Sheets

OTHER PUBLICATIONS

Gonzales et al., "A Cell Signal Pathway Involving Laminin-5, α3β1 Integrin, and Mitogen-activated Protein Kinase Can Regulate Epithelial Cell Proliferation," Mol. Biol. Cell, Feb. 1999, pp. 259-270, vol. 10.

Hintermann et al., "Epithelial cell motility on laminin-5: regulation by matrix assembly, proteolysis, integrins and erbB receptors," Matrix Biol., 2004, pp. 75-85, vol. 23.

Kim et al., "Epithelial Cell-Specific Laminin 5 Is Required for Survival of Early Thymocytes," J. Immunol., 2000, 192-201, vol. 165.

Lohi J., "Laminin-5 in the progression of carcinomas," Int. J. Cancer, 2001, pp. 763-767, vol. 94.

Miyazaki K., "Laminin-5 (laminin-332): Unique biological activity and role in tumor growth and invasion," Cancer Sci, Feb. 2006, pp. 91-98, vol. 97, No. 2.

Mizushima et al., "Identification of Integrin-dependent and -independent Cell Adhesion Domains in COOH-Terminal Globular Region of Laminin-5 α3 Chain," Cell Growth Differ, Sep. 1997, pp. 979-987, vol. 8.

Orlandi et al., "Cloning immunoglobulin variable domains for expression by the polymerase chain reaction (chimeric antibodies/MBr1)," Proc. Natl. Acad. Sci. USA, May 1989, pp. 3833-3837, vol. 86.

Paine-Murrieta et al., "Human tumor models in the severe combined immune deficient (scid) mouse," Cancer Chemother. Pharmacol., 1997, pp. 209-214, vol. 40.

Pyke et al., "Laminin-5 Is a Marker of Invading Cancer Cells in Some Human Carcinomas and Is Coexpressed with the Receptor for Urokinase Plasminogen Activator in Budding Cancer Cells in Colon Adenocarcinomas," Cancer Res., Sep. 1995, pp. 4132-4139, vol. 55.

Remy et al., "Matrilysin 1 Influences Colon Carcinoma Cell Migration by Cleavage of the Laminin-5 β3 Chain," Cancer Res., Dec. 2006, pp. 11228-11237, vol. 66, No. 23.

Rousselle et al., "Kalinin Is More Efficient than Laminin in Promoting Adhesion of Primary Keratinocytes and Some Other Epithelial Cells and Has a Different Requirement for Integrin Receptors," J. Cell Biol., Apr. 1994, pp. 205-214, vol. 125, No. 1.

Rousselle et al., "Kalinin: an Epithelium-Specific Basement Membrane Adhesion Molecule That Is a Component of Anchoring Filaments," J. Cell Biol., Aug. 1991, pp. 567-576, vol. 114, No. 3.

Rousselle et al., "Laminin 5 Binds the NC-1 Domain of Type VII Collagen," J Cell Biol, Aug. 1997, pp. 719-728, vol. 138, No. 3.

Ryan et al., "Cloning of the LamA3 Gene Encoding the α3 Chain of the Adhesive Ligand Epiligrin: Expression in Wound Repair," J Biol Chem, Sep. 1994, pp. 22779-22787, vol. 269, No. 36.

Ryan et al., "Targeted Disruption of the *LAMA3* Gene in Mice Reveals Abnormalities in Survival and Late Stage Differentiation of Epithelial Cells," J Cell Biol, Jun. 1999, pp. 1309-1323, vol. 145. No. 6.

Sasaki et al., "Short Arm Region of Laminin-5 γ2 Chain: Structure, Mechanism of Processing and Binding to Heparin and Proteins," J Mol Biol, 2001, pp. 751-763, vol. 314.

Shang et al., "The LG3 Module of Laminin-5 Harbors a Binding Site for Integrin $\alpha_3\beta_1$ That Promotes Cell Adhesion, Spreading and Migration," J. Biol. Chem., Aug. 2001, pp. 33045-33053, vol. 276, No. 35.

Sordat et al., "Differential Expression of Laminin-5 Subunits and Integrin Receptors in Human Colorectal Neoplasia," J. Pathol., 1998, pp. 44-52, vol. 185.

Tsuruta et al., "Laminin-332-integrin interaction: a target for cancer therapy?," Curr. Med. Chem., 2008, pp. 1968-1975, vol. 15, No. 16.

Tunggal et al., "Defective laminin 5 processing in cylindroma cells," Am. J. Pathol., Feb. 2002, pp. 459-468, vol. 160, No. 2.

Utani et al., "A Unique Sequence of the Laminin α3 G Domain Binds to Heparin and Promotes Cell Adhesion through Syndecan-2 and -4," J. Biol. Chem., Aug. 2001, pp. 28779-28788, vol. 276, No. 31.

Wayner et al., "Epiligrin, A Component of Epithelial Basement Membranes, Is an Adhesive Ligand for α3β1 Positive T Lymphocytes," J. Cell Biol., Jun. 1993, pp. 1141-1152, vol. 121, No. 5.

Xia et al., "Anchorage Mediated by Integrin α6β4 to Laminin 5 (Epiligrin) Regulates Tyrosine Phosphorylation of a Membrane-associated 80-kD Protein," J. Cell Biol., Feb. 1996, pp. 727-740, vol. 132, No. 4.

\* cited by examiner

A
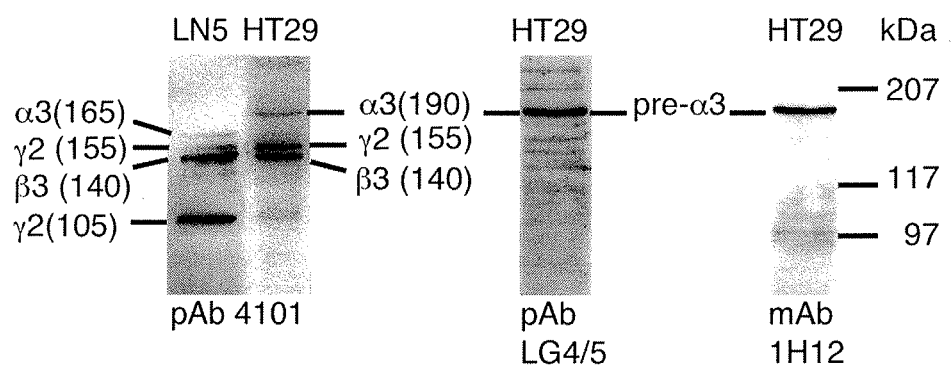
B
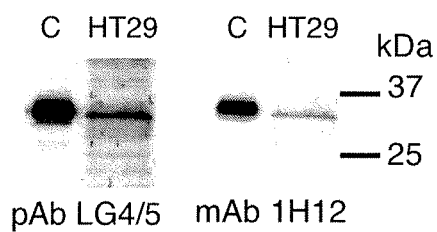
Figure 7

Figure 10: Organisation of the 1H12-VH domain.

Figure 11. Organisation of the 1H12-VL domain.

Figure 14. Organisation of the 3A11-VH domain. The cDNA sequence encoding the VH domain of the 3A11 hybridoma was analyzed (http://imgt.cines.fr/) to determine the position of FR and CDR regions.

Figure 15. Organisation of the 3A11-VL domain. The cDNA sequence encoding the VL domain of the 3A11 hybridoma was analyzed (http://imgt.cines.fr/) to determine the position of FR and CDR regions.

Figure 16. Organisation of the 15G5-VH domain. The cDNA sequence encoding the VH domain of the 15G5 hybridoma was analyzed (http://imgt.cines.fr/) to determine the position of FR and CDR regions.

Figure 17. Organisation of the 15G5-VL domain. The cDNA sequence encoding the VL domain of the 15G5 hybridoma was analyzed (http://imgt.cines.fr/) to determine the position of FR and CDR regions.

SEQUENCE LISTING

<160> NUMBER OF SEQ ID NOS: 40

<210> SEQ ID NO 1
<211> LENGTH: 1713
<212> TYPE: PRT

<213> ORGANISM: homo sapiens

<400> SEQUENCE: 1

```
Met Gly Trp Leu Trp Ile Phe Gly Ala Ala Leu Gly Gln Cys Leu Gly
 1               5                  10                  15

Tyr Ser Ser Gln Gln Arg Val Pro Phe Leu Gln Pro Pro Gly Gln
            20                  25                  30

Ser Gln Leu Gln Ala Ser Tyr Val Glu Phe Arg Pro Ser Gln Gly Cys
            35                  40                  45

Ser Pro Gly Tyr Tyr Arg Asp His Lys Gly Leu Tyr Thr Gly Arg Cys
        50                  55                  60

Val Pro Cys Asn Cys Asn Gly His Ser Asn Gln Cys Gln Asp Gly Ser
 65                  70                  75                  80

Gly Ile Cys Val Asn Cys Gln His Asn Thr Ala Gly Glu His Cys Glu
                85                  90                  95

Arg Cys Gln Glu Gly Tyr Tyr Gly Asn Ala Val His Gly Ser Cys Arg
            100                 105                 110

Ala Cys Pro Cys Pro His Thr Asn Ser Phe Ala Thr Gly Cys Val Val
        115                 120                 125

Asn Gly Gly Asp Val Arg Cys Ser Cys Lys Ala Gly Tyr Thr Gly Thr
130                 135                 140

Gln Cys Glu Arg Cys Ala Pro Gly Tyr Phe Gly Asn Pro Gln Lys Phe
145                 150                 155                 160

Gly Gly Ser Cys Gln Pro Cys Ser Cys Asn Ser Asn Gly Gln Leu Gly
                165                 170                 175

Ser Cys His Pro Leu Thr Gly Asp Cys Ile Asn Gln Glu Pro Lys Asp
            180                 185                 190

Ser Ser Pro Ala Glu Glu Cys Asp Asp Cys Asp Ser Cys Val Met Thr
        195                 200                 205

Leu Leu Asn Asp Leu Ala Thr Met Gly Glu Gln Leu Arg Leu Val Lys
210                 215                 220

Ser Gln Leu Gln Gly Leu Ser Ala Ser Ala Gly Leu Leu Glu Gln Met
225                 230                 235                 240

Arg His Met Glu Thr Gln Ala Lys Asp Leu Arg Asn Gln Leu Leu Asn
                245                 250                 255

Tyr Arg Ser Ala Ile Ser Asn His Gly Ser Lys Ile Glu Gly Leu Glu
            260                 265                 270

Arg Glu Leu Thr Asp Leu Asn Gln Glu Phe Glu Thr Leu Gln Glu Lys
        275                 280                 285

Ala Gln Val Asn Ser Arg Lys Ala Gln Thr Leu Asn Asn Asn Val Asn
290                 295                 300

Arg Ala Thr Gln Ser Ala Lys Glu Leu Asp Val Lys Ile Lys Asn Val
305                 310                 315                 320

Ile Arg Asn Val His Ile Leu Leu Lys Gln Ile Ser Gly Thr Asp Gly
                325                 330                 335

Glu Gly Asn Asn Val Pro Ser Gly Asp Phe Ser Arg Glu Trp Ala Glu
            340                 345                 350

Ala Gln Arg Met Met Arg Glu Leu Arg Asn Arg Asn Phe Gly Lys His
        355                 360                 365

Leu Arg Glu Ala Glu Ala Asp Lys Arg Glu Ser Gln Leu Leu Leu Asn
370                 375                 380

Arg Ile Arg Thr Trp Gln Lys Thr His Gln Gly Glu Asn Asn Gly Leu
385                 390                 395                 400

Ala Asn Ser Ile Arg Asp Ser Leu Asn Glu Tyr Glu Ala Lys Leu Ser
```

```
                    405                 410                 415
Asp Leu Arg Ala Arg Leu Gln Glu Ala Ala Gln Ala Lys Gln Ala
            420                 425                 430

Asn Gly Leu Asn Gln Glu Asn Glu Arg Ala Leu Gly Ala Ile Gln Arg
        435                 440                 445

Gln Val Lys Glu Ile Asn Ser Leu Gln Ser Asp Phe Thr Lys Tyr Leu
450                 455                 460

Thr Thr Ala Asp Ser Ser Leu Leu Gln Thr Asn Ile Ala Leu Gln Leu
465                 470                 475                 480

Met Glu Lys Ser Gln Lys Glu Tyr Glu Lys Leu Ala Ala Ser Leu Asn
                485                 490                 495

Glu Ala Arg Gln Glu Leu Ser Asp Lys Val Arg Glu Leu Ser Arg Ser
            500                 505                 510

Ala Gly Lys Thr Ser Leu Val Glu Glu Ala Glu Lys His Ala Arg Ser
        515                 520                 525

Leu Gln Glu Leu Ala Lys Gln Leu Glu Glu Ile Lys Arg Asn Ala Ser
530                 535                 540

Gly Asp Glu Leu Val Arg Cys Ala Val Asp Ala Ala Thr Ala Tyr Glu
545                 550                 555                 560

Asn Ile Leu Asn Ala Ile Lys Ala Ala Glu Asp Ala Ala Asn Arg Ala
                565                 570                 575

Ala Ser Ala Ser Glu Ser Ala Leu Gln Thr Val Ile Lys Glu Asp Leu
            580                 585                 590

Pro Arg Lys Ala Lys Thr Leu Ser Ser Asn Ser Asp Lys Leu Leu Asn
        595                 600                 605

Glu Ala Lys Met Thr Gln Lys Lys Leu Lys Gln Glu Val Ser Pro Ala
610                 615                 620

Leu Asn Asn Leu Gln Gln Thr Leu Asn Ile Val Thr Val Gln Lys Glu
625                 630                 635                 640

Val Ile Asp Thr Asn Leu Thr Thr Leu Arg Asp Gly Leu His Gly Ile
                645                 650                 655

Gln Arg Gly Asp Ile Asp Ala Met Ile Ser Ser Ala Lys Ser Met Val
            660                 665                 670

Arg Lys Ala Asn Asp Ile Thr Asp Glu Val Leu Asp Gly Leu Asn Pro
        675                 680                 685

Ile Gln Thr Asp Val Glu Arg Ile Lys Asp Thr Tyr Gly Arg Thr Gln
690                 695                 700

Asn Glu Asp Phe Lys Lys Ala Leu Thr Asp Ala Asp Asn Ser Val Asn
705                 710                 715                 720

Lys Leu Thr Asn Lys Leu Pro Asp Leu Trp Arg Lys Ile Glu Ser Ile
                725                 730                 735

Asn Gln Gln Leu Leu Pro Leu Gly Asn Ile Ser Asp Asn Met Asp Arg
            740                 745                 750

Ile Arg Glu Leu Ile Gln Gln Ala Arg Asp Ala Ala Ser Lys Val Ala
        755                 760                 765

Val Pro Met Arg Phe Asn Gly Lys Ser Gly Val Glu Val Arg Leu Pro
770                 775                 780

Asn Asp Leu Glu Asp Leu Lys Gly Tyr Thr Ser Leu Ser Leu Phe Leu
785                 790                 795                 800

Gln Arg Pro Asn Ser Arg Glu Asn Gly Gly Thr Glu Asn Met Phe Val
                805                 810                 815

Met Tyr Leu Gly Asn Lys Asp Ala Ser Arg Asp Tyr Ile Gly Met Ala
            820                 825                 830
```

-continued

Val Val Asp Gly Gln Leu Thr Cys Val Tyr Asn Leu Gly Asp Arg Glu
        835                 840                 845

Ala Glu Leu Gln Val Asp Gln Ile Leu Thr Lys Ser Glu Thr Lys Glu
850                 855                 860

Ala Val Met Asp Arg Val Lys Phe Gln Arg Ile Tyr Gln Phe Ala Arg
865                 870                 875                 880

Leu Asn Tyr Thr Lys Gly Ala Thr Ser Ser Lys Pro Glu Thr Pro Gly
            885                 890                 895

Val Tyr Asp Met Asp Gly Arg Asn Ser Asn Thr Leu Leu Asn Leu Asp
                900                 905                 910

Pro Glu Asn Val Val Phe Tyr Val Gly Gly Tyr Pro Pro Asp Phe Lys
            915                 920                 925

Leu Pro Ser Arg Leu Ser Phe Pro Pro Tyr Lys Gly Cys Ile Glu Leu
        930                 935                 940

Asp Asp Leu Asn Glu Asn Val Leu Ser Leu Tyr Asn Phe Lys Lys Thr
945                 950                 955                 960

Phe Asn Leu Asn Thr Thr Glu Val Glu Pro Cys Arg Arg Arg Lys Glu
                965                 970                 975

Glu Ser Asp Lys Asn Tyr Phe Glu Gly Thr Gly Tyr Ala Arg Val Pro
            980                 985                 990

Thr Gln Pro His Ala Pro Ile Pro Thr Phe Gly Gln Thr Ile Gln Thr
        995                 1000                1005

Thr Val Asp Arg Gly Leu Leu Phe Phe Ala Glu Asn Gly Asp Arg
    1010                1015                1020

Phe Ile Ser Leu Asn Ile Glu Asp Gly Lys Leu Met Val Arg Tyr
    1025                1030                1035

Lys Leu Asn Ser Glu Leu Pro Lys Glu Arg Gly Val Gly Asp Ala
    1040                1045                1050

Ile Asn Asn Gly Arg Asp His Ser Ile Gln Ile Lys Ile Gly Lys
    1055                1060                1065

Leu Gln Lys Arg Met Trp Ile Asn Val Asp Val Gln Asn Thr Ile
    1070                1075                1080

Ile Asp Gly Glu Val Phe Asp Phe Ser Thr Tyr Tyr Leu Gly Gly
    1085                1090                1095

Ile Pro Ile Ala Ile Arg Glu Arg Phe Asn Ile Ser Thr Pro Ala
    1100                1105                1110

Phe Arg Gly Cys Met Lys Asn Leu Lys Lys Thr Ser Gly Val Val
    1115                1120                1125

Arg Leu Asn Asp Thr Val Gly Val Thr Lys Lys Cys Ser Glu Asp
    1130                1135                1140

Trp Lys Leu Val Arg Ser Ala Ser Phe Ser Arg Gly Gly Gln Leu
    1145                1150                1155

Ser Phe Thr Asp Leu Gly Leu Pro Pro Thr Asp His Leu Gln Ala
    1160                1165                1170

Ser Phe Gly Phe Gln Thr Phe Gln Pro Ser Gly Ile Leu Leu Asp
    1175                1180                1185

His Gln Thr Trp Thr Arg Asn Leu Gln Val Thr Leu Glu Asp Gly
    1190                1195                1200

Tyr Ile Glu Leu Ser Thr Ser Asp Ser Gly Gly Pro Ile Phe Lys
    1205                1210                1215

Ser Pro Gln Thr Tyr Met Asp Gly Leu Leu His Tyr Val Ser Val
    1220                1225                1230

Ile Ser Asp Asn Ser Gly Leu Arg Leu Leu Ile Asp Asp Gln Leu
    1235                1240                1245

-continued

```
Leu Arg Asn Ser Lys Arg Leu Lys His Ile Ser Ser Ser Arg Gln
    1250                1255                1260

Ser Leu Arg Leu Gly Gly Ser Asn Phe Glu Gly Cys Ile Ser Asn
    1265                1270                1275

Val Phe Val Gln Arg Leu Ser Leu Ser Pro Glu Val Leu Asp Leu
    1280                1285                1290

Thr Ser Asn Ser Leu Lys Arg Asp Val Ser Leu Gly Gly Cys Ser
    1295                1300                1305

Leu Asn Lys Pro Pro Phe Leu Met Leu Leu Lys Gly Ser Thr Arg
    1310                1315                1320

Phe Asn Lys Thr Lys Thr Phe Arg Ile Asn Gln Leu Leu Gln Asp
    1325                1330                1335

Thr Pro Val Ala Ser Pro Arg Ser Val Lys Val Trp Gln Asp Ala
    1340                1345                1350

Cys Ser Pro Leu Pro Lys Thr Gln Ala Asn His Gly Ala Leu Gln
    1355                1360                1365

Phe Gly Asp Ile Pro Thr Ser His Leu Leu Phe Lys Leu Pro Gln
    1370                1375                1380

Glu Leu Leu Lys Pro Arg Ser Gln Phe Ala Val Asp Met Gln Thr
    1385                1390                1395

Thr Ser Ser Arg Gly Leu Val Phe His Thr Gly Thr Lys Asn Ser
    1400                1405                1410

Phe Met Ala Leu Tyr Leu Ser Lys Gly Arg Leu Val Phe Ala Leu
    1415                1420                1425

Gly Thr Asp Gly Lys Lys Leu Arg Ile Lys Ser Lys Glu Lys Cys
    1430                1435                1440

Asn Asp Gly Lys Trp His Thr Val Val Phe Gly His Asp Gly Glu
    1445                1450                1455

Lys Gly Arg Leu Val Val Asp Gly Leu Arg Ala Arg Glu Gly Ser
    1460                1465                1470

Leu Pro Gly Asn Ser Thr Ile Ser Ile Arg Ala Pro Val Tyr Leu
    1475                1480                1485

Gly Ser Pro Pro Ser Gly Lys Pro Lys Ser Leu Pro Thr Asn Ser
    1490                1495                1500

Phe Val Gly Cys Leu Lys Asn Phe Gln Leu Asp Ser Lys Pro Leu
    1505                1510                1515

Tyr Thr Pro Ser Ser Ser Phe Gly Val Ser Ser Cys Leu Gly Gly
    1520                1525                1530

Pro Leu Glu Lys Gly Ile Tyr Phe Ser Glu Glu Gly Gly His Val
    1535                1540                1545

Val Leu Ala His Ser Val Leu Leu Gly Pro Glu Phe Lys Leu Val
    1550                1555                1560

Phe Ser Ile Arg Pro Arg Ser Leu Thr Gly Ile Leu Ile His Ile
    1565                1570                1575

Gly Ser Gln Pro Gly Lys His Leu Cys Val Tyr Leu Glu Ala Gly
    1580                1585                1590

Lys Val Thr Ala Ser Met Asp Ser Gly Ala Gly Gly Thr Ser Thr
    1595                1600                1605

Ser Val Thr Pro Lys Gln Ser Leu Cys Asp Gly Gln Trp His Ser
    1610                1615                1620

Val Ala Val Thr Ile Lys Gln His Ile Leu His Leu Glu Leu Asp
    1625                1630                1635

Thr Asp Ser Ser Tyr Thr Ala Gly Gln Ile Pro Phe Pro Pro Ala
```

```
                      1640                1645                1650

Ser Thr Gln Glu Pro Leu His Leu Gly Gly Ala Pro Ala Asn Leu
        1655                1660                1665

Thr Thr Leu Arg Ile Pro Val Trp Lys Ser Phe Phe Gly Cys Leu
        1670                1675                1680

Arg Asn Ile His Val Asn His Ile Pro Val Pro Val Thr Glu Ala
        1685                1690                1695

Leu Glu Val Gln Gly Pro Val Ser Leu Asn Gly Cys Pro Asp Gln
        1700                1705                1710

<210> SEQ ID NO 2
<211> LENGTH: 183
<212> TYPE: PRT
<213> ORGANISM: homo sapiens

<400> SEQUENCE: 2

Met Gly Trp Leu Trp Ile Phe Gly Ala Ala Leu Gly Gln Cys Leu Gly
1               5                   10                  15

Tyr Ser Ser Gln Gln Arg Val Pro Phe Leu Gln Pro Pro Gly Gln
            20                  25                  30

Ser Gln Leu Gln Ala Ser Tyr Val Glu Phe Arg Pro Ser Lys Val Ser
        35                  40                  45

Ser Tyr Gly Gly Tyr Leu Thr Tyr Gln Ala Lys Ser Phe Ala Leu Pro
    50                  55                  60

Gly Asp Met Val Leu Leu Glu Lys Lys Pro Asp Val Gln Leu Thr Gly
65                  70                  75                  80

Gln His Met Ser Ile Ile Tyr Glu Glu Thr Asn Thr Pro Arg Pro Asp
                85                  90                  95

Arg Leu His His Gly Arg Val His Val Val Glu Gly Asn Phe Arg His
            100                 105                 110

Ala Ser Ser Arg Ala Pro Val Ser Arg Glu Glu Leu Met Thr Val Leu
        115                 120                 125

Ser Arg Leu Ala Asp Val Arg Ile Gln Gly Leu Tyr Phe Thr Glu Thr
    130                 135                 140

Gln Arg Leu Thr Leu Ser Glu Val Gly Leu Glu Glu Ala Ser Asp Thr
145                 150                 155                 160

Gly Ser Gly Arg Ile Ala Leu Ala Val Glu Ile Cys Ala Cys Pro Pro
                165                 170                 175

Ala Tyr Ala Gly Asp Ser Cys
            180

<210> SEQ ID NO 3
<211> LENGTH: 353
<212> TYPE: PRT
<213> ORGANISM: artificial
<220> FEATURE:
<223> OTHER INFORMATION: LG4-5 domain of alpha 3 chain of human
      laminin-5

<400> SEQUENCE: 3

Gln Ala Asn His Gly Ala Leu Gln Phe Gly Asp Ile Pro Thr Ser His
1               5                   10                  15

Leu Leu Phe Lys Leu Pro Gln Glu Leu Leu Lys Pro Arg Ser Gln Phe
            20                  25                  30

Ala Val Asp Met Gln Thr Thr Ser Ser Arg Gly Leu Val Phe His Thr
        35                  40                  45

Gly Thr Lys Asn Ser Phe Met Ala Leu Tyr Leu Ser Lys Gly Arg Leu
    50                  55                  60
```

```
Val Phe Ala Leu Gly Thr Asp Gly Lys Lys Leu Arg Ile Lys Ser Lys
 65                  70                  75                  80

Glu Lys Cys Asn Asp Gly Lys Trp His Thr Val Phe Gly His Asp
                 85                  90                  95

Gly Glu Lys Gly Arg Leu Val Val Asp Gly Leu Arg Ala Arg Glu Gly
             100                 105                 110

Ser Leu Pro Gly Asn Ser Thr Ile Ser Ile Arg Ala Pro Val Tyr Leu
             115                 120                 125

Gly Ser Pro Pro Ser Gly Lys Pro Lys Ser Leu Pro Thr Asn Ser Phe
         130                 135                 140

Val Gly Cys Leu Lys Asn Phe Gln Leu Asp Ser Lys Pro Leu Tyr Thr
145                 150                 155                 160

Pro Ser Ser Ser Phe Gly Val Ser Ser Cys Leu Gly Gly Pro Leu Glu
                 165                 170                 175

Lys Gly Ile Tyr Phe Ser Glu Glu Gly Gly His Val Val Leu Ala His
             180                 185                 190

Ser Val Leu Leu Gly Pro Glu Phe Lys Leu Val Phe Ser Ile Arg Pro
         195                 200                 205

Arg Ser Leu Thr Gly Ile Leu Ile His Ile Gly Ser Gln Pro Gly Lys
210                 215                 220

His Leu Cys Val Tyr Leu Glu Ala Gly Lys Val Thr Ala Ser Met Asp
225                 230                 235                 240

Ser Gly Ala Gly Gly Thr Ser Thr Ser Val Thr Pro Lys Gln Ser Leu
                 245                 250                 255

Cys Asp Gly Gln Trp His Ser Val Ala Val Thr Ile Lys Gln His Ile
             260                 265                 270

Leu His Leu Glu Leu Asp Thr Asp Ser Ser Tyr Thr Ala Gly Gln Ile
         275                 280                 285

Pro Phe Pro Pro Ala Ser Thr Gln Glu Pro Leu His Leu Gly Gly Ala
290                 295                 300

Pro Ala Asn Leu Thr Thr Leu Arg Ile Pro Val Trp Lys Ser Phe Phe
305                 310                 315                 320

Gly Cys Leu Arg Asn Ile His Val Asn His Ile Pro Val Pro Val Thr
                 325                 330                 335

Glu Ala Leu Glu Val Gln Gly Pro Val Ser Leu Asn Gly Cys Pro Asp
             340                 345                 350

Gln

<210> SEQ ID NO 4
<211> LENGTH: 11
<212> TYPE: PRT
<213> ORGANISM: artificial
<220> FEATURE:
<223> OTHER INFORMATION: CDR1 domain of Immunoglobulin light chain

<400> SEQUENCE: 4

Gln Ser Leu Leu Asp Ser Thr Gly Arg Thr Tyr
1               5                   10

<210> SEQ ID NO 5
<211> LENGTH: 9
<212> TYPE: PRT
<213> ORGANISM: artificial
<220> FEATURE:
<223> OTHER INFORMATION: CDR3 domain of Immunoglobulin light chain

<400> SEQUENCE: 5
```

-continued

Trp Gln Gly Thr His Phe Pro His Thr
1               5

<210> SEQ ID NO 6
<211> LENGTH: 8
<212> TYPE: PRT
<213> ORGANISM: artificial
<220> FEATURE:
<223> OTHER INFORMATION: CDR1 domain of Immunoglobulin heavy chain

<400> SEQUENCE: 6

Gly Tyr Thr Phe Thr Glu Tyr Thr
1               5

<210> SEQ ID NO 7
<211> LENGTH: 8
<212> TYPE: PRT
<213> ORGANISM: artificial
<220> FEATURE:
<223> OTHER INFORMATION: CDR2 domain of Immunoglobulin heavy chain

<400> SEQUENCE: 7

Ile Asn Pro Lys Asn Gly Asp Thr
1               5

<210> SEQ ID NO 8
<211> LENGTH: 10
<212> TYPE: PRT
<213> ORGANISM: artificial
<220> FEATURE:
<223> OTHER INFORMATION: CDR3 domain of Immunoglobulin heavy chain

<400> SEQUENCE: 8

Ala Ser Pro Asp Leu Pro Pro Met Asp Tyr
1               5                   10

<210> SEQ ID NO 9
<211> LENGTH: 112
<212> TYPE: PRT
<213> ORGANISM: artificial
<220> FEATURE:
<223> OTHER INFORMATION: LCVR immunoglobulin

<400> SEQUENCE: 9

Asp Ile Gln Leu Thr Gln Ser Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Thr Gly Arg Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Leu Tyr Tyr Cys Trp Gln Gly
                85                  90                  95

Thr His Phe Pro His Thr Phe Gly Gly Gly Thr Lys Leu Glu Ile Lys
            100                 105                 110

<210> SEQ ID NO 10
<211> LENGTH: 116
<212> TYPE: PRT
<213> ORGANISM: artificial
<220> FEATURE:
<223> OTHER INFORMATION: HCVR Immunoglobulin

<400> SEQUENCE: 10

```
Val Lys Leu Gln Gln Ser Gly Pro Glu Leu Val Lys Pro Gly Ala Ser
1               5                   10                  15

Val Lys Ile Ser Cys Lys Thr Ser Gly Tyr Thr Phe Thr Glu Tyr Thr
            20                  25                  30

Ile His Trp Val Lys Gln Ser His Gly Lys Thr Leu Glu Trp Ile Gly
        35                  40                  45

Gly Ile Asn Pro Lys Asn Gly Asp Thr Ser Tyr Asn Gln Lys Phe Lys
    50                  55                  60

Gly Lys Ala Thr Leu Thr Val Asp Lys Ser Ser Asn Thr Ala Tyr Met
65                  70                  75                  80

Glu Phe Arg Ser Leu Thr Ser Glu Asp Ser Ala Val Tyr Tyr Cys Ala
                85                  90                  95

Ser Pro Asp Leu Pro Pro Met Asp Tyr Trp Gly Gln Gly Thr Thr Val
            100                 105                 110

Thr Val Ser Ser
        115
```

```
<210> SEQ ID NO 11
<211> LENGTH: 111
<212> TYPE: PRT
<213> ORGANISM: artificial
<220> FEATURE:
<223> OTHER INFORMATION: Humanized LCVR Immunoglobulin
<220> FEATURE:
<221> NAME/KEY: misc_feature
<222> LOCATION: (3)..(3)
<223> OTHER INFORMATION: X = Q, V or E
<220> FEATURE:
<221> NAME/KEY: misc_feature
<222> LOCATION: (10)..(10)
<223> OTHER INFORMATION: X = T or S
<220> FEATURE:
<221> NAME/KEY: misc_feature
<222> LOCATION: (12)..(12)
<223> OTHER INFORMATION: X = S or P
<220> FEATURE:
<221> NAME/KEY: misc_feature
<222> LOCATION: (15)..(15)
<223> OTHER INFORMATION: X = I or L
<220> FEATURE:
<221> NAME/KEY: misc_feature
<222> LOCATION: (24)..(24)
<223> OTHER INFORMATION: X = K or R
<220> FEATURE:
<221> NAME/KEY: misc_feature
<222> LOCATION: (40)..(40)
<223> OTHER INFORMATION: X = L or F
<220> FEATURE:
<221> NAME/KEY: misc_feature
<222> LOCATION: (41)..(41)
<223> OTHER INFORMATION: X = L, Q or H
<220> FEATURE:
<221> NAME/KEY: misc_feature
<222> LOCATION: (49)..(49)
<223> OTHER INFORMATION: X = K or R
<220> FEATURE:
<221> NAME/KEY: misc_feature
<222> LOCATION: (57)..(57)
<223> OTHER INFORMATION: X = K, N, D or H
<220> FEATURE:
<221> NAME/KEY: misc_feature
<222> LOCATION: (58)..(58)
<223> OTHER INFORMATION: X = L, R or W
<220> FEATURE:
<221> NAME/KEY: misc_feature
<222> LOCATION: (67)..(67)
<223> OTHER INFORMATION: X = T or S
<220> FEATURE:
<221> NAME/KEY: misc_feature
```

```
<222> LOCATION: (87)..(87)
<223> OTHER INFORMATION: X = L or V
<220> FEATURE:
<221> NAME/KEY: misc_feature
<222> LOCATION: (89)..(89)
<223> OTHER INFORMATION: X = L or V

<400> SEQUENCE: 11

Asp Ile Xaa Leu Thr Gln Ser Pro Leu Xaa Leu Xaa Val Thr Xaa Gly
1               5                   10                  15

Gln Pro Ala Ser Ile Ser Cys Xaa Ser Ser Gln Ser Leu Leu Ser Thr
            20                  25                  30

Gly Arg Thr Tyr Leu Asn Trp Xaa Xaa Gln Arg Pro Gly Gln Ser Pro
        35                  40                  45

Xaa Arg Leu Ile Tyr Leu Val Ser Xaa Xaa Asp Ser Gly Val Pro Asp
    50                  55                  60

Arg Phe Xaa Gly Ser Gly Ser Gly Thr Asp Phe Thr Leu Lys Ile Ser
65                  70                  75                  80

Arg Val Glu Ala Glu Asp Xaa Gly Xaa Tyr Tyr Cys Trp Gln Gly Thr
                85                  90                  95

His Phe Pro His Thr Phe Gly Gly Gly Thr Lys Leu Glu Ile Lys
            100                 105                 110

<210> SEQ ID NO 12
<211> LENGTH: 116
<212> TYPE: PRT
<213> ORGANISM: artificial
<220> FEATURE:
<223> OTHER INFORMATION: Humanized HCVR Immunoglobulin
<220> FEATURE:
<221> NAME/KEY: misc_feature
<222> LOCATION: (23)..(23)
<223> OTHER INFORMATION: X = T, A or V
<220> FEATURE:
<221> NAME/KEY: misc_feature
<222> LOCATION: (33)..(33)
<223> OTHER INFORMATION: X = I, M or V
<220> FEATURE:
<221> NAME/KEY: misc_feature
<222> LOCATION: (49)..(49)
<223> OTHER INFORMATION: X = G, D, Y, M, W, E or I
<220> FEATURE:
<221> NAME/KEY: misc_feature
<222> LOCATION: (82)..(82)
<223> OTHER INFORMATION: X = F or L

<400> SEQUENCE: 12

Val Lys Leu Gln Gln Ser Gly Pro Glu Leu Val Lys Pro Gly Ala Ser
1               5                   10                  15

Val Lys Ile Ser Cys Lys Xaa Ser Gly Tyr Thr Phe Thr Glu Tyr Thr
            20                  25                  30

Xaa His Trp Val Lys Gln Ser His Gly Lys Thr Leu Glu Trp Ile Gly
        35                  40                  45

Xaa Ile Asn Pro Lys Asn Gly Asp Thr Ser Tyr Asn Gln Lys Phe Lys
    50                  55                  60

Gly Lys Ala Thr Leu Thr Val Asp Lys Ser Ser Asn Thr Ala Tyr Met
65                  70                  75                  80

Glu Xaa Arg Ser Leu Thr Ser Glu Asp Ser Ala Val Tyr Tyr Cys Ala
                85                  90                  95

Ser Pro Asp Leu Pro Pro Met Asp Tyr Trp Gly Gln Gly Thr Thr Val
            100                 105                 110

Thr Val Ser Ser
            115
```

<210> SEQ ID NO 13
<211> LENGTH: 34
<212> TYPE: DNA
<213> ORGANISM: artificial
<220> FEATURE:
<223> OTHER INFORMATION: VH-FOR PCR primer

<400> SEQUENCE: 13
tgaggagacg gtgaccgtgg tcccttggcc ccag                         34

<210> SEQ ID NO 14
<211> LENGTH: 22
<212> TYPE: DNA
<213> ORGANISM: artificial
<220> FEATURE:
<223> OTHER INFORMATION: VH-BACK PCR primer

<400> SEQUENCE: 14
aggtsmarct gcagsagtcw gg                                      22

<210> SEQ ID NO 15
<211> LENGTH: 22
<212> TYPE: DNA
<213> ORGANISM: artificial
<220> FEATURE:
<223> OTHER INFORMATION: VL-FOR PCR primer

<400> SEQUENCE: 15
gttagatctc cagcttggtc cc                                      22

<210> SEQ ID NO 16
<211> LENGTH: 24
<212> TYPE: DNA
<213> ORGANISM: artificial
<220> FEATURE:
<223> OTHER INFORMATION: VL-BACK PCR primer

<400> SEQUENCE: 16
gacattcagc tgacccagtc tcca                                    24

<210> SEQ ID NO 17
<211> LENGTH: 396
<212> TYPE: DNA
<213> ORGANISM: mus musculus
<220> FEATURE:
<221> NAME/KEY: misc_feature
<223> OTHER INFORMATION: 3A11-VH domain

<400> SEQUENCE: 17
gaggtccaac tgcagcagtc aggggggaggc ttagtgcagc ctggagggtc cctgaaactc    60
tcctgtgcaa cctctggatt cactttcagt gactattaca tgttttgggt tcgccagact   120
ccagagaaga ggctggagtg ggtcgcacac attaccaata taggtggtaa cacctattat   180
ccagacactg taaagggccg attcaccatc tccagagaca tgacaagaa cacccctgtac   240
ctgcaaatga gccgtctgaa gtctgaagac acagccatgt attactgtgc aagaccccccc  300
tcctatggta actacgggta cttcaatgtc tggggccaag ggaccacggt caccgtctcc   360
tcactggggc caagggacca cggtcaccgc tcctca                             396

<210> SEQ ID NO 18
<211> LENGTH: 132
<212> TYPE: PRT
<213> ORGANISM: mus musculus
<220> FEATURE:
<221> NAME/KEY: misc_feature
<223> OTHER INFORMATION: 3A11-VH domain

<400> SEQUENCE: 18

Glu Val Gln Leu Gln Gln Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
            20                  25                  30

Tyr Met Phe Trp Val Arg Gln Thr Pro Glu Lys Arg Leu Glu Trp Val
        35                  40                  45

Ala His Ile Thr Asn Ile Gly Gly Asn Thr Tyr Tyr Pro Asp Thr Val
    50                  55                  60

Lys Gly Arg Phe Thr Ile Ser Arg Asp Asn Asp Lys Asn Thr Leu Tyr
65                  70                  75                  80

Leu Gln Met Ser Arg Leu Lys Ser Glu Asp Thr Ala Met Tyr Tyr Cys
                85                  90                  95

Ala Arg Pro Pro Ser Tyr Gly Asn Tyr Gly Tyr Phe Asn Val Trp Gly
            100                 105                 110

Gln Gly Thr Thr Val Thr Val Ser Ser Leu Gly Pro Arg Asp His Gly
        115                 120                 125

His Arg Ser Ser
        130

<210> SEQ ID NO 19
<211> LENGTH: 372
<212> TYPE: DNA
<213> ORGANISM: mus musculus
<220> FEATURE:
<221> NAME/KEY: misc_feature
<223> OTHER INFORMATION: 3A11-VL domain

<400> SEQUENCE: 19
gacattgtgg tcattcaatc tccagcttct ttggctgtgt ctctagggca gagagccacc      60
atctcctgca gagccagtga aagtgttgaa tattatggca agtttaat gcagtggtac      120 caacagaaac caggacagcc acccaaactc ctcatctata ctgcgtccaa cgtagaatct      180
ggggtccctg ccaggtttag tggcagtggg tctgggacag acttcagcct caacatccat      240
cctgtggagg aggatgatat tgcaatgtat ttctgtcagc aaagtaggaa ggttccgtac      300
acgttcggag gggggaccaa gctggaaata aaacgggctg atgctgcacc aactgtatcc      360
atcttcccac ca                                                         372

<210> SEQ ID NO 20
<211> LENGTH: 124
<212> TYPE: PRT
<213> ORGANISM: mus musculus
<220> FEATURE:
<221> NAME/KEY: misc_feature
<223> OTHER INFORMATION: 3A11-VL domain

<400> SEQUENCE: 20

Asp Ile Val Val Ile Gln Ser Pro Ala Ser Leu Ala Val Ser Leu Gly
1               5                   10                  15

Gln Arg Ala Thr Ile Ser Cys Arg Ala Ser Glu Ser Val Glu Tyr Tyr
            20                  25                  30

Gly Thr Ser Leu Met Gln Trp Tyr Gln Gln Lys Pro Gly Gln Pro Pro
        35                  40                  45

Lys Leu Leu Ile Tyr Thr Ala Ser Asn Val Glu Ser Gly Val Pro Ala
    50                  55                  60

Arg Phe Ser Gly Ser Gly Ser Gly Thr Asp Phe Ser Leu Asn Ile His

```
                65                  70                  75                  80
Pro Val Glu Glu Asp Asp Ile Ala Met Tyr Phe Cys Gln Gln Ser Arg
                    85                  90                  95

Lys Val Pro Tyr Thr Phe Gly Gly Thr Lys Leu Glu Ile Lys Arg
            100                 105                 110

Ala Asp Ala Ala Pro Thr Val Ser Ile Phe Pro Pro
        115                 120

<210> SEQ ID NO 21
<211> LENGTH: 351
<212> TYPE: DNA
<213> ORGANISM: mus musculus
<220> FEATURE:
<221> NAME/KEY: misc_feature
<223> OTHER INFORMATION: 15G5-VH domain

<400> SEQUENCE: 21
tcagggactg tgctggcaag gcctggggct tccgtgagga tgtcctgcaa ggcttctggc      60
tacagcttag ccacctactg gatgcactgg gtaaaacaga ggcctggaca gggtctagaa     120
tggattggtt ctatttatcc tggaaatggt gaaactacct acaaccagaa gttcaaggac     180
aaggccagac tgactgcagt cacatccgcc agcactgcct acatggagtt cagcagcctg     240
acaattgagg actctgcggt ctattactgt acaagagaga gggccgacgt atattactat     300
ggtatggact attggggcca aggaccacg gtcaccgtct cctcaaaggg c                351

<210> SEQ ID NO 22
<211> LENGTH: 117
<212> TYPE: PRT
<213> ORGANISM: mus musculus
<220> FEATURE:
<221> NAME/KEY: misc_feature
<223> OTHER INFORMATION: 15G5-VH domain

<400> SEQUENCE: 22

Ser Gly Thr Val Leu Ala Arg Pro Gly Ala Ser Val Arg Met Ser Cys
1               5                   10                  15

Lys Ala Ser Gly Tyr Ser Leu Ala Thr Tyr Trp Met His Trp Val Lys
            20                  25                  30

Gln Arg Pro Gly Gln Gly Leu Glu Trp Ile Gly Ser Ile Tyr Pro Gly
        35                  40                  45

Asn Gly Glu Thr Thr Tyr Asn Gln Lys Phe Lys Asp Lys Ala Arg Leu
    50                  55                  60

Thr Ala Val Thr Ser Ala Ser Thr Ala Tyr Met Glu Phe Ser Ser Leu
65                  70                  75                  80

Thr Ile Glu Asp Ser Ala Val Tyr Tyr Cys Thr Arg Glu Arg Ala Asp
                85                  90                  95

Val Tyr Tyr Tyr Gly Met Asp Tyr Trp Gly Gln Gly Thr Thr Val Thr
            100                 105                 110

Val Ser Ser Lys Gly
        115

<210> SEQ ID NO 23
<211> LENGTH: 357
<212> TYPE: DNA
<213> ORGANISM: mus musculus
<220> FEATURE:
<221> NAME/KEY: misc_feature
<223> OTHER INFORMATION: 15G5-VL domain

<400> SEQUENCE: 23
```

```
caaattgttc tcacccagtc tccagcaatc atgtctgcat ctccagggga gaaggtctcc      60
ataacctgca gtgccagctc aagtatagct cacatgtact ggttccagca gaagccagac     120
acttctccca aactctggat tacagcaca tccaacctgg cttctggagt cccttctcgc      180
ttcagtggca gtggatctgg gacctcttac tctctcacaa tcagccgaat ggaggctgaa     240
gatgctgcca cttattactg ccaccaaagg agtagttacc cattcacgtt cggctcgggg     300
acaaagttgg aagtaaaacg ggctgatgct gcaccaactg tatccatctt cccacca        357
```

<210> SEQ ID NO 24
<211> LENGTH: 119
<212> TYPE: PRT
<213> ORGANISM: mus musculus
<220> FEATURE:
<221> NAME/KEY: misc_feature
<223> OTHER INFORMATION: 15G5-VL domain

<400> SEQUENCE: 24

Gln Ile Val Leu Thr Gln Ser Pro Ala Ile Met Ser Ala Ser Pro Gly
1               5                   10                  15

Glu Lys Val Ser Ile Thr Cys Ser Ala Ser Ser Ser Ile Ala His Met
            20                  25                  30

Tyr Trp Phe Gln Gln Lys Pro Asp Thr Ser Pro Lys Leu Trp Ile Tyr
        35                  40                  45

Ser Thr Ser Asn Leu Ala Ser Gly Val Pro Ser Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys His Gln Arg Ser Ser Tyr Pro Phe Thr
                85                  90                  95

Phe Gly Ser Gly Thr Lys Leu Glu Val Lys Arg Ala Asp Ala Ala Pro
            100                 105                 110

Thr Val Ser Ile Phe Pro Pro
        115

<210> SEQ ID NO 25
<211> LENGTH: 14
<212> TYPE: PRT
<213> ORGANISM: artificial
<220> FEATURE:
<223> OTHER INFORMATION: 1H12 mAb epitope from LG4/5

<400> SEQUENCE: 25

Asp Ser Lys Pro Leu Tyr Thr Pro Ser Ser Ser Phe Gly Val
1               5                   10

<210> SEQ ID NO 26
<211> LENGTH: 12
<212> TYPE: PRT
<213> ORGANISM: artificial
<220> FEATURE:
<223> OTHER INFORMATION: 1H12 mAb epitope from Family 1

<400> SEQUENCE: 26

Tyr Gln Glu Glu Thr Pro Ala Ser Ser Phe Ser Arg
1               5                   10

<210> SEQ ID NO 27
<211> LENGTH: 12
<212> TYPE: PRT
<213> ORGANISM: artificial
<220> FEATURE:
<223> OTHER INFORMATION: 1H12 mAb epitope from Family 2

```
<400> SEQUENCE: 27

Leu Pro Val Pro Ala Tyr Asn Met Ser Ser Lys Phe
1               5                   10

<210> SEQ ID NO 28
<211> LENGTH: 12
<212> TYPE: PRT
<213> ORGANISM: artificial
<220> FEATURE:
<223> OTHER INFORMATION: 1H12 mAb epitope from Family 3

<400> SEQUENCE: 28

Ala Pro Gly Lys Ala Thr Trp Pro Ser Ser Lys Phe
1               5                   10

<210> SEQ ID NO 29
<211> LENGTH: 8
<212> TYPE: PRT
<213> ORGANISM: Mus musculus
<220> FEATURE:
<221> NAME/KEY: misc_feature
<223> OTHER INFORMATION: CDR1 from 3A11-VH domain

<400> SEQUENCE: 29

Gly Phe Thr Phe Ser Asp Tyr Tyr
1               5

<210> SEQ ID NO 30
<211> LENGTH: 8
<212> TYPE: PRT
<213> ORGANISM: Mus musculus
<220> FEATURE:
<221> NAME/KEY: misc_feature
<223> OTHER INFORMATION: CDR2 from 3A11-VH domain

<400> SEQUENCE: 30

Ile Thr Asn Ile Gly Gly Asn Thr
1               5

<210> SEQ ID NO 31
<211> LENGTH: 14
<212> TYPE: PRT
<213> ORGANISM: Mus musculus
<220> FEATURE:
<221> NAME/KEY: misc_feature
<223> OTHER INFORMATION: CDR3 from 3A11-VH domain

<400> SEQUENCE: 31

Ala Arg Pro Pro Ser Tyr Gly Asn Tyr Gly Tyr Phe Asn Val
1               5                   10

<210> SEQ ID NO 32
<211> LENGTH: 10
<212> TYPE: PRT
<213> ORGANISM: Mus musculus
<220> FEATURE:
<221> NAME/KEY: misc_feature
<223> OTHER INFORMATION: CDR1 from 3A11-VL domain

<400> SEQUENCE: 32

Glu Ser Val Glu Tyr Tyr Gly Thr Ser Leu
1               5                   10

<210> SEQ ID NO 33
<211> LENGTH: 3
<212> TYPE: PRT
<213> ORGANISM: Mus musculus
```

```
<220> FEATURE:
<221> NAME/KEY: misc_feature
<223> OTHER INFORMATION: CDR2 from 3A11-VL domain

<400> SEQUENCE: 33

Thr Ala Ser
1

<210> SEQ ID NO 34
<211> LENGTH: 9
<212> TYPE: PRT
<213> ORGANISM: Mus musculus
<220> FEATURE:
<221> NAME/KEY: misc_feature
<223> OTHER INFORMATION: CDR3 from 3A11-VL domain

<400> SEQUENCE: 34

Gln Gln Ser Arg Lys Val Pro Tyr Thr
1               5

<210> SEQ ID NO 35
<211> LENGTH: 8
<212> TYPE: PRT
<213> ORGANISM: Mus musculus
<220> FEATURE:
<221> NAME/KEY: misc_feature
<223> OTHER INFORMATION: CDR1 from 15G5-VH domain

<400> SEQUENCE: 35

Gly Tyr Ser Leu Ala Thr Tyr Trp
1               5

<210> SEQ ID NO 36
<211> LENGTH: 8
<212> TYPE: PRT
<213> ORGANISM: Mus musculus
<220> FEATURE:
<221> NAME/KEY: misc_feature
<223> OTHER INFORMATION: CDR2 from 15G5-VH domain

<400> SEQUENCE: 36

Ile Tyr Pro Gly Asn Gly Glu Thr
1               5

<210> SEQ ID NO 37
<211> LENGTH: 14
<212> TYPE: PRT
<213> ORGANISM: Mus musculus
<220> FEATURE:
<221> NAME/KEY: misc_feature
<223> OTHER INFORMATION: CDR3 from 15G5-VH domain

<400> SEQUENCE: 37

Thr Arg Glu Arg Ala Asp Val Tyr Tyr Tyr Gly Met Asp Tyr
1               5                   10

<210> SEQ ID NO 38
<211> LENGTH: 5
<212> TYPE: PRT
<213> ORGANISM: Mus musculus
<220> FEATURE:
<221> NAME/KEY: misc_feature
<223> OTHER INFORMATION: CDR1 from 15G5-VL domain
```

-continued

```
<400> SEQUENCE: 38

Ser Ser Ile Ala His
1               5

<210> SEQ ID NO 39
<211> LENGTH: 3
<212> TYPE: PRT
<213> ORGANISM: Mus musculus
<220> FEATURE:
<221> NAME/KEY: misc_feature
<223> OTHER INFORMATION: CDR2 from 15G5-VL domain

<400> SEQUENCE: 39

Ser Thr Ser
1

<210> SEQ ID NO 40
<211> LENGTH: 9
<212> TYPE: PRT
<213> ORGANISM: Mus musculus
<220> FEATURE:
<221> NAME/KEY: misc_feature
<223> OTHER INFORMATION: CDR3 from 15G5-VL domain

<400> SEQUENCE: 40

His Gln Arg Ser Ser Tyr Pro Phe Thr
1               5
```

MONOCLONAL ANTIBODIES DIRECTED AGAINST LG4-5 DOMAIN OF ALPHA3 CHAIN OF HUMAN LAMININ-5

FIELD OF THE INVENTION

The present invention relates to the field of cancer therapy, using monoclonal antibodies. More precisely, the invention concerns a monoclonal antibody binding to the LG4/5 domain of chain alpha3 of human protein laminin-5, wherein said monoclonal antibody inhibits the binding of syndecan-1 to said laminin-5 alpha3 chain LG4/5 domain. In particular, this invention relates to the 1H12 monoclonal antibody produced by the hybridoma cell line named 1H12 deposited on Jan. 8, 2008 at the C.N.C.M. under number I-3890, the 3A11 monoclonal antibody produced by the hybridoma cell line designated 3A11 deposited on Dec. 15, 2009 at the Collection Nationale de Cultures de Microorganismes (C.N.C.M., INSTITUT PASTEUR, 25 rue du Docteur Roux, F-75724 PARIS Cedex 15, FRANCE) under number I-4267, the 15G5 monoclonal antibody produced by the hybridoma cell line designated 15G5 deposited on Dec. 15, 2009 at the Collection Nationale de Cultures de Microorganismes (C.N.C.M., INSTITUT PASTEUR, 25 rue du Docteur Roux, F-75724 PARIS Cedex 15, FRANCE) under number I-4268, as well as chimerized, humanized derivatives and fragments thereof, and nucleic acid sequences encoding them, as well as vectors and host cells expressing them. The invention further relates to the medical application of such antibodies, in particular for treating cancer.

BACKGROUND ART

Cancer is the second mortality cause in developed countries, with more than 11 millions people diagnosed as suffering from cancer each year, and 7 millions people killed by cancer each year in the world according to World Health Organization (WHO). Cancer is thus an important public health problem in developed countries, and the ageing of their population will cause these numbers to continue to increase even if age-specific rates remain constant.

In Europe in 2004, the most common incident form of cancer was lung cancer (13.3% of all incident cases), followed by colorectal cancer (13.2%) and breast cancer (13%). Lung cancer was also the most common cause of cancer death (341 800 deaths), followed by colorectal (203 700), stomach (137 900) and breast (129 900). To make great progress quickly against cancer, the need is evident to make a concerted attack on the big killers: lung, colorectal, breast and stomach cancer.

Conventional treatments against cancer include surgery, radiotherapy and chemotherapy. While surgery usually does not have many deleterious effects, it is not always possible and it is also usually not sufficient to cure cancer, since tumor cells may have escaped surgical removal. Thus, radiotherapy and chemotherapy are necessary, even when surgery is possible.

However, while most drugs may have deleterious effects, anticancer drugs are among those resulting in the worse adverse effects. Indeed, anticancer drugs are usually cytotoxic active agents with some preference for tumor cells, but which also display toxicity on other cells due to insufficient specificity for tumor cells, thus resulting in often serious adverse reactions. Although radiotherapy is more localized, it is also not specific of tumor cells and thus also results in serious adverse effects on healthy surrounding cells. As a result, while these treatments can be used during limited time periods, they cannot be continued after the tumor appears cured, and cancer relapses are often observed.

In addition, some patients develop resistance to their chemotherapy treatment.

There is thus a very important need for alternative cancer treatments with increased specificity for tumor cells and thus decreased adverse effects, and which might thus be used in alone or in combination with chemotherapy or radiotherapy and might in some cases (for instance when relapse is at high risk) be used in a more continuous therapy.

Among new anticancer molecules, monoclonal antibodies have emerged as a new class of successful drugs for hematopoietic malignant neoplasms and solid tumors; being now a major therapeutic strategy in clinical oncology.

Monoclonal antibodies are typically of the IgG class and generally react with antigens expressed on tumor target cells, with high specificity and affinity. They interfere with the functioning of cancer cells inactivating the targeted pathways, or bind to tumor cells and activate various cytotoxic mechanisms via recruitment of immune effectors (naked antibodies), or destroy cancer cells by focused delivery of radioisotopes or cellular toxins coupled to the IgGs (conjugated antibodies).

Since monoclonal antibodies are specific for a particular antigen, they will not affect cells that do not express their particular antigen. As a result, by selecting target antigens that are specifically expressed by tumor cells or that are implicated in mechanisms specifically needed by tumor cells, they display tumor specificity and thus generate much less adverse effects than conventional anticancer molecules.

Currently there are 9 naked or conjugated antibodies approved by the Food and Drug Administration (FDA) and European Medicines Agency (EMEA) for human cancer treatments. In addition, numerous antibodies are in late clinical trial phases.

The most significant recent advances in the application of monoclonal antibodies (mAbs) to oncology have been the introduction and approval of bevacizumab (Avastin), an anti-vascular endothelial growth factor antibody, and of cetuximab (Erbitux), an anti-epidermal growth factor antibody. In combination with standard chemotherapy regimens, bevacizumab significantly prolongs the survival of patients with metastatic cancer of the colorectum, breast and lung. Cetuximab, used alone or with salvage chemotherapy, produces clinically meaningful anti-tumor responses in patients with chemotherapy-refractory cancers of the colon and rectum. In addition, the anti-HER/neu antibody trastuzumab (Herceptin), in combination with standard adjuvant chemotherapy, has been shown to reduce relapses and prolong disease-free and overall survival in high-risk patients after definitive local therapy for breast cancer. These exciting recent results highlight the great potential of monoclonal antibodies therapies for cancer treatment and provide optimism for the development of mAbs that bind novel targets, exploit novel mechanisms of action or possess improved tumor targeting.

Current developed anticancer monoclonal antibodies mostly target tumor specific antigens. While this permits high tumor specificity and thus low toxicity, the drawbacks are that it limits the treatment to tumors expressing this particular antigen. As a result, not all tumor types may be treated, and even among a particular tumor type, some patient may not respond to the treatment if their tumor does not express the targeted antigen.

Another approach for the development of anticancer monoclonal antibodies is thus to target not the tumor itself but its microenvironment, and particularly molecules of the microenvironment that are necessary for tumor growth.

Epithelial tissue represents the major site for human carcinogenesis and is involved in more than 90% of all cancers. While numerous genetic anomalies have been identified in many of these epithelial tumors, important questions remain regarding the molecular mechanisms involved in malignant transformation of tumor cells and in the metastatic process.

In order for tumors to grow and metastasize, neoplastic cells must invade and migrate into surrounding tissues. Metastatic spread of tumors to distal organs is the primary cause of death of cancer patients. Metastasis is a complex process, which involves the coordination of several signal transduction pathways that allow cancer cells to proliferate, remodel their surrounding environment, invade and migrate through new tissues.

Cellular invasive and migratory behaviour is governed at both extracellular and intracellular levels and depends on the carefully balanced dynamic interaction of the cell with its extracellular matrix (ECM). It is well established that adhesion to ECM proteins plays a key role in the assembly of cells into functional multicellular organisms and that such adhesions are involved in transmembrane signalling processes that regulate cell behaviour and fate. Novel insights into the mechanisms that regulate cell survival as well as cell migration and invasion have led to the conclusion that these highly regulated mechanisms are altered in cancer cells. The nature of the cell-matrix adhesion proteins (or related to adhesion) which are specifically involved in tumor development and cell invasion is still a pending question.

The ability to block cell adhesion proteins involved in the migratory and invasive capacity of tumor cells offers a promising approach to the treatment of patients with malignant disease.

While integrins are the major cell surface receptors for the ECM, other adhesive systems have also been described, including matrix and transmembrane receptors carrying glycosaminoglycans (GAGs) molecules on their ectodomain such as syndecans.

Both the expression pattern of these ECM receptors and the ligand-binding affinity determine the adhesive properties of the cell. The ligand-binding affinity of integrins may be regulated by intracellular cues, but through extracellular interactions integrins are also capable of signalling to the cellular machinery and thereby affecting gene expression and several cellular functions. Integrins and syndecans, which lack enzymatic activity, transmit their intracellular signals by interacting with various effector proteins, including both structural and signalling molecules. Following ligand binding, they cluster in adhesion complexes that contain several different actin-associated proteins that coordinate the "integration" of ECM components with the cellular cytoskeletal machinery. Cell-matrix adhesion receptors also activate kinases and phosphatases that phosphorylate or dephosphorylate cytoskeletal proteins, and thus regulate stress fibre formation, cell shape and motility. Furthermore, the cytoplasmic tail of adhesion receptors can recruit signalling proteins that modulate cell adhesion to the ECM. Cell movement results from a dynamic remodeling of the actin cytoskeleton and of its interaction with the plasma membrane and adhesion receptors.

Laminins (LN) belong to a growing family of heterotrimeric proteins, commonly found in basement membranes (BMs). These large molecules promote cell adhesion and migration via integrins and proteoglycan-type receptors. Over 15 LN isoforms are known with variable cell- and tissue-specific expression and are differentially recognized by cellular receptors. Expression of LN isoforms in tumors usually reflects expression in their normal counterpart. However, loss of the BM barrier often occurs during tumor invasion. In carcinomas, tumor cells at the invading front strongly express the LN5 isoform, remodelling of the vascular BM is observed during angiogenesis, and penetration of several BMs occurs during tumor dissemination and metastasis. Thus, deregulated cell-LN interactions are major traits of malignant disorders.

Laminin 5 (LN5, also abbreviated as LN332) is a major component of epithelial BMs and is composed of 3 chains (alpha3, beta3, gamma2) assembled into a cross-shaped heterotrimer (Rousselle et al., 1991, see FIG. 1).

Previously published research and literature has demonstrated and suggested that certain regions of LN5 may provide suitable targets for antibodies having anti-cancer properties. WO 2005/056598, WO 2005/040219, and WO 2005/052003, for example, indicate that antibodies directed to the gamma2 chain of LN5, particularly domain 3 thereof, may be useful anti-cancer agents.

Previously published literature also suggests that the alpha3 chain of LN5 may similarly be a useful target for anti-cancer antibodies. Various monoclonal antibodies directed to human LN5 (hLN5) alpha3 chain have thus been described, some of them being presented as useful for treating cancer.

The alpha3 chain comprises a large globular domain in its carboxyl-terminal region (G domain), which consists of five homologous globular subdomains, each containing about 200 amino acids (LG1-LG5). LN5 alpha3 chain canonical sequence is defined under UniProtKB/Swiss-Prot accession number Q16787-1, as represented by SEQ ID NO:1 (isoform A). Another isoform (isoform B) with incomplete sequence, as represented by SEQ ID NO:2 (UniProtKB/Swiss-Prot accession number Q16787-2), has been identified. Positions of the G1 to G5 domains in SEQ ID NO:1 (canonical isoform A) are displayed in following Table 1:

TABLE 1

Position of domains G1 to G5 in LN5 alpha3 chain

| Domain | Position | Length |
|--------|----------|--------|
| G1 | 770-971 | 202 |
| G2 | 978-1140 | 163 |
| G3 | 1147-1307 | 161 |
| G4 | 1366-1530 | 165 |
| G5 | 1537-1710 | 174 |

After secretion and deposition of precursor LN5 (pre-LN5) in the BM, one event results in the cleavage of the globular domains 4 and 5 (LG4/5) of the alpha3 chain. The resulting mature LN5 is the major component of anchoring filaments in skin, where it mediates cell adhesion via interaction of the LG1-3 triplet domain with both alpha3beta1and alpha6beta4integrins (Carter et al., 1991; Rousselle and Aumailley, 1994).

Antibodies to LN5 alpha3 chain may thus be directed either not to the G domain or, within the G domain, either to the LG1-LG3 subdomains that are present both in pre-LN5 and in mature LN5, or in the cleaved LG4-LG5 domains.

The 5 LG subdomains contains multiple cell binding sites with different mechanisms and different functions and are thus considered relevant to a number of cellular functions associated with LN5.

WO 2000/26342 suggests the use of various specific antibodies against LN5 alpha3 globular domains, generally, including monoclonal antibodies to human LN5 alpha3 chain with an observed effect on LN5 function named BM165, CM6, RG13 and P3H9-2, although no specific features of these antibodies are described. However, some of these antibodies have been further studied and characterized.

BM165 has been further shown to be directed against LN5 alpha3 LG2 domain and compared to antibody 7B2 also directed to LN5 alpha3 LG2 domain, which is suggested to inhibit migration and adhesion and to display antitumor activity (WO2008/005828).

RG13 has also been shown to be directed against LN5 alpha3 LG2 domain and to block migration and proliferation (Gonzales et al, 1999 and Goldfinger et al., 1999).

CM6 recognizes both pre-LN5 and mature LN5, thus demonstrating that the epitope is not situated in LG4-LG5 domains. It was shown to block adhesion and proliferation of tumor cells, without inducing apoptosis (Baker et al, 1996; Gonzales et al, 1999).

P3H9-2 recognizes a binding site for integrin and has been shown to inhibit adhesion and proliferation (Gonzales et al, 1999; Kim et al., 2000; and Wayner et al., 1993).

As indicated above, the LG1-3 triplet domain has been reported to interact with both alpha3beta1 and alpha6beta4 integrins (Carter et al., 1991; Rousselle and Aumailley, 1994). In particular, both LG2 and LG3 have been reported to have a binding site for integrin alpha3beta1 (Mizushima et al, 1997 and Shang et al, 2001). As a result, it is not surprising that the above described monoclonal antibodies directed to domains LG1-LG3 have been shown to display some activity on LN5 function and proposed for cancer treatment.

Although these antibodies have been generated a long time ago, none of them appears to have resulted in sufficiently satisfactory results to reach clinical trial. This is not surprising since the LG1-3 modules are (1) present in mature LN5, which is expressed in any epithelial basement membranes of normal tissues and (2) are involved in crucial integrin mediated cell adhesion mechanisms.

No binding site for integrin has been defined so far in LG4-LG5 domains of LN5 alpha3 chain. However, interactions with heparan sulphate proteoglycans in this region have been documented.

In particular, it has been shown that domain LG4 contains binding sites for syndecan-2 and syndecan-4 (Utani et al, 2001). In addition, domains LG4-LG5 (also abbreviated as LG4/5) have been shown to include a binding site for syndecan-1 (Okamoto et al., 2003; Bachy et al, 2008).

In addition, even though syndecan-1 binds to the LG4/5 domain when it is present in pre-LN5 or detached, it is not known whether the cleaved LG4/5 domains has a specific function.

WO 2005/073254 describes that LN5 alpha3 LG4/5 domains are important for squamous cell carcinoma (SCC) tumorigenesis. Indeed, this document first describes that transformed keratinocytes expressing only a truncated LN5 alpha3 chain gene lacking the LG4/5 domains fail to generate tumor invasion, while transformed keratinocytes with a normal LN5 alpha3 chain gene permit tumor invasion. This document then speculates on the usefulness of monoclonal antibodies to LN5 alpha3 LG4/5 domains for treating cancer. However, this is pure speculation since no such monoclonal antibody nor antigen to generate such antibody, is even prepared in this document.

Tran et al (2008) confirm the importance of LN5 alpha3 LG4/5 domains for squamous cell carcinoma (SCC) tumorigenesis. In addition, Tran et al show that treatment of mice suffering from SCC with a polyclonal antibody directed to LN5 alpha3 LG4/5 domains induced SCC tumor apoptosis, decreased SCC tumor proliferation, and impaired human SCC tumorigenesis in vivo without affecting normal tissue adhesion.

However, a polyclonal antibody is used, made of various specificities to distinct regions of LN5 alpha3 LG4/5 domains, that may target interactions with syndecan-1, 2, or 4, or even two or three of them. It thus cannot be derived from this article which region of LN5 alpha3 LG4/5 domains or which particular interaction(s) with syndecan-1, 2, and/or 4 should be targeted to reproduce anticancer activity.

In particular, while Tran et al show that heparin, as well as the anti-LN5 alpha3 LG4/5 polyclonal antibody, inhibit adhesion of transformed keratinocytes to LN5 alpha3 LG4/5 domains, it only speculates that interactions of LN5 alpha3 LG4/5 domains with syndecan-1, 2, and/or 4 may be implicated, with no indication in favour of syndecan-1.

In addition, using a polyclonal antibody, it is reasonable to think that the various antibody specificities target more than one of the interactions with syndecan-1, 2, and 4, and it is even not possible to conclude from this article that inhibition of only one of these interactions might be sufficient to obtain anticancer activity.

Two monoclonal antibodies directed to LN5 alpha3 LG4/5 domains have been described: clones 12C4 (Goldfinger et al., 1999) and D2-1 (Frank and Carter, 2004, Xia et al, 1996). However, no activity of these clones has been disclosed. Since both have been described several years ago, this clearly suggests that they have no activity on LN5 function, showing that not any region of LN5 alpha3 LG4/5 domains is suitable for obtaining an activity on LN5 function.

Thus, in view of the not well understood role of LG4/5 in cell adhesion and migration and in tumorigenesis, it is still not known from the prior art which region of the LG4/5 domains or which interaction of these domains with heparan sulphate proteoglycans (HSPG) syndecan-1, 2 and/or 4 should be targeted to obtain an anticancer activity. It is even not known if targeting of only one of these interactions might be sufficient to obtain anticancer activity.

In summary, it thus appears that various ligand molecules of LN5 (integrins alpha3beta1 and alpha3beta4, and HSPG syndecan-1, 2 and 4) are involved in its adhesion and migration functions, and may thus potentially be targeted for anticancer therapy using monoclonal antibodies.

However, the precise function of each of the interactions between LN5 and its ligands still remains to be elucidated, and it is currently not known which interaction should preferably be targeted for obtaining anticancer efficiency.

In addition, LN5 interacts with ligands on several of its three chains. For instance, there is a putative integrin binding site within the N-terminus of the gamma2 subunit (Decline and Rousselle, 2001). LN5 has also been reported to bind the extracellular domain of the transmembrane bullous pemphigoid antigen BP180 (Franzke et al., 2006). LN5 directly interacts with collagen type VII through the N-terminus of the beta3 laminin subunit and, to a lesser extent, the gamma2 LN subunit (Rousselle et al., 1997; Chen et al., 1999). In addition, the gamma2 subunit of LN5 has been shown to interact with type IV collagen, perlecan, and fibulin (Sasaki et al., 2001). LN5 also binds to other LN isoforms, LN 6 and 7 by the interaction of beta3 chain VI domain with the alpha3 chain short arm domain III of LN5 (Champliaud et al., 1996). This makes it even more difficult to choose a particular interaction and a particular chain domain.

There is thus a need for new anti-LG4/5 monoclonal antibodies with demonstrated anticancer activity.

The present invention provides monoclonal antibodies that inhibits the interaction between LN5 alpha3 chain LG4/5 domain and syndecan-1. In particular, the inventors generated three monoclonal antibodies, named 1H12, 3A11 and 15G5, which inhibit the interaction between LN5 alpha3 chain LG4/5 domain and syndecan-1, and which inhibits the growth of cells expressing pre-LN5 with the alpha3 chain LG4/5 domain, and particularly of colon carcinoma cells, breast carcinoma cells, and ovarian carcinoma cells.

SUMMARY OF THE INVENTION

The present invention relates to a monoclonal antibody, or fragment thereof, capable of binding to the LG4/5 domain of chain alpha3 of human protein laminin-5 (SEQ ID NO:3), wherein said monoclonal antibody, or fragments thereof, inhibits the binding of syndecan-1 to said laminin-5 alpha3 chain LG4/5 domain.

The present invention also relates to an isolated nucleic acid comprising a nucleic acid sequence encoding the monoclonal antibody according to the invention, or fragments thereof, which monoclonal antibody, or fragment thereof, is capable of binding to the LG4/5 domain of chain alpha3 of human protein laminin-5 (SEQ ID NO:1).

The present invention further relates to a vector comprising at least one nucleic acid sequence encoding the monoclonal antibody according to the invention, or fragments thereof, which monoclonal antibody, or fragment thereof, is capable of binding to the LG4/5 domain of chain alpha3 of human protein laminin-5 (SEQ ID NO:1), and regulatory sequences necessary for the expression of said nucleic acid sequence.

The present invention further relates to a host cell transfected by the vector according to the invention as described above.

The present invention still relates to the hybridoma cell line named 1H12 deposited on Jan. 8, 2008 at the Collection Nationale de Cultures de Microorganismes (C.N.C.M., INSTITUT PASTEUR, 25 rue du Docteur Roux, F-75724 PARIS Cedex 15, FRANCE) under number I-3890. It also relates to the hybridoma cell line named 3H11 deposited on Dec. 15, 2009 at the Collection Nationale de Cultures de Microorganismes (C.N.C.M., INSTITUT PASTEUR, 25 rue du Docteur Roux, F-75724 PARIS Cedex 15, FRANCE) under number I-4267. It further relates to the hybridoma cell line named 15G5 deposited on Dec. 15, 2009 at the Collection Nationale de Cultures de Microorganismes (C.N.C.M., INSTITUT PASTEUR, 25 rue du Docteur Roux, F-75724 PARIS Cedex 15, FRANCE) under number I-4268.

The present invention also relates to a medicament or pharmaceutical composition comprising a monoclonal antibody according to the invention, or fragments thereof, which monoclonal antibody, or fragment thereof, are capable of binding to the LG4/5 domain of chain alpha3 of human protein laminin-5 (SEQ ID NO:1), an isolated nucleic acid or a vector according to the invention as described above. In the case of a pharmaceutical composition, it may further comprise a pharmaceutically acceptable carrier.

The present invention further relates to a method for identifying a monoclonal antibody, or fragments thereof, according to claim 1, comprising the step of:
  i) contacting the LG4/5 domain of human protein laminin-5 (SEQ ID NO:3) with syndecan-1;
  ii) further contacting or not said LG4/5 domain of human protein laminin-5 (SEQ ID NO:3) and said syndecan-1 with a monoclonal antibody or fragment thereof to be tested, which monoclonal antibody has been obtained by the immunization of a non-human animal with a polypeptide comprising the LG4/5 domain of human protein laminin-5 (SEQ ID NO:3);
  iii) determining the binding of syndecan-1 to said LG4/5 domain of human protein laminin-5 (SEQ ID NO:3) in the presence or absence of said monoclonal antibody or fragment thereof to be tested; and
  iv) selecting the monoclonal antibody, or fragment thereof, which inhibits the binding of syndecan-1 to said LG4/5 domain of human protein laminin-5 (SEQ ID NO:3).

The present invention finally relates to a method for treating cancer in a subject in need thereof, comprising the administration to said subject of an efficient amount of a medicament comprising a monoclonal antibody according to the invention, or fragments thereof, which monoclonal antibody, or fragment thereof, are capable of binding to the LG4/5 domain of chain alpha3 of human protein laminin-5 (SEQ ID NO:1), an isolated nucleic acid according to the invention or a vector according to the invention as described above. The present invention thus also relates to the use of a monoclonal antibody according to the invention, or fragments thereof, which monoclonal antibody, or fragment thereof, are capable of binding to the LG4/5 domain of chain alpha3 of human protein laminin-5 (SEQ ID NO:1) for making a medicament for treating cancer.

DETAILED DESCRIPTION OF THE INVENTION

A first object of the present invention thus concerns a monoclonal antibody, or fragment thereof, capable of binding to the LG4/5 domain of chain alpha3 of human protein laminin-5 (SEQ ID NO:3), wherein said monoclonal antibody, or fragments thereof, inhibit the binding of syndecan-1 to said laminin-5 alpha3 chain LG4/5 domain.

As used herein, the "LG4/5 domain of chain alpha3 of human protein laminin-5" refers to the LG4 domain and LG5 domain of chain alpha3 of human protein laminin-5 corresponding to position 1366 to 1530 and 1537 to 1710 of SEQ ID NO: 1 respectively.

Methods for identifying monoclonal antibodies, or fragment thereof, capable of binding to the LG4/5 domain of chain α3 of human protein laminin-5 (SEQ ID NO:3), and of inhibiting the binding of syndecan-1 to said laminin-5 alpha3 chain LG4/5 domain can be simply determined by the skilled person in view of the present application. As an example such methods include the one disclosed in the example.

In a preferred embodiment, the antibody of the invention recognizes and binds to an epitope in the LG4/5 domain. Accordingly, the antibody of the invention is capable of binding to the precursor form of the alpha3 chain, but not to the mature form of alpha3 lacking the LG4/5 domain. In a further preferred embodiment, the antibody of the invention recognizes and binds to the epitope of sequence: LDSKPLYTPSSSF (SEQ ID NO: 25).

An antibody is an immunoglobulin molecule corresponding to a tetramer comprising four polypeptide chains, two identical heavy (H) chains (about 50-70 kDa when full length) and two identical light (L) chains (about 25 kDa when full length) inter-connected by disulfide bonds. Light chains are classified as kappa and lambda. Heavy chains are classified as gamma, mu, alpha, delta, or epsilon, and define the antibody's isotype as IgG, IgM, IgA, IgD, and IgE, respectively. Each heavy chain is comprised of a N-term heavy chain variable region (abbreviated herein as HCVR) and a heavy chain constant region. The heavy chain constant region is comprised of three domains (CH1, CH2, and CH3) for IgG, IgD, and IgA; and 4 domains (CH1, CH2, CH3, and CH4) for IgM and IgE. Each light chain is comprised of a N-term light chain variable region (abbreviated herein as LCVR) and a light chain constant region. The light chain constant region is comprised of one domain, CL. The HCVR and LCVR regions can be further subdivided into regions of hypervariability, termed complementarity determining regions (CDRs), interspersed with regions that are more conserved, termed framework regions (FR). Each HCVR and LCVR is composed of three CDRs and four FRs, arranged from amino-terminus to carboxy-terminus in the following order: FR1, CDR1, FR2, CDR2, FR3, CDR3, FR4.

The 4 "framework regions" (FR1, FR2, FR3 and FR4), which display less variability among antibodies, are involved in the formation of β sheets forming the structural framework of the variable domain, and the 3 "complementary determining regions" (CDR1, CDR2, CDR3), which correspond to 3 loops juxtaposed in the folded variable domain at the edge of each β sheet, are crucial for determining an antibody or antibody fragment specificity since they are the part of the variable domain mainly in contact with the antigen, especially the CDR3 region of each chain, which corresponds to the rearranged region of the heavy and light chains and is even more variable and more directly in contact with the specific antigen.

The assignment of amino acids to each domain is in accordance with well-known conventions and has been determined presently on the basis of the tools available at THE INTERNATIONAL IMMUNOGENETICS INFORMATION SYSTEM® (http://imgt.cines.fr).

The term "antibody", as used herein, refers to a monoclonal antibody per se. A monoclonal antibody can be a human antibody, a chimeric antibody and/or a humanized antibody.

A "monoclonal antibody", as used herein, is an antibody obtained from a population of substantially homogeneous antibodies, i.e. the antibodies forming this population are essentially identical except for possible naturally occurring mutations which might be present in minor amounts. By a "monoclonal antibody" is thus meant that only one particular antibody of defined specificity is present, and not a mixture of several antibodies with distinct sequences and specificities. These antibodies are directed against a single epitope and are therefore highly specific.

An "epitope" is the site on the antigen to which an antibody binds. It can be formed by contiguous residues or by non-contiguous residues brought into close proximity by the folding of an antigenic protein. Epitopes formed by contiguous amino acids are typically retained on exposure to denaturing solvents, whereas epitopes formed by non-contiguous amino acids are typically lost under said exposure.

By "monoclonal antibody fragment" is meant a polypeptide comprising at least a portion of the variable region of the immunoglobulin molecule that binds to its target, i.e., the antigen-binding region. Well-known "antibody fragments" include:
(i) a Fab fragment: a monovalent fragment consisting of the VL, VH, CL and CHI domains;
(ii) a F(ab')$_2$ fragment: a bivalent fragment comprising two Fab fragments linked by a disulfide bridge at the hinge region;
(iii) a Fv fragment consisting of the VL and VH domains of a single arm of an antibody;
(iv) a scFv fragment: a single chain variable fragment, which refers to a single folded polypeptide comprising the $V_H$ and $V_L$ domains of an antibody linked through a linker molecule. In such a scFv fragment, the $V_H$ and $V_L$ domains can be either in the $V_H$-linker-$V_L$ or $V_L$-linker-$V_H$ order. In addition to facilitate its production, a scFv fragment may contain a tag molecule linked to the scFv via a spacer. A scFv fragment thus comprises the $V_H$ and $V_L$ domains implicated into antigen recognition but not the immunogenic constant domains of the corresponding antibody.
(v) an isolated complementary determining region (CDR).

Preferably, said fragment is selected in the group comprising Fab, F(ab')2, Fv and scFv fragments.

The expression "capable of binding to the LG4/5 domain of chain alpha3 of human protein laminin-5 (SEQ ID NO:3)" refers to a $K_D$ of less than $10^{-7}$ M, preferably less than $10^{-8}$ M, and more preferably less than $10^{-9}$ M for the LG4/5 domain of chain alpha3 of human protein laminin-5 (SEQ ID NO:3).

As used herein, the term "$K_D$" refers to the dissociation constant of a particular antibody/antigen interaction. "Binding affinity" generally refers to the strength of the sum total of non-covalent interactions between a single binding site of a molecule {e.g., an antibody) and its binding partner (e.g., an antigen). Unless indicated otherwise, as used herein, "binding affinity" refers to intrinsic binding affinity that reflects a 1:1 interaction between members of a binding pair (e.g., antibody and antigen). The affinity of a molecule X for its partner Y can generally be represented by the $K_D$. Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention.

More specifically, the inventors have found that the 1H12 (produced by the hybridoma cell line named 1H12 deposited on Jan. 8, 2008 at the Collection Nationale de Cultures de Microorganismes (C.N.C.M., INSTITUT PASTEUR, 25 rue du Docteur Roux, F-75724 PARIS Cedex 15, FRANCE) under number I-3890, and referred to as 1H12 mAb), the 3A11 (produced by the hybridoma cell line designated 3A11 deposited on Dec. 15, 2009 at the Collection Nationale de Cultures de Microorganismes (C.N.C.M., INSTITUT PASTEUR, 25 rue du Docteur Roux, F-75724 PARIS Cedex 15, FRANCE) under number I-4267) and the 15G5 (produced by the hybridoma cell line designated 15G5 deposited on Dec. 15, 2009 at the Collection Nationale de Cultures de Microorganismes (C.N.C.M., INSTITUT PASTEUR, 25 rue du Docteur Roux, F-75724 PARIS Cedex 15, FRANCE) under number I-4268) monoclonal antibodies specifically target the interaction between syndecan-1 and laminin-5 alpha3 chain LG4/5 domain, and have anti-migration and/or anticancer activity.

Since FR regions are relatively conserved regions and have a non crucial role in antigen recognition, a mutated antibody with varying FR regions will most probably retain the specificity and functionalities of the 1H12, 3A11 or 15G5 antibody. In contrast, CDR regions are known to be involved in antigen recognition, so that a mutated antibody derived from the 1H12, 3A11 or 15G5 antibody should have a high percentage of identity with the original 1H12, 3A11 or 15G5 antibody to retain its specificity and functionalities.

Thus, in a preferred embodiment, the monoclonal antibody of the invention comprises:
a) a light chain comprising three light chain complementary regions (CDRs) having the following amino acid sequences:
i) the light chain CDR1: QSLLDSTGRTY (SEQ ID NO:4);
ii) the light chain CDR2: LVS;
iii) the light chain CDR3: WQGTHFPHT (SEQ ID NO:5); and
a light chain framework sequence from an immunoglobulin light chain; and b) a heavy chain comprising three heavy chain complementary regions (CDRs) having the following amino acid sequences:
  i) the heavy chain CDR1: GYTFTEYT (SEQ ID NO:6);
  ii) the heavy chain CDR2: INPKNGDT (SEQ ID NO:7);
  iii) the heavy chain CDR3: ASPDLPPMDY (SEQ ID NO:8); and
    a heavy chain framework sequence from an immunoglobulin heavy chain.

As such, the antibody of the invention comprises the CDR regions of the heavy chain and of the light chain of the 1H12 antibody, which CDRs regions are involved in the binding to the LG4/5 domain of chain alpha3 of human protein laminin-5 (SEQ ID NO:1).

In another preferred embodiment, the monoclonal antibody of the invention comprises:
a) a light chain comprising three light chain complementary regions (CDRs) having the following amino acid sequences:
  i) the light chain CDR1: ESVEYYGTSL (SEQ ID NO:32);
  iv) the light chain CDR2: TAS (SEQ ID NO: 33);
  v) the light chain CDR3: QQSRKVPYT (SEQ ID NO:34); and
    a light chain framework sequence from an immunoglobulin light chain; and
b) a heavy chain comprising three heavy chain complementary regions (CDRs) having the following amino acid sequences:
  i) the heavy chain CDR1: GFTFSDYY (SEQ ID NO:29);
  ii) the heavy chain CDR2: ITNIGGNT (SEQ ID NO:30);
  iii) the heavy chain CDR3: ARPPSYGNYGYFNV (SEQ ID NO:31); and
    a heavy chain framework sequence from an immunoglobulin heavy chain.

As such, the antibody of the invention comprises the CDR regions of the heavy chain and of the light chain of the 3A11 antibody, which CDRs regions are involved in the binding to the LG4/5 domain of chain alpha3 of human protein laminin-5 (SEQ ID NO:1).

In yet another preferred embodiment, the monoclonal antibody of the invention comprises:
a) a light chain comprising three light chain complementary regions (CDRs) having the following amino acid sequences:
  i) the light chain CDR1: SSIAH (SEQ ID NO:38);
  vi) the light chain CDR2: STS (SEQ ID NO:39);
  vii) the light chain CDR3: HQRSSYPFT (SEQ ID NO:40); and
    a light chain framework sequence from an immunoglobulin light chain; and
b) a heavy chain comprising three heavy chain complementary regions (CDRs) having the following amino acid sequences:
  i) the heavy chain CDR1: GYSLATYW (SEQ ID NO:35);
  ii) the heavy chain CDR2: IYPGNGET (SEQ ID NO:36);
  iii) the heavy chain CDR3: TRERADVYYYGMDY (SEQ ID NO:37); and
    a heavy chain framework sequence from an immunoglobulin heavy chain.

As such, the antibody of the invention comprises the CDR regions of the heavy chain and of the light chain of the 15G5 antibody, which CDRs regions are involved in the binding to the LG4/5 domain of chain alpha3 of human protein laminin-5 (SEQ ID NO:1).

In the sense of the present specification, the antibodies of the invention also include antibodies for which the 3 CDR regions of each chain (heavy and light) share a percentage of amino acid sequence identity of at least 80% with the CDRs disclosed above, preferably at least 85%, at least 90%, more preferably at least 91%, at least 92%, at least 93%, at least 94%, at least 95%, at least 96%, at least 97%, at least 98%, at least 99% or even 100%.

Since the CDR3 regions is thought to be the most crucial region for antigen recognition, the percentage of sequence identity in said CDR3 regions of the VH and VL domains should be as high as possible, and preferably at least 85%, preferably at least 90%, more preferably at least 91%, at least 92%, at least 93%, at least 94%, at least 95%, at least 96%, at least 97%, at least 98%, at least 99% or even 100%.

In a specific embodiment of this preferred embodiment, the monoclonal antibody of the invention is a chimerized antibody.

By "chimerized" antibody is meant an antibody, wherein with regards to a reference antibody of a given species, the framework regions (or in more basic cases the constant domains only) of said reference antibody have been replaced by corresponding framework regions (or constant domains only) of another species.

Preferably, said chimerized antibody comprises the constant regions from human immunoglobulin light and heavy chains.

Advantageously, said chimerized antibody comprises the light chain variable region (LCVR) with an amino acid sequence selected from the group consisting of DIQLTQSPLTLSVTIGQPASISCKSSQSLLDSTGR-TYLNWLLQRPGQSPKRLIYLV SKLDSGVP-DRFTGSGSGTDFTLKISRVEAEDLGLYYCWQGTHFP-HTFGGGTKLE IK (SEQ ID NO: 9), DIVVIQSPASLAVS-LGQRATISCRASESVEYYGTSLMQW-YQQKPGQPPKLLIYT ASNVESGVPARFSGSGSGTDF-SLNIHPVEEDDIAMYFCQQSRKVPYTFGGGTKL EIKRADAAPTVSIFPP (SEQ ID NO: 20), and QIVLTQS-PAIMSASPGEKVSITCSASSSIHMYW-FQQKPDTSPKLWIYSTSNLASG VPSRFSGSGSGTSYS-LTISRMEAEDAATYYCHQRSSYPFTFGSGTKLEVKR-ADA APTVSIFPP (SEQ NO: 24).

Again advantageously, said chimerized antibody comprises the heavy chain variable region (HCVR) with an amino acid sequence selected from the group consisting of VKLQQSGPELVKPGASVKISCKTSGYT-FTEYTIHWVKQSHGKTLEWIGGINPKN GDTSYNQK-FKGKATLTVDKSSNTAYMEFRSLTSED-SAVYYCASPDLPPMDYW GQGTTVTVSS (SEQ ID NO: 10), EVQLQQSGGGLVQPGGSLKLSCATSG-FTFSDYYMFWVRQTPEKRLEWVAHITN IGGNTYYP-DTVKGRFTISRDNDKNTLYLQMSRLK-SEDTAMYYCARPPSYGNYG YFNVWGQGTTVTVS (SEQ ID NO: 18), and SGTVLARPGASVRMSCKASGYS-LATYWMHWVKQRPGQGLEWIGSIYPGNGET TYN-QKFKDKARLTAVTSASTAYMEFSS-LTIEDSAVYYCTRERADVYYYGMDY WGQGTTVTVSSKG (SEQ ID NO: 22).

In a particular embodiment of this specific embodiment, said chimerized antibody is a humanized antibody.

The goal of humanization is a reduction in the immunogenicity of a xenogenic antibody, such as a murine antibody, for introduction into a human, while maintaining the full antigen binding affinity and specificity of the antibody. By "humanized" antibody is thus meant a chimerized antibody, wherein with regards to a reference antibody of a given species, the framework regions of said reference antibody have been replaced by human antibody framework regions, whereas the CDRs regions are identical in the chimerized antibody and in the reference antibody.

Thus, said humanized antibody further comprises humanized light and heavy chain variable regions (LCVR and HCVR respectively) and further comprises the constant regions from human immunoglobulin light and heavy chains.

To generate such a humanized antibody, several well known technologies may be used, including:

rational methods relying on the so-called design cycle. It consists of generating a small set of variants, which are designed based on the antibody structure and/or sequence information, and assessing their binding or any other characteristic of interest. Rational methods include CDR grafting, Resurfacing, Superhumanization and Human String Content Optimization. CDR grafting involves selecting the complementary determining regions (CDRs) from a donor antibody or antigen-binding fragment, and grafting them onto a human antibody or antigen-binding fragment framework of known three dimensional structure. In a typical method to choose the best human antibody candidate, aided by computer modeling and comparison to human germline sequences, the antigen binding loops of the monoclonal antibody to be humanized are superimposed onto the best fitting frameworks.

empirical methods based on generating large combinatorial libraries and selecting the desired variants by enrichment technologies such as phage, ribosome or yeast display, or by high throughput screening techniques. The latter methods rest on selection rather than making assumptions on the impact of mutations on the antibody structure. These methods include Framework Libraries, Guided Selection, Framework Shuffling and Humaneering.

Strategies and methods for humanizing antibodies are disclosed in e.g. U.S. Pat. No. 5,639,641; EP 0 239 400; WO 91/09967; U.S. Pat. Nos. 5,530,101; 5,585,089; EP 0 592 106; EP 0 519 596; Padlan E. A., 1991, *Molecular Immunology* 28(4/5): 489-498; Studnicka G. M. et al., 1994, *Protein Engineering* 7(6): 805-814; Roguska M. A. et al., 1994, *Proc. Natl. Acad. Sci. U.S.A.,* 91:969-973; Tsurushita N. et al., 2005, *Methods,* 36(1):69-83; and U.S. Pat. No. 5,565,332.

As an example, it has been possible to establish the sequences of possible humanized HCVR and LCVR by comparison (by BLAST algorithm) of 1H12 HCVR and LCVR of corresponding regions of human immunoglobulins.

As an example, a preferred light chain variable region (LCVR) of a humanized antibody of the present invention may have the amino acid sequence DI(QN/E)LTQSPL(T/S)L(S/P)VT(I/L)GQPASISC(K/R)SSQSLLSTGRTYLNW(L/F)(L/Q/H) QRPGQSP(K/R)RLIYLVS(K/N/D/H)(L/R/W)DSGVPDRF(T/S)GSGSGTDFT LKISRVEAED(L/V)G(L/V)YYCWQGTHFPHTFGGGTKLEIK (SEQ ID NO:11), wherein said amino acid sequence SEQ ID NO:11 differs from at least one amino acid compared to SEQ ID NO:9.

As another example, a preferred heavy chain variable region (HCVR) of a humanized antibody of the present invention may have the amino acid sequence VKLQQSGPELVKPGASVKISCK(T/A/V)SGYTFTEYT(I/M/V)HWVKQSHGKTLE WIG(G/D/Y/M/W/E/I)INPKNGDTSYNQKFKGKATLTVDKSSNTAYME(F/L)RSLT SEDSAVYYCASPDLPPMDYWGQGTTVTVSS (SEQ ID NO:12), wherein the amino acid sequence SEQ ID NO:12 differs from at least one amino acid compared to SEQ ID NO:10.

In another specific embodiment of this preferred embodiment, the monoclonal antibody of the invention is the 1H12 monoclonal antibody produced by the hybridoma cell line named 1H12 deposited on Jan. 8, 2008 at the Collection Nationale de Cultures de Microorganismes (C.N.C.M., INSTITUT PASTEUR, 25 rue du Docteur Roux, F-75724 PARIS Cedex 15, FRANCE) under number I-3890.

In another specific embodiment of this preferred embodiment, the monoclonal antibody of the invention is the 3A11 monoclonal antibody produced by the hybridoma cell line designated 3A11 deposited on Dec. 15, 2009 at the Collection Nationale de Cultures de Microorganismes (C.N.C.M., INSTITUT PASTEUR, 25 rue du Docteur Roux, F-75724 PARIS Cedex 15, FRANCE) under number I-4267.

In yet another specific embodiment of this preferred embodiment, the monoclonal antibody of the invention is the 15G5 monoclonal antibody produced by the hybridoma cell line designated 15G5 deposited on Dec. 15, 2009 at the Collection Nationale de Cultures de Microorganismes (C.N.C.M., INSTITUT PASTEUR, 25 rue du Docteur Roux, F-75724 PARIS Cedex 15, FRANCE) under number I-4268.

A second object of the present invention is an isolated nucleic acid comprising a nucleic acid sequence encoding a monoclonal antibody according to the invention, or fragments thereof, which monoclonal antibody, or fragment thereof, are capable of binding to the LG4/5 domain of chain alpha3 of human protein laminin-5 (SEQ ID NO:1).

Due to genetic code degeneracy, a multitude of distinct nucleic sequences may encode the same amino acid sequence and anyone of these nucleic sequences is included in the scope of the invention.

A third object of the present invention is a vector comprising at least one nucleic acid sequence encoding a monoclonal antibody according to the invention, or fragments thereof, which monoclonal antibody, or fragment thereof, are capable of binding to the LG4/5 domain of chain alpha3 of human protein laminin-5 (SEQ ID NO:1), and regulatory sequences necessary for the expression of said nucleic acid sequence.

As used herein, the term "regulatory sequences" refers to any sequence that allows, contributes to or modulates the expression of the nucleic acid molecule in a given host cell, including replication, duplication, transcription, splicing, translation, stability and/or transport of the nucleic acid or one of its derivative (i.e. mRNA) into the host cell. Such regulatory sequences notably include promoters, enhancers, signal sequences, and many other sequences well known to those skilled in the art.

Various types of vectors are included in the scope of the present invention, including bacterial plasmids, YACs, cosmids, viral vectors such as retrovirus- and EBV-derived episomes, and all the other vectors that the skilled man will know to be convenient for ensuring the expression of the heavy and/or light chains of the antibodies of the invention. The skilled man will realize that the polynucleotides encoding the heavy and the light chains can be cloned into different vectors or in the same vector. In a preferred embodiment, said polynucleotides are cloned in the same vector.

A fourth object of the present invention is a host cell transfected by the vector according to the invention as described above.

The term "recombinant host cell" (or simply "host cell"), as used herein, is thus intended to refer to a cell into which a recombinant expression vector has been introduced. The term "host cell" should be understood broadly so as to encompass isolated cells, a group of cells, as well as particular organization of cells, e.g. in tissue or organ. Such cells can be primary, transformed or cultured cells. They can be prokaryotic (e.g. *Escherichia coli*), yeast (e.g. *Saccharomyces cerevisiae, Saccharomyces pombe* or *Pichia pastoris*), eukaryotic (e.g. insect, plant and mammalian including human cells). The term "host cell" includes cells which can be or has been the recipient of the nucleic acid molecule or vector in use in this invention and progeny of such cells.

A fifth object of the present invention is the hybridoma cell lines named 1H12, 3A11, and 15G5, deposited respectively on Jan. 8, 2008, Dec. 15, 2009, and Dec. 15, 2009 at the Collection Nationale de Cultures de Microorganismes (C.N.C.M., INSTITUT PASTEUR, 25 rue du Docteur Roux, F-75724 PARIS Cedex 15, FRANCE) under numbers 1-3890, 1-4267 and 1-4268.

A sixth object of the present invention is a medicament or pharmaceutical composition comprising a monoclonal antibody according to the invention, or fragments thereof, which monoclonal antibody, or fragment thereof, is capable of binding to the LG4/5 domain of chain alpha3 of human protein laminin-5 (SEQ ID NO:1), an isolated nucleic acid or a vector according to the invention as described above. In the case of a pharmaceutical composition, it may further comprise a pharmaceutically acceptable carrier.

Said medicament or pharmaceutical composition may be used either as first treatment, alone or in combination with any other cancer treatment, or after a first cancer treatment intended for reducing tumor mass, in order to prevent relapse and/or metastasis.

The medicament or pharmaceutical composition according to the invention may be administered by any suitable route depending on the particular cancer treated, and the best dosage may be determined by any skilled artisan.

Such a medicament or pharmaceutical composition according to the invention, may particularly be intended for treating cancer, in particular epithelial cancers. These include notably carcinomas and any cancers that produce precursor LN5 or its LG4/5 domain. Among carcinomas, the medicament or pharmaceutical composition according to the invention may particularly be intended for treating colon, breast, ovarian, pancreas and lung carcinoma, and squamous cell carcinoma. In a preferred embodiment, colon carcinoma is treated. In another preferred embodiment, the medicament or pharmaceutical composition of the invention is intended for treating breast carcinoma. In yet another preferred embodiment, the medicament or pharmaceutical composition of the invention is intended for treating ovarian carcinoma.

A seventh object of the present invention is a method for identifying a monoclonal antibody, or fragments thereof, according to claim 1, comprising the step of:
 i) contacting the LG4/5 domain of human protein laminin-5 (SEQ ID NO:3) with syndecan-1;
 ii) further contacting or not said LG4/5 domain of human protein laminin-5 (SEQ ID NO:3) and said syndecan-1 with a monoclonal antibody or fragment thereof to be tested, which monoclonal antibody has been obtained by the immunization of a non-human animal with a polypeptide comprising the LG4/5 domain of human protein laminin-5 (SEQ ID NO:3);
 iii) determining the binding of syndecan-1 to said LG4/5 domain of human protein laminin-5 (SEQ ID NO:3) in the presence or absence of said monoclonal antibody or fragment thereof to be tested; and
 iv) selecting the monoclonal antibody, or fragment thereof, which inhibits the binding of syndecan-1 to said LG4/5 domain of human protein laminin-5 (SEQ ID NO:3).

As an example of such method, one can cite the one disclosed in the examples, which method is based on a specific syndecan-1 mediated cell adhesion assay in which cells adhesion is only due to the recognition of LG4/5 fragment by syndecan-1 expressed at the surface of target cells.

Still another object of the present invention is a method for treating cancer in a subject in need thereof, comprising the administration to said subject of an efficient amount of a medicament comprising a monoclonal antibody according to the invention, or fragments thereof, which monoclonal antibody, or fragment thereof, are capable of binding to the LG4/5 domain of chain alpha3 of human protein laminin-5 (SEQ ID NO:1), an isolated nucleic acid according to the invention or a vector according to the invention as described above.

As used herein, the term "subject" refers to a mammal, preferably to a human.

Preferably, a patient in need thereof corresponds to a patient suffering from cancer, in particular from an epithelial cancer. These include notably carcinomas and any cancers that produce precursor LN5 or its LG4/5 domain. As an example of carcinoma, one can cite colon, breast, ovarian, pancreas and lung carcinoma, and squamous cell carcinoma. In a preferred embodiment, said cancer is a colon, breast or ovarian carcinoma.

In such a method, the monoclonal antibody, fragment thereof, isolated nucleic acid or vector according to the invention may be used alone or in combination with another anticancer treatment.

The method of the invention may be particularly used as first treatment, alone or in combination with any other cancer treatment, or after a first cancer treatment intended for reducing tumor mass, in order to prevent relapse and/or metastasis.

Other embodiments and advantages of the present invention are illustrated in the following non-limiting examples.

Figure 1:
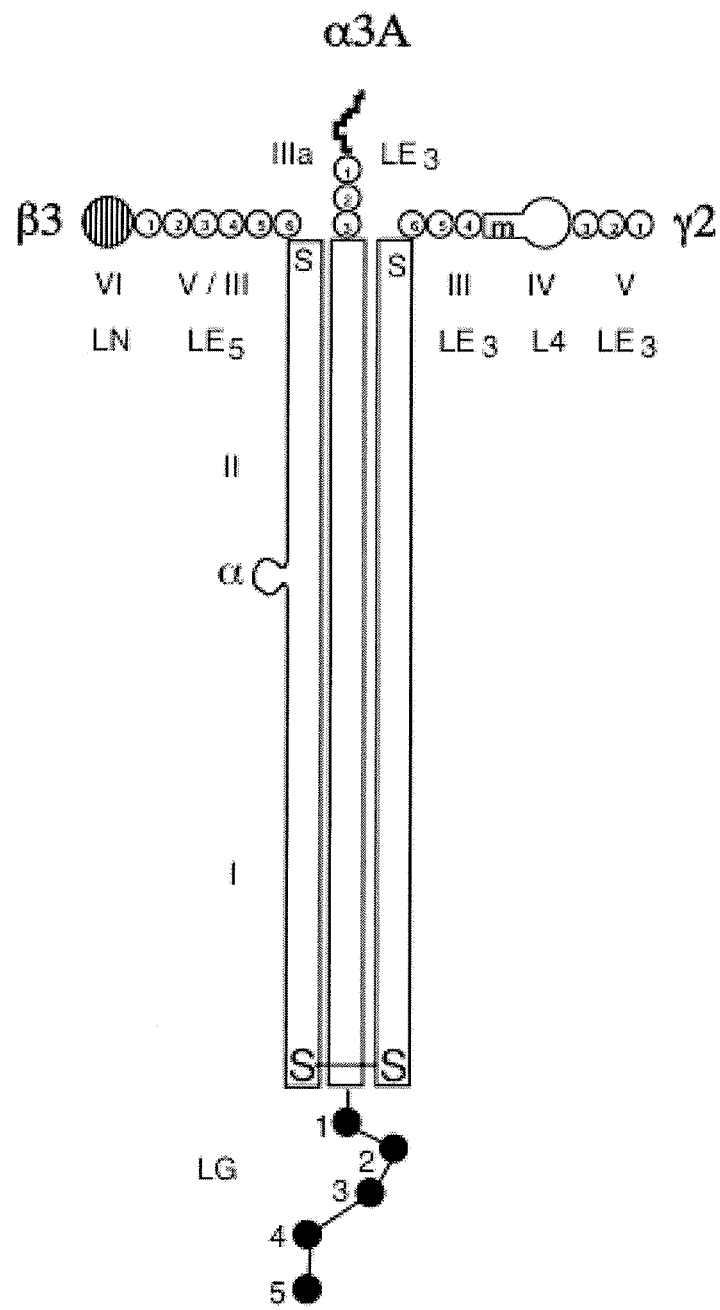
FIG. 1: Structure of laminin 5 (LN5)

NHK ($3\times10^6$ cells) were extracted with RIPA lysis buffer, pH 7.4 (Okamoto et al., 2003) containing 250 µM phenylmethylsulfonyl fluoride and 1 mM n-ethylmaleimide. After centrifugation, protein concentrations of lysates were determined and the equivalent amount of proteins were processed for pull-down experiments using beads covalently covered with 20 µg of LG4/5. Beads were pre-incubated with either PBS (lane 1), 100 pmole/ml of soluble heparin (lane 2) or 10 pmole/ml of the mAb 1H12 prior to the incubation with the cell lysates for 2 h. After washing, bound material was incubated in digestion buffer (20 mM sodium acetate, 5 mM $CaCl_2$, pH 7.0) and treated with 8 mU/ml heparitinase 1 and 50 mU/ml chondroitinase ABC for 2 h at 25° C. The proteins were resolved on 8% SDS-PAGE gel, transferred to nitrocellulose followed by immunodetection of syndecan-1. Molecular markers are annotated on the right.

Figure 6:
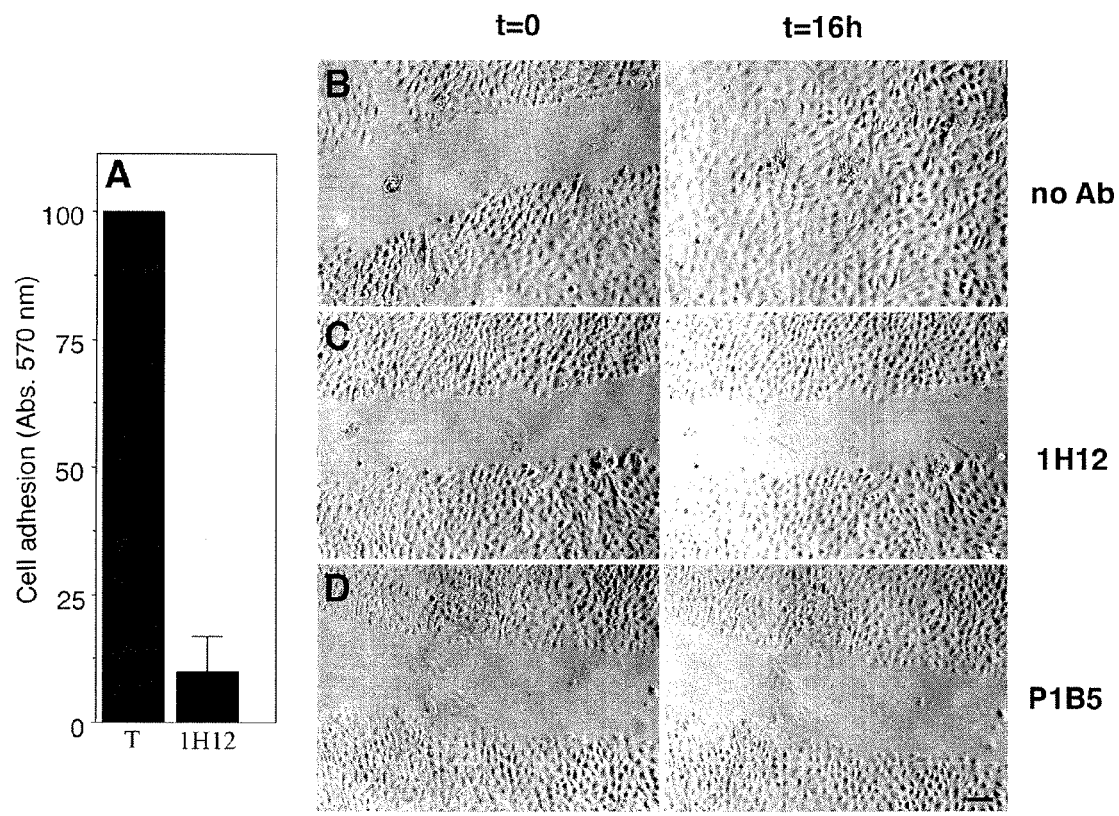

FIG. 6: The mAb 1H12 inhibits the migration of normal keratinocytes.

Inhibition of epithelial wound closure by the 1H12 function-blocking monoclonal antibody. (D) Effect of the mAb 1H12 on adhesion of the NHK used for the wound scrape assay, to the LG4/5 fragment. Multiwell plates were coated with LG4/5 at 0.3 µM. After saturation with 1% BSA, the wells were incubated with 20 pmole/ml of mAb 1H12 for 1 h before cell adhesion. Extent of cell adhesion was measured and expressed as the percent of adhesion in the absence of antibodies. (A, B, C) NHKs were grown at confluency on 24 well tissue culture plates. Medium was removed and the cell layer was scraped with a pipette tip. The scrape-wounded surface were washed with PBS and incubated for 16 h in culture medium at 37° C. in the absence (A), or presence of 20 pmole/ml of mAb 1H12 which inhibit the syndecan-1 binding site in the LG4/5 domain of pre-LN5 (B). As previously shown (Goldfinger et al., 1999), 20 pmole/ml of the P1B5 function-blocking mAb against the alpha3 integrin subunit was used in our assay as an inhibitory control (D). Bar, 100 µm.

FIG. 7: Expression of pre-LN5 and the LG4/5 fragment in the extracellular matrix of the colon carcinoma cell line HT29.

(A) SD S-PAGE and Western blot analysis of pre-LN5 localised in the extracellular matrix of the colon carcinoma cells HT29 (American Type Culture Collection, HTB-38). We have previously shown that the colon carcinoma HT29 cells produce LN5 (Remy et al., 2006). After the HT29 were grown to confluency, the medium was removed and the cells were washed in sterile PBS. The cells were removed by treating them for 5 min in sterile 20 mM $NH_4OH$. The matrix was washed three times in sterile water and was then removed from the substratum by solubilization in 0.325 M Tris-HCl, pH 6.9, 25% glycerol, 10% SDS with 5% β-mercaptoethanol and analysed by 8% SD S-PAGE. Immunoblot analysis were performed with the anti-alpha3beta3gamma2 pAb 4101, the anti-LG4/5 pAb and the anti-LG4/5 mAb 1H12 as indicated. Purified LN5 was used as a control, of which subunits molecular masses are annotated on the left. Molecular markers are annotated on the right. (B) Purified LG4/5 fragment (2 µg, lanes 1) and HT29 matrix (lanes 2) were resolved by 12% SDS-PAGE under reducing conditions and transferred to nitrocellulose followed by immunodetection with either the pAb against LG4/5 or the mAb 1H12 as annotated. The migration positions of molecular weight markers are shown on the right.

Figure 8:
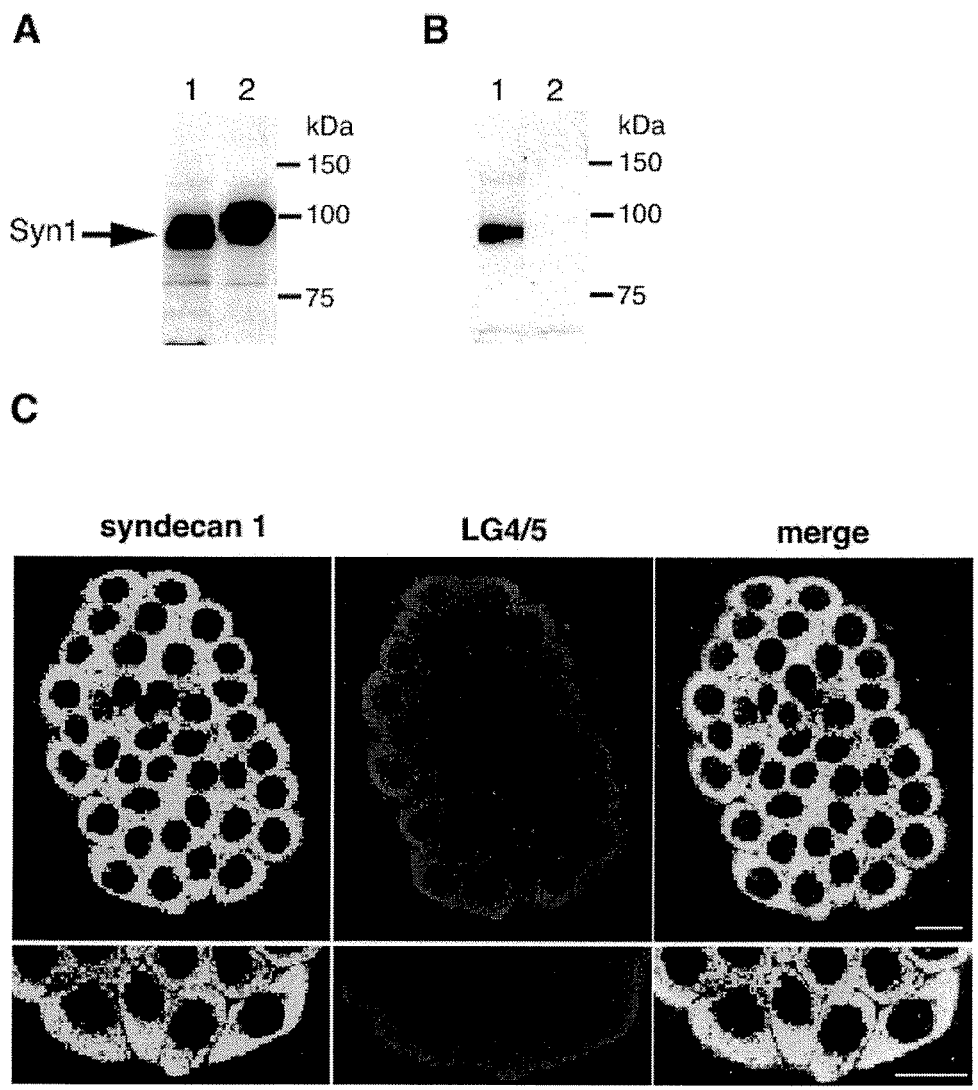

FIG. 8: Syndecan-1 from the colon carcinoma cells HT29 binds to the LG4/5 fragment.

(A) The colon carcinoma cells HT29 express large amount of syndecan-1, which binds to the LG4/5 fragment. Lysate were prepared from NHK (lane 1) and HT29 cells (lane 2) with RIPA buffer as in FIG. 5. Lysates corresponding to $3\times10^6$ cells were for pull-down experiments using beads covalently covered with 20 µg of LG4/5. After washing, bound material was incubated in digestion buffer (20 mM sodium acetate, 5 mM $CaCl_2$, pH 7.0) and treated with 8 mU/ml heparitinase 1 and 50 mU/ml chondroitinase ABC for 2 h at 25° C. The proteins were resolved on 8% SDS-PAGE gel, transferred to nitrocellulose followed by immunodetection of syndecan-1. Molecular markers are annotated on the right. (B) The 1H12 mAb inhibits the binding of syndecan-1 from HT29 cells to the LG4/5 fragment. HT29 cell lysates were used for LG4/5 pull-down experiments as described above. Beads were pre-incubated with either PBS (lane 1) or 10 pmole/ml of the 1H12 mAb (lane 2) prior to the incubation with the cell lysates for 2 h. After washing, bound material was incubated in digestion buffer and the proteins were resolved on 8% SD S-PAGE gel, transferred to nitrocellulose followed by immunodetection of syndecan-1. Molecular markers are annotated on the right. (C) Distribution of syndecan-1 and pre-LN5 in the cultured colon carcinoma cells HT29 analysed by confocal microscopy. Cultured HT29 cells were fixed, permeabilized and processed for immunofluorescence analysis. The distribution of syndecan-1 was studied using the mAb DL101, and that of the LG4/5 domain with the pAb against LG4/5. A view of an entire HT29 colony is shown. Note that syndecan-1 is expressed in all cells of the colony while intense pre-LN5 staining is seen exclusively in cells at the periphery. The merged image of cells shows a juxtaposition of the two specific stainings in cells localized at the edges of colonies in location where cells divide and migrate. A magnification of this particular staining is shown. Bars, 20 µm.

Figure 9:
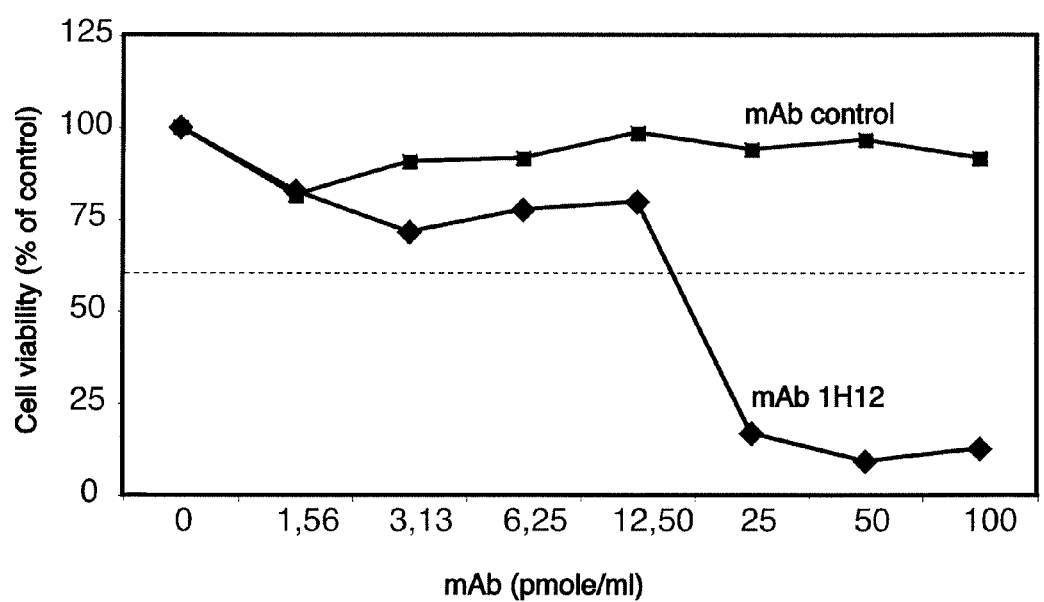

FIG. 9: Effect of the 1H12 mAb on HT29 colon carcinoma cell growth in vitro.

HT29 cells were plated in 96 well plates ($8 \times 10^3$ cells/well) in Dulbecco's modified Eagle medium (DMEM) containing 10% FCS and additives including 2 mM Glutamax (Gibco, Invitrogen, Cergy Pontoise, France). Two days after, medium was removed and replaced with DMEM 2% FCS, 2 mM Glutamax containing increasing concentrations of either 1H12 mAb or the 6F12 mAb control against the LN5 beta3 chain. This step was repeated 3 times and after 2 days in culture, the medium was removed and quantitation of living cells was determined using the Cell proliferation kit II (XTT, Roche Molecular Biomedicals).

Figure 10:
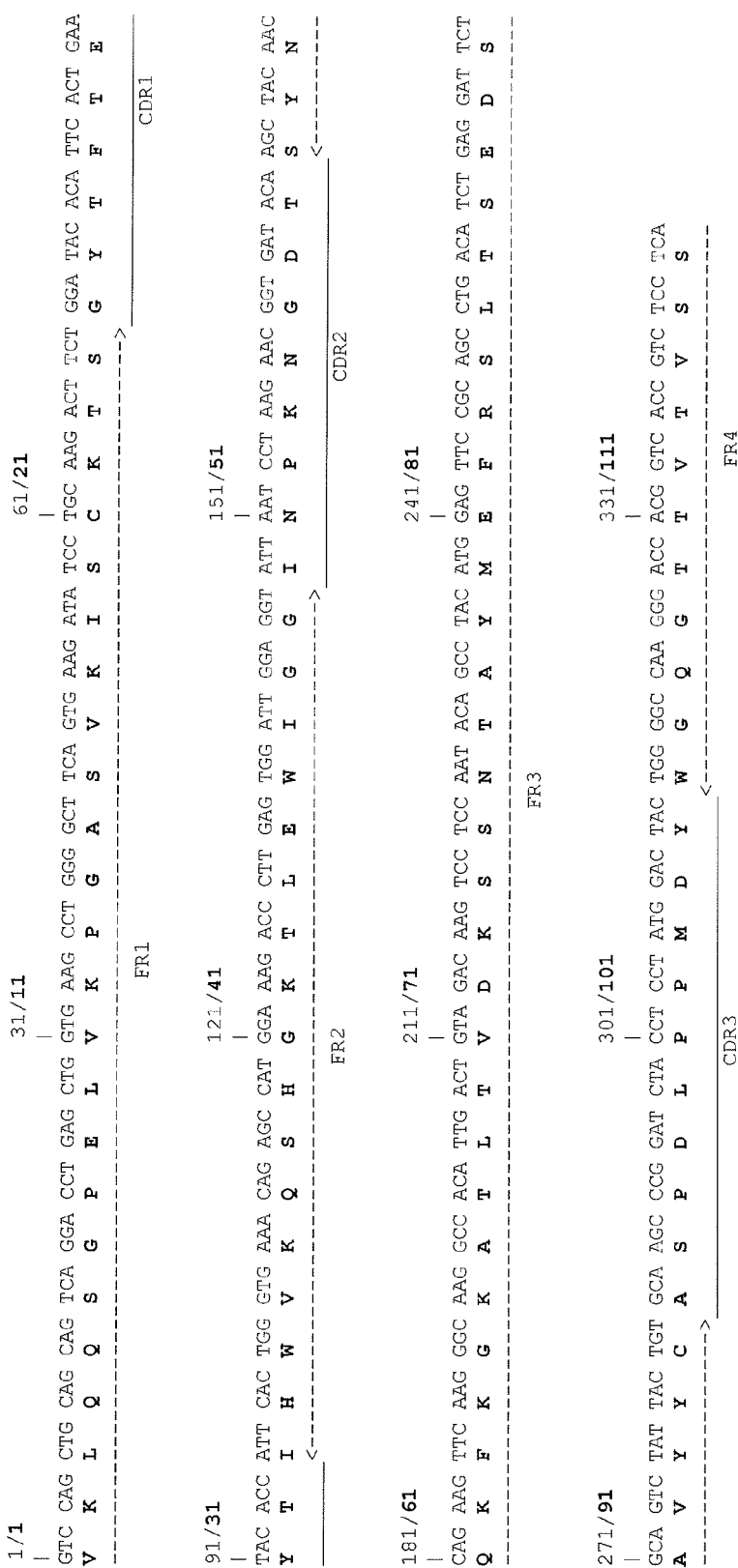
Figure 11:
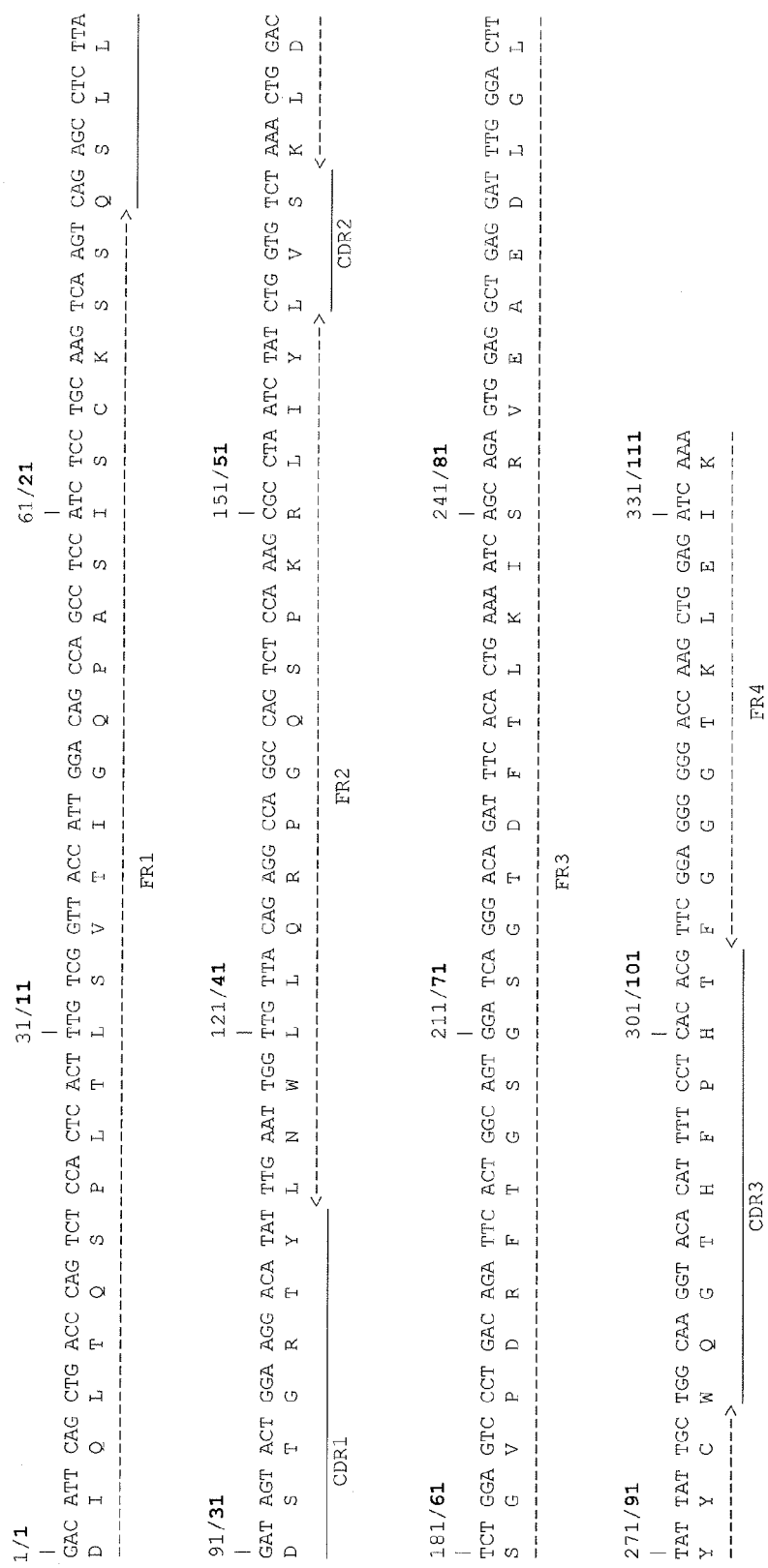

FIGS. 10 and 11: Cloning V domain genes of 1H12

Total RNA was isolated from the hybridoma cells 1H12 using RNeasy Plus (Qiagen, Courtaboeuf, France) according to the manufacturer's recommendations. Cloning of V domains of mouse immunoglobulin heavy chain (VH) and κ light chain genes (VL) was performed by RT-PCR (Titan one tube RT-PCR kit, Roche Diagnostics, Meylan, France) using oligonucleotide primers derived from conserved regions at each end of the cDNA sequences encoding VH and VL domains (Orlandi et al., 1988). For the VH domain, VH-FOR (5'-TGAGGAGACGGTGACCGTGGTCCCTTG-GCCCCAG, SEQ ID NO:13) and VH-BACK (5'-AGGTSM-ARCTGCAGSAGTCWGG, in which S=C or G, M=A or C, R=A or G, and W=A or T; SEQ ID NO:14) primers were used. For the VL domain, VL-FOR primer (5'-GTTAGATCTC-CAGCTTGGTCCC, SEQ ID NO:15) and VL-BACK (5'-GACATTCAGCTGACCCAGTCTCCA, SEQ ID NO:16) were utilised. RT-PCRs were as followed: 42° C., 30 min; 94° C., 2 min; and 40 cycles at 94° C., 30 s; 50° C., 30 s; 68° C., 1 min. PCR fragments were purified on 2% agarose gels, extracted from agarose (QUIAquick; Qiagen) and cloned by TA-cloning (Invitrogen, Cergy Pontoise, France) into pCRII-TOPO. For each PCR fragment, at least three independent clones were sequenced (Genome Express, Meylan, France) and cDNA sequences were compared to the IMGT mouse immunoglobulin data base (http://imgt.cines.fr/). Blast results for VH and VL genes are summarized Table 2 and 3 respectively. Framework regions (FR) and complementary determining regions (CDR) composing VH and VL domains are shown in FIGS. 10 and 11 respectively.

Figure 12:
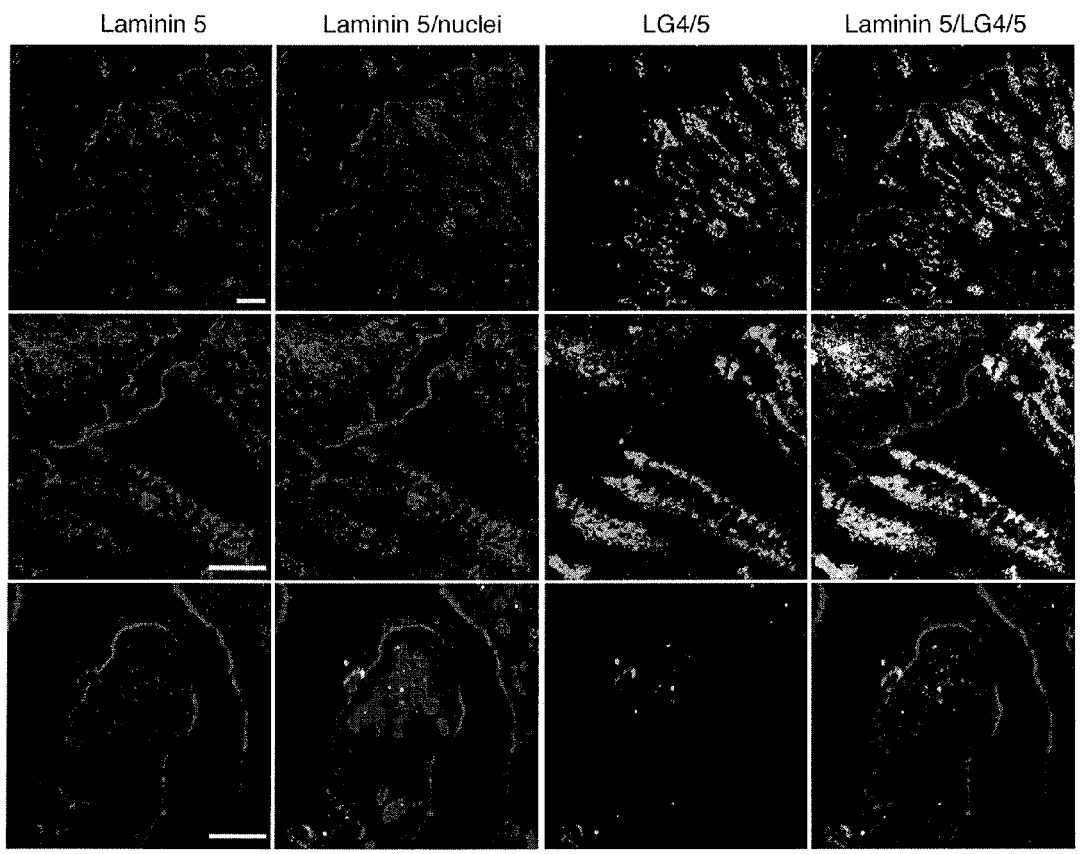

FIG. 12: Expression of the LG4/5 domain of pre-LN5 in normal human colon.

Normal adult human colon tissue sections were purchased from BioChain (Clinisciences, Montrouge, France). After surgery, tissues were immediately frozen in liquid nitrogen. Frozen sections were cut at a thickness of 7 µm and fixed by cold acetone and rehydrated with 10% goat serum in PBS. After washing, sections were incubated 45 min with the 1H12 mAb antibodies, washed in PBS, and incubated an additional 45 min with the anti-LN5 pAb L132, which recognize the processed LN5 trimer. Alexa Fluor 488 and Alexa Fluor 546 antibodies were applied together for 30 min. The Alexa Fluor 488 revealed the staining of the 1H12 mAb against the LG4/5 domain and the Alexa Fluor 546 revealed the staining of the L132 pAb against mature LN5. A 5 min incubation with Syto 59 Red allowed staining of nuclei. Sections were observed by laser scanning confocal microscopy (Zeiss LSM 510). Bars, 100 µm.

Note that LN5 is localized at the basement membrane of epithelial cells and is expressed as a gradient of decreasing intensity from the top to the base of the crypte axis. A faint staining of the LG4/5 domain with the 1H12 mAb was seen exclusively in the epithelial cells located along the edges of the crypte axis but was never expressed at the extracellular level. Merge images revealed that the LG4/5 staining colocalized with the LN5 staining exclusively at the intracellular level in areas where cells are synthesizing pre-LN5. The LG4/5 domain staining was never found in the basement membrane where mature LN5 was found.

Figure 13:
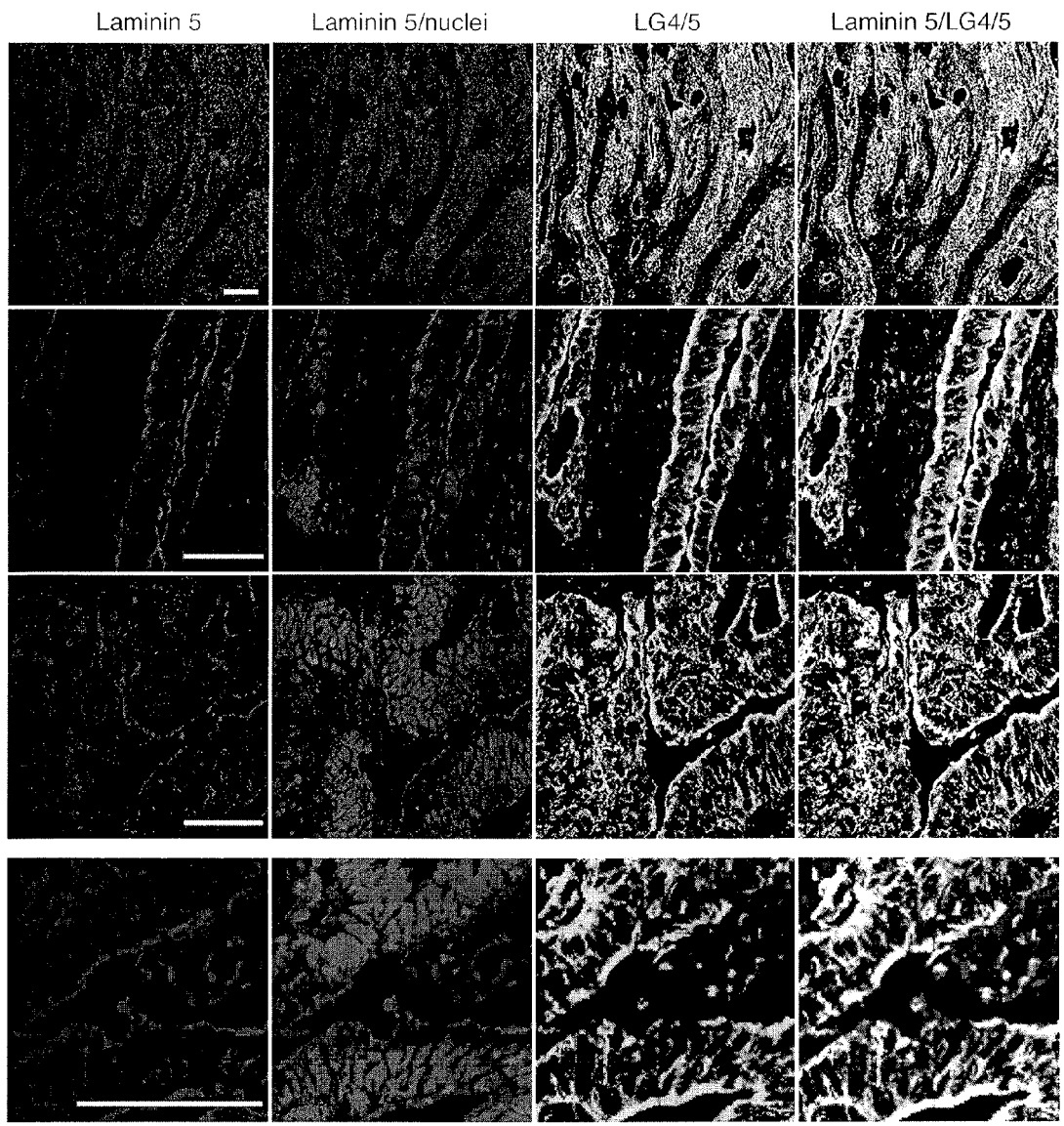

FIG. 13: Expression of the LG4/5 domain of pre-LN5 in human colon carcinoma.

Human colorectal adenocarcinoma were excised from patients who underwent surgery and were purchased from BioChain (Clinisciences, Montrouge, France). After surgery, tissues were immediately frozen in liquid nitrogen. Frozen sections were cut at a thickness of 7 µm and fixed by cold acetone and processed as described in FIG. 12. The Alexa Fluor 488 revealed the staining of the 1H12 mAb against the LG4/5 domain and the Alexa Fluor 546 revealed the staining of the L132 pAb against mature LN5. A 5 min incubation with Syto 59 Red allowed staining of nuclei. Sections were observed by laser scanning confocal microscopy (Zeiss LSM 510). Bars, 100 µm.

Note that basement membrane staining was disorganized and predominant reactivity was found for both mature LN5 and LG4/5 stainings Merge images revealed that the LG4/5 staining often colocalized with the mature LN5 staining at both intra and extracellular levels. Merge images at higher magnification revealed that both the LG4/5 and mature LN5 stainings appeared intense and colocalized in close vicinity of epithelial cells.

Figure 14:
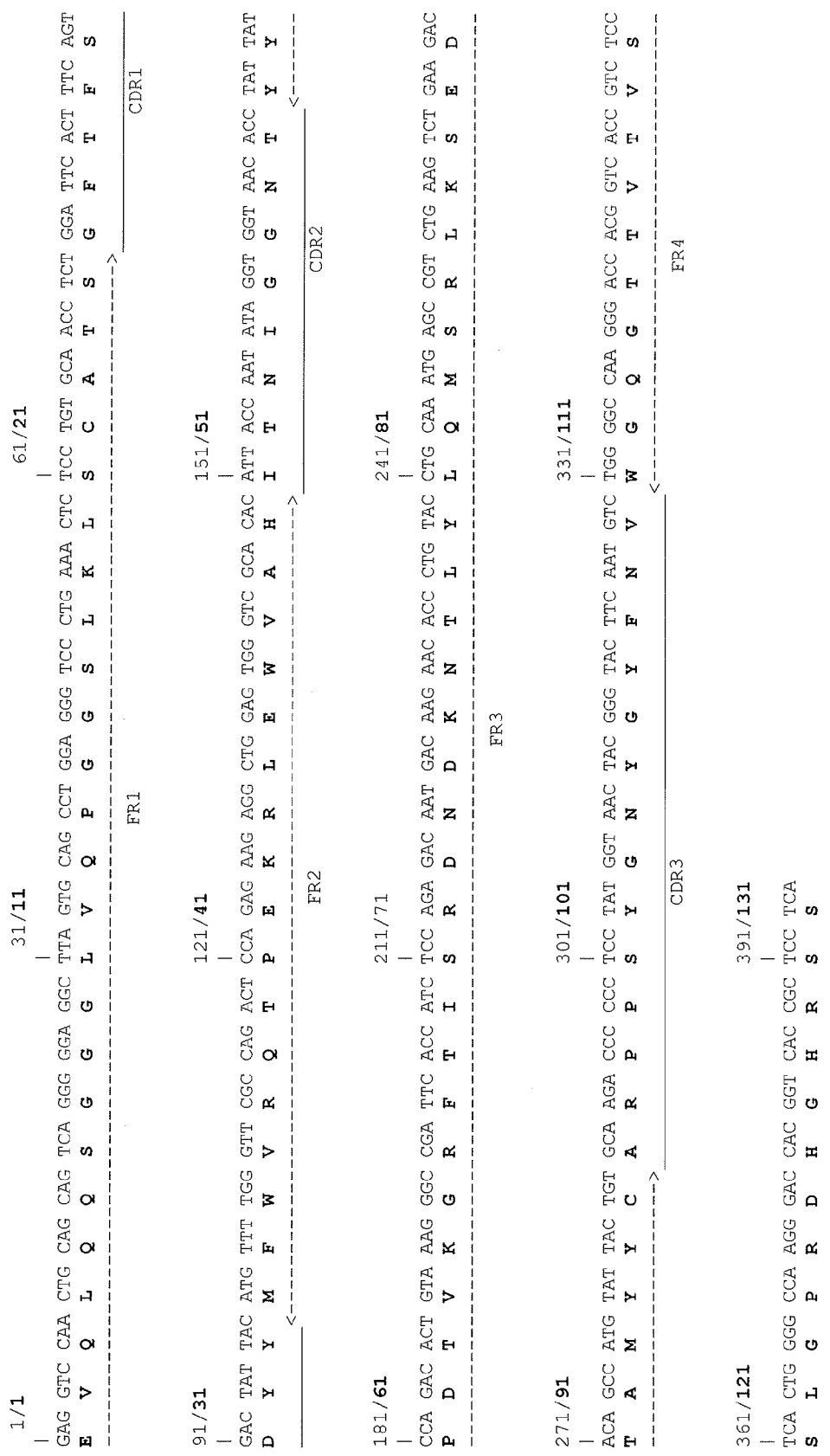
Figure 15:
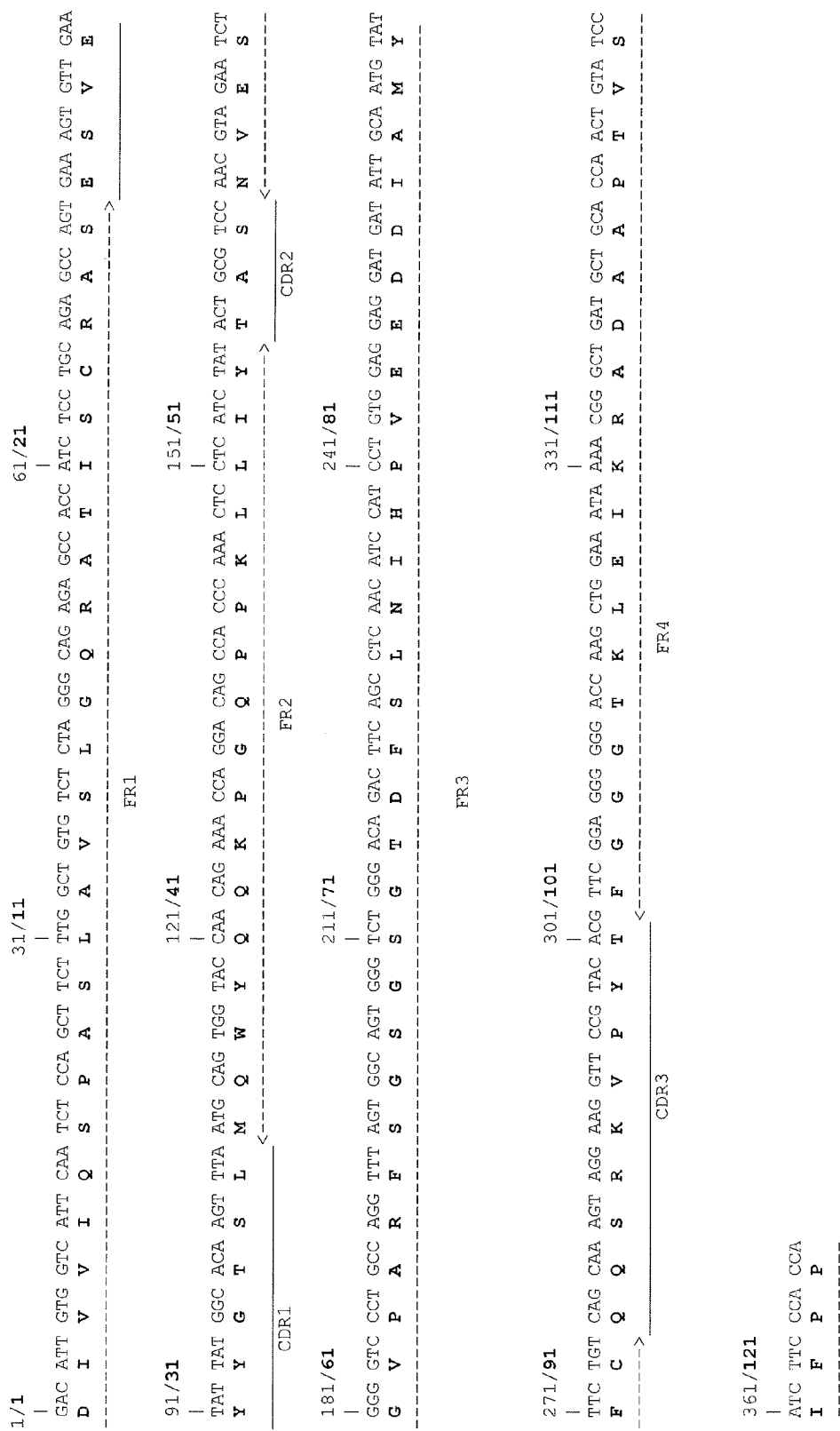

FIGS. 14 and 15: Cloning V domain genes of 3A11

Total RNA was isolated from the hybridoma cells 3 µl using RNeasy Plus (Qiagen, Courtaboeuf, France) according to the manufacturer's recommendations. Cloning of V domains of mouse immunoglobulin heavy chain (VH) and κ light chain genes (VL) was performed by RT-PCR (Titan one tube RT-PCR kit, Roche Diagnostics, Meylan, France) using oligonucleotide primers derived from conserved regions at each end of the cDNA sequences encoding VH and VL domains (Orlandi et al., 1988). For the VH domain, VH-FOR (5'-TGAGGAGACGGTGACCGTGGTCCCTTG-GCCCCAG, SEQ ID NO:13) and VH-BACK (5'-AGGTSM-ARCTGCAGSAGTCWGG, in which S=C or G, M=A or C, R=A or G, and W=A or T; SEQ ID NO:14) primers were used. For the VL domain, VL-FOR primer (5'-GTTAGATCTC-CAGCTTGGTCCC, SEQ ID NO:15) and VL-BACK (5'-GACATTCAGCTGACCCAGTCTCCA, SEQ ID NO:16) were utilised. RT-PCRs were as followed: 42° C., 30 min; 94° C., 2 min; and 40 cycles at 94° C., 30 s; 50° C., 30 s; 68° C., 1 min. PCR fragments were purified on 2% agarose gels, extracted from agarose (QUIAquick; Qiagen) and cloned by TA-cloning (Invitrogen, Cergy Pontoise, France) into pCRII-TOPO. For each PCR fragment, at least three independent clones were sequenced (Genome Express, Meylan, France) and cDNA sequences were compared to the IMGT mouse immunoglobulin data base (http://imgt.cines.fr/). Blast results for VH and VL genes are summarized Table 4 and 5 respectively. Framework regions (FR) and complementary determining regions (CDR) composing VH and VL domains are shown in FIGS. 14 and 15 respectively.

Figure 16:
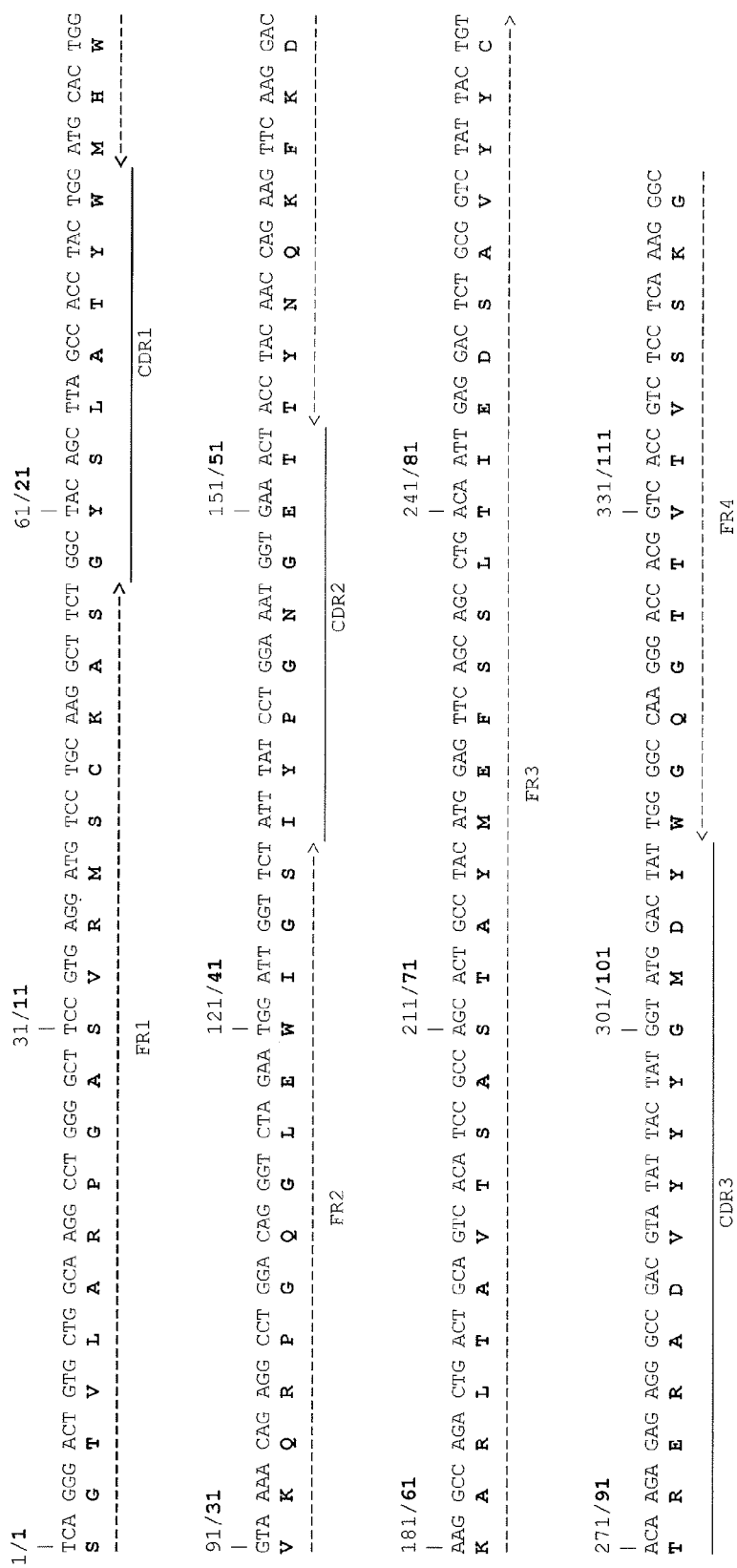
Figure 17:
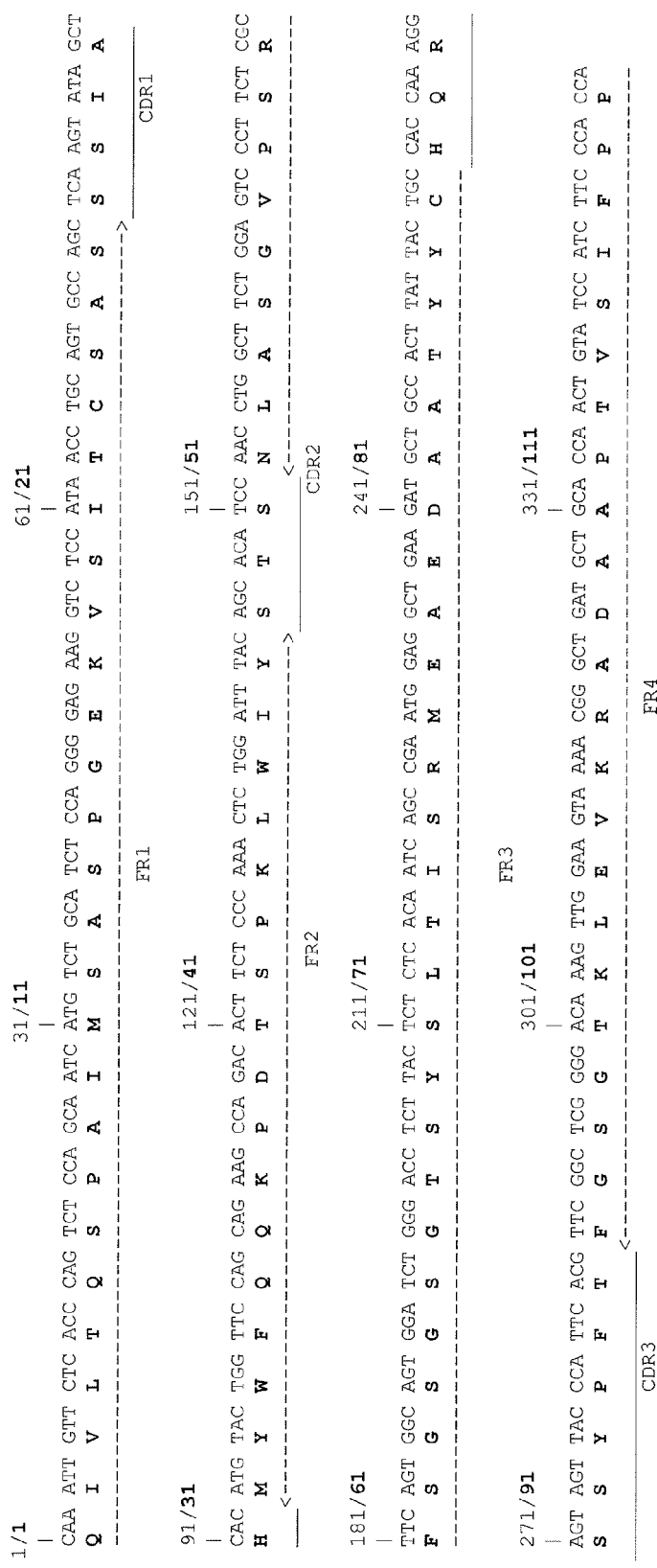

FIGS. 16 and 17: Cloning V domain genes of 15G5

Total RNA was isolated from the hybridoma cells 3A11 using RNeasy Plus (Qiagen, Courtaboeuf, France) according to the manufacturer's recommendations. Cloning of V domains of mouse immunoglobulin heavy chain (VH) and κ light chain genes (VL) was performed by RT-PCR (Titan one tube RT-PCR kit, Roche Diagnostics, Meylan, France) using oligonucleotide primers derived from conserved regions at each end of the cDNA sequences encoding VH and VL domains (Orlandi et al., 1988). For the VH domain, VH-FOR (5'-TGAGGAGACGGTGACCGTGGTCCCTTG-GCCCCAG, SEQ ID NO:13) and VH-BACK (5'-AGGTSM-ARCTGCAGSAGTCWGG, in which S=C or G, M=A or C, R=A or G, and W=A or T; SEQ ID NO:14) primers were used. For the VL domain, VL-FOR primer (5'-GTTAGATCTC-CAGCTTGGTCCC, SEQ ID NO:15) and VL-BACK (5'-GACATTCAGCTGACCCAGTCTCCA, SEQ ID NO:16) were utilised. RT-PCRs were as followed: 42° C., 30 min; 94° C., 2 min; and 40 cycles at 94° C., 30 s; 50° C., 30 s; 68° C., 1 min. PCR fragments were purified on 2% agarose gels, extracted from agarose (QUIAquick; Qiagen) and cloned by TA-cloning (Invitrogen, Cergy Pontoise, France) into pCRII-TOPO. For each PCR fragment, at least three independent clones were sequenced (Genome Express, Meylan, France) and cDNA sequences were compared to the IMGT mouse immunoglobulin data base (http://imgt.cines.fr/). Blast results for VH and VL genes are summarized Table 6 and 7 respectively. Framework regions (FR) and complementary determining regions (CDR) composing VH and VL domains are shown in FIGS. 16 and 17 respectively.

Figure 18:
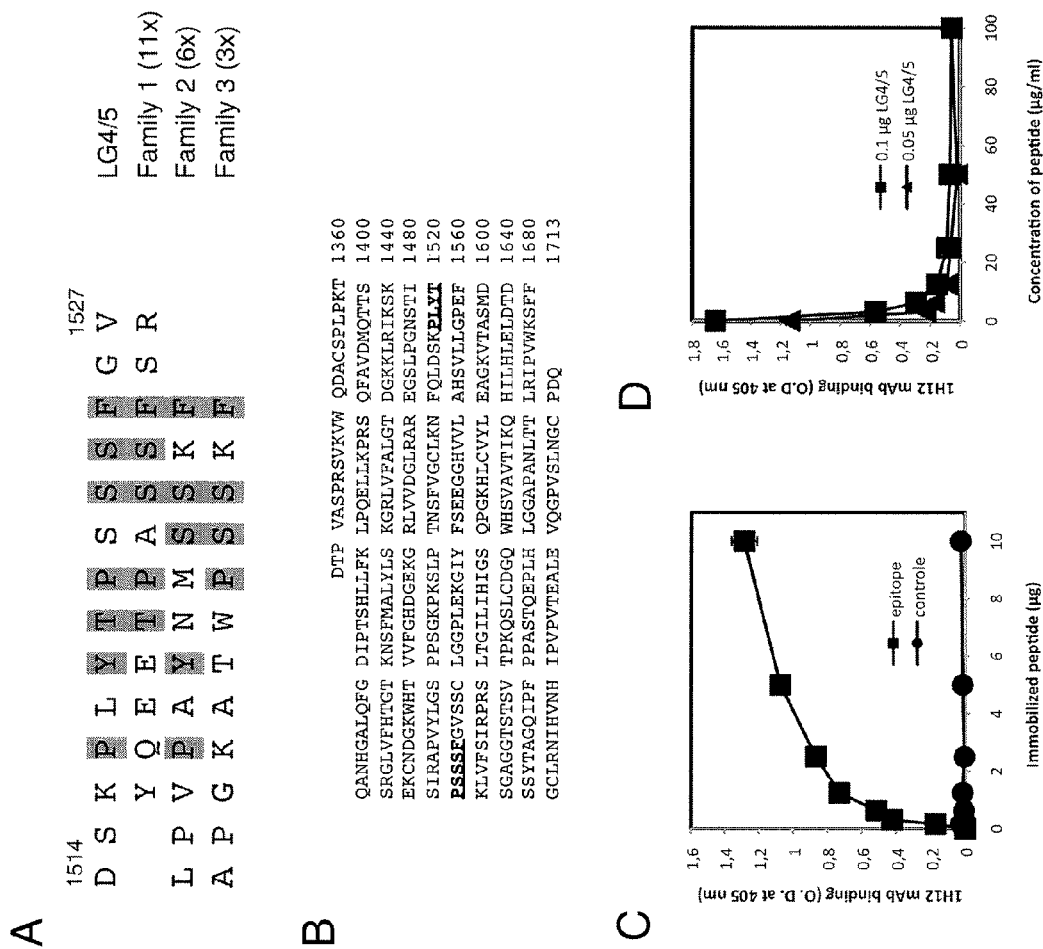

FIG. 18: Epitope mapping of the 1H12 mAb (A) Epitope mapping of the 1H12 mAb. To determine the epitope of the 1H12 mAb, a commercial phage display peptide library based on a combinatorial library of random peptides 12-mers fused to a minor coat protein (pIII) of M13 phage (Ph.D-12 phage display peptide library; New England Biolabs, Ipswich, Mass., USA) was screened according to the manufacturer's recommendations. Briefly, $1.5 \times 10^{11}$ phages were incubated with 1.5 µl of 1H12 mAb liquid ascites for 20 min in TBST buffer (50 mM Tris-HCl pH8.5, 150 mM NaCl, 0.1% Tween 20), and then 50 µl of protein A or protein G Sepharose beads were added. After 15 min of incubation, beads were washed 10 times in TBST buffer and bound phages eluted with 0.2 M Glycine-HCl pH2.2. After neutralization with 1 M Tris-HCl pH9.1, phages were amplified and the phage capture procedure was repeated. After four rounds of phage selection, at least 20 individual phages were sequenced and a consensus sequence was determined. Comparison with the LG4/5 sequence allowed to identify the 1H12 mAb epitope. (B) The 1H12 mAb epitope is shown within the entire LG4/5 sequence (C) The 1H12 mAb recognizes the LDSKPLYTPSSSF epitope. A synthetic peptide encompassing the 1H12 mAb epitope with sequence LDSKPLYTPSSSF (SEQ ID NO: 25) (■) as well as a control peptide corresponding to another sequence in the LG4/5 domain but different from the epitope (●) were synthesized (Eurogentec, Anger, France) and used for ELISA assays. Multiwell plates (Greiner, Dutscher, Brumath, France) were coated with the indicated quantities of peptides by overnight adsorption at 4° C. After saturation of the wells with 1% BSA, wells were incubated with the 1H12 mAb (50 µg/ml) for 1 h at 22° C. followed by a typical enzyme-immunoassay reaction with peroxidase conjugate of goat anti-mouse immunoglobulin as second antibody and 2,2'-azino-bis(3-ethyl-benthiazoline-6-sulfonic acid) as the chromogenic substrate. Color yields determined at 405 nm in an ELISA reader (MR 5000, Dynatech Labs., UK) revealed that the 1H12 mAb binds to the LDSKPLYTPSSSF peptide in a dose dependent and specific manner. Each point represents the average of triplicate wells of which blank values corresponding to non-specific binding of the 1H12 mAb were subtracted. (D) The LDSKPLYTPSSSF peptide inhibits binding of the 1H12 mAb to the LG4/5 fragment. Multiwell plates were coated with either 0.1 µg (■) or 0.05 µg (▲) LG4/5 by overnight adsorption at 4° C. After saturation of the wells with 1% BSA, 100 µl of the indicated concentrations of peptides were added to the wells prior to the 1 h incubation of a 50 µg/ml solution of the 1H12 mAb. After washes, the enzyme-immunoassay reaction performed as described above revealed that the LDSKPLYTPSSSF peptide was able to compete in a dose dependent manner with the 1H12 binding site in the LG4/5 fragment.

Figure 19:
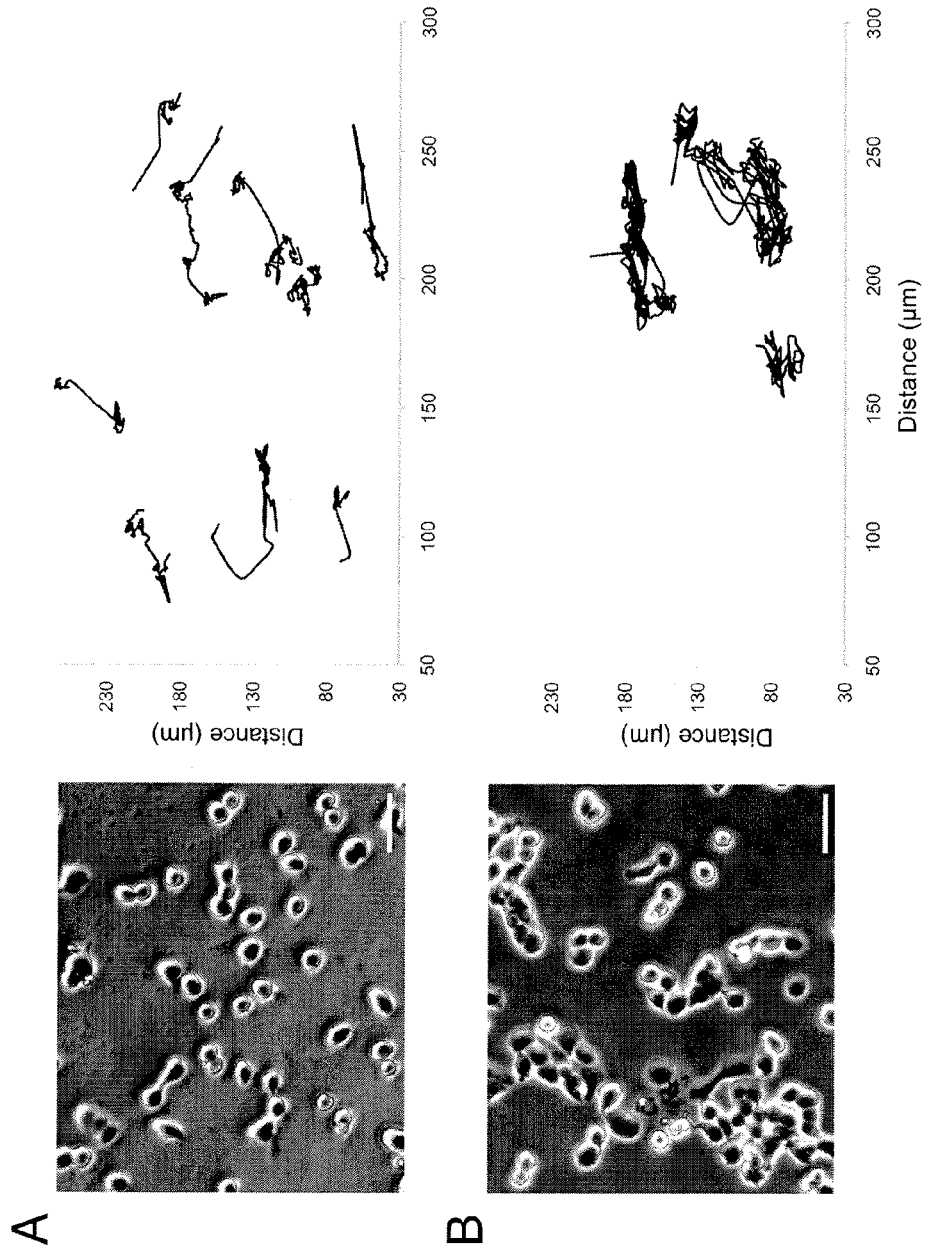

FIG. 19: Effect of the 1H12 mAb on cultured colon carcinoma HT29 cells.

Colon carcinoma HT29 cells ($8 \times 10^3$) were plated in 24 well plates in DMEM containing 10% FCS. After 2 h at 37° C., the medium and non adhered cells were removed and replaced with either serum-free DMEM (A) or serum-free DMEM containing 100 pmole/ml of 1H12 mAb (B). Cell behavior was monitored at 30 min intervals over a period of 40 h at 37° C. in a humidified atmosphere containing 5% CO2 using an Axiovert 100M Zeiss microscope equipped with a CCD camera. An image of one field in each condition at the end of the recording shows that cells have behaved differently depending on the absence or presence of the antibody. In the absence of antibody (A), cells spread or migrated over variable distances and always remained independent. In the presence of the 1H12 mAb (B), either cells instantly detached from the plate and died or had a tendency to move over short distances toward other cells and aggregate. This experiment was repeated by plating cells on extracellular matrix substrates such as fibronectin and collagen I and produced the same result (data not shown) suggesting that this effect is independent of the substrate. Plots of cells showing positions for 10 cells in one field for each condition were achieved using the tracking software Metaview (Roper Scientific, Princeton Instruments, Evry, France). Distance migrated in micrometers is indicated on the plots. Bar, 50 µm.

Figure 20:
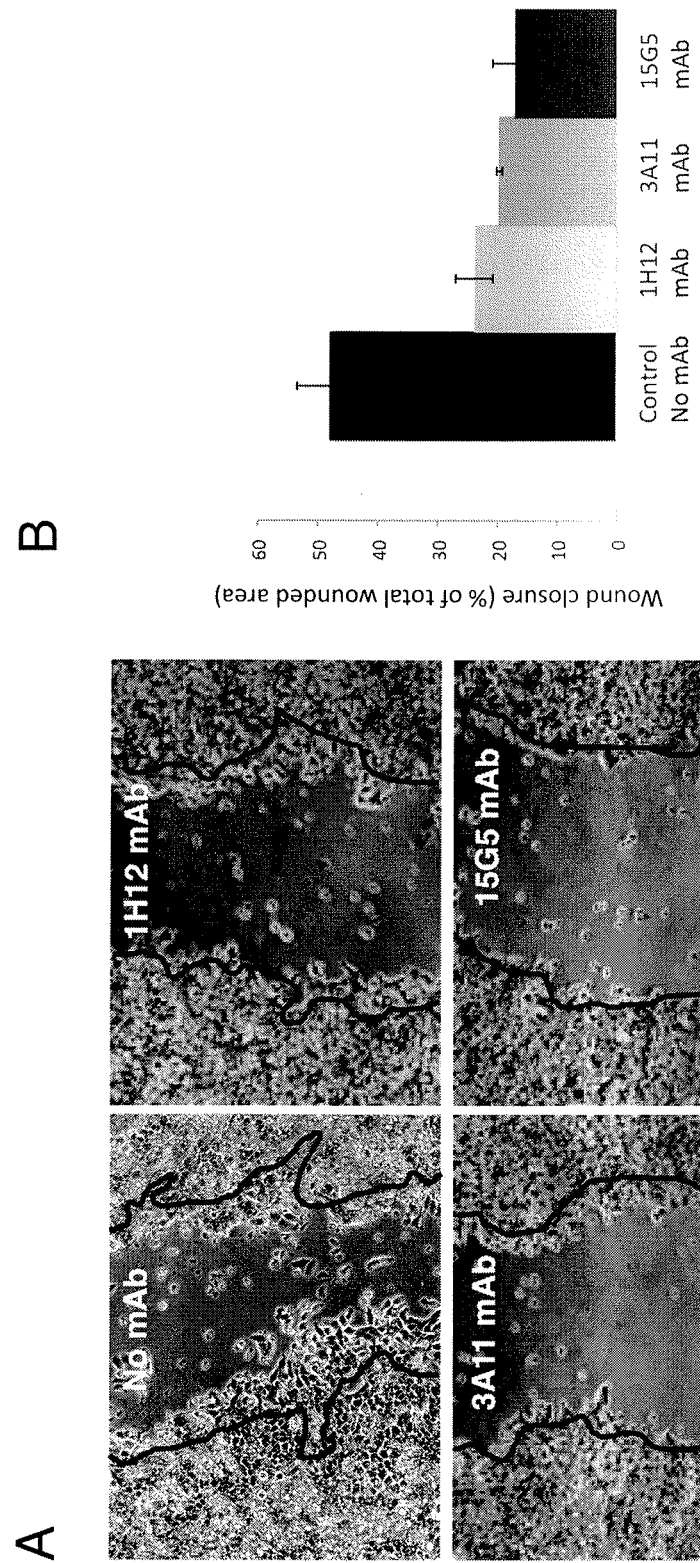

FIG. 20: Effect of 1H12, 3A11 and 15G5 mAbs in colon carcinoma HT29 cells wound closure assay.

Human colon adenocarcinoma HT29 cells were grown at confluency in 24 well tissue culture plates in DMEM containing 10% FCS. Medium was removed and the cell layer was scraped with a pipette tip. The scrape-wounded surface were washed with PBS and incubated in DMEM with 2% FCS at 37° C. in the absence (no mAb), or presence of 100 pmole/ml of mAb 1H12, 3A11 and 15G5 mAbs. Cell behavior was monitored at 2 h intervals over a period of 46 h at 37° C. in a humidified atmosphere containing 5% CO2 using an Axiovert 100M Zeiss microscope equipped with a CCD camera. (A) Images taken at the beginning and at the end of the recording in each well allowed to define the total surface covered by the cells in the time allowed (black lines represent the wound edges at the beginning of the recording). Bar, 100 µm. (B) Surface areas at the various time points were quantified for each well using Adobe Photoshop CS3 Extended (version 10.0) software and the final wounded closure is represented as the percent of the total wounded area. Each assay point was derived from triplicate measurements (3 wells per assay point). The data, which are representative of three independent experiments, shows that the 3 mAbs have the capability to inhibit the migration and closure of the carcinoma HT29 cells.

Figure 21:
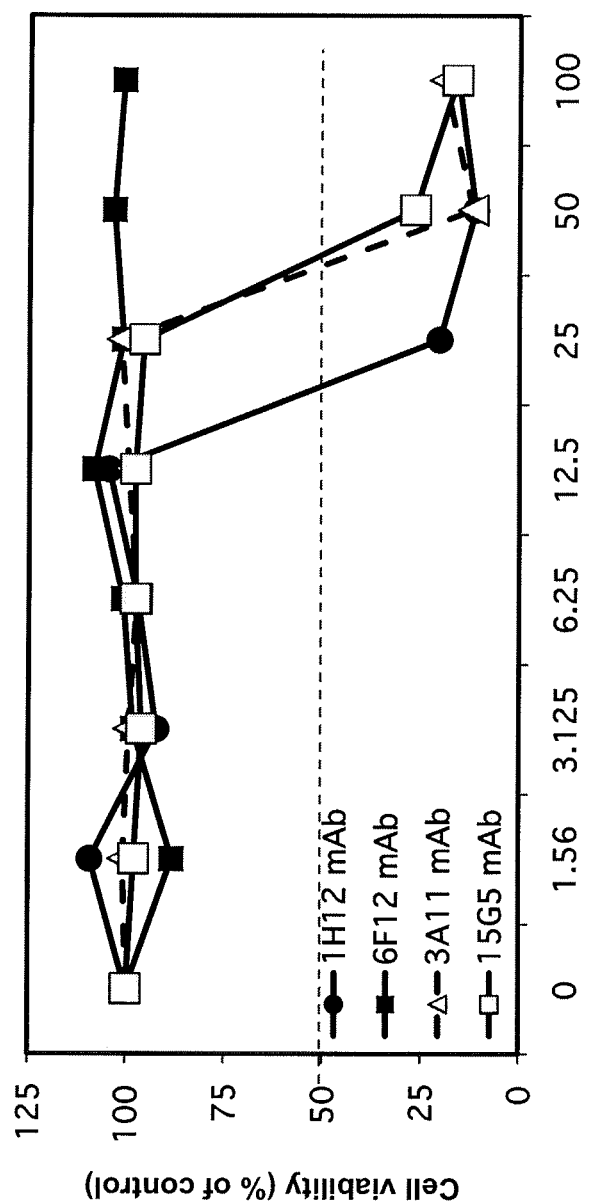

FIG. 21: Effect of the 1H12, 3A11 and 15G5 mAbs on colon carcinoma cell growth in vitro.

Human colon adenocarcinoma HT29 cells (American Type Culture Collection, HTB-38) were plated in 96 well plates ($8 \times 10^3$ cells/well) in Dulbecco's modified Eagle medium (DMEM) containing 10% FCS and additives including 2 mM Glutamax (Gibco, Invitrogen, Cergy Pontoise, France). Two days after, medium was removed and replaced with DMEM 2% FCS, 2 mM Glutamax containing increasing concentrations of either 1H12 mAb (●), the 3A11mAb (Δ), the 15G5 mAb (□) or the 6F12 mAb control against the LN5 beta3 chain (■). This step was repeated 3 times and after 2 additional days in culture, the medium was removed and quantitation of living cells was determined using the Cell proliferation kit II (XTT, Roche Molecular Biomedicals).

Figure 22:
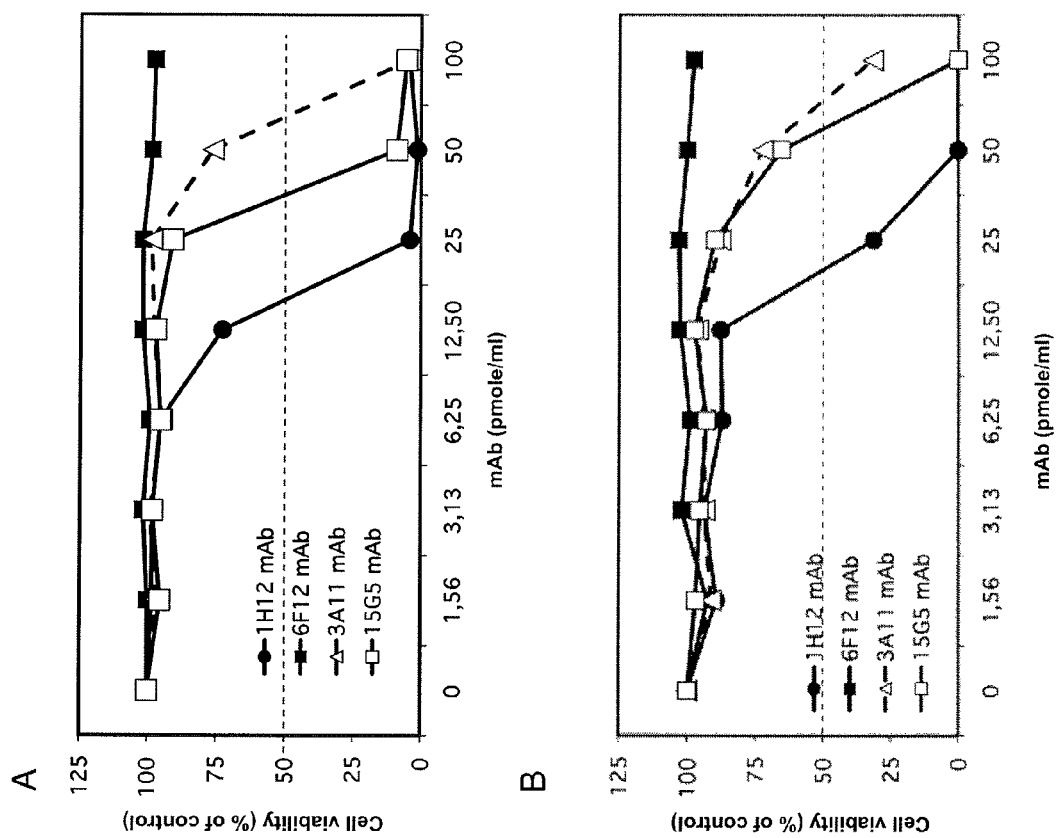

FIG. 22: Effect of the 1H12, 3A11 and 15G5 mAbs on breast carcinoma cell growth in vitro.

(A) Breast adenocarcinoma MCF7 cells (American Type Culture Collection, HTB-22) were plated in 96 well plates ($8 \times 10^3$ cells/well) in Dulbecco's modified Eagle medium (DMEM) containing 10% FCS and additives including 2 mM Glutamax (Gibco, Invitrogen, Cergy Pontoise, France). Two days after, medium was removed and replaced with DMEM 2% FCS, 2 mM Glutamax containing increasing concentrations of either 1H12 mAb (●), the 3A11mAb (Δ), the 15G5 mAb (□) or the 6F12 mAb control against the LN5 beta3 chain (■). This step was repeated 3 times and after 2 additional days in culture, the medium was removed and quantitation of living cells was determined using the Cell proliferation kit II (XTT, Roche Molecular Biomedicals). (B) Breast adenocarcinoma MDA-MB-231 (American Type Culture Collection, HTB-26) were plated in 96 well plates ($8 \times 10^3$ cells/well) in Dulbecco's modified Eagle medium (DMEM) containing 10% FCS and additives including 2 mM Glutamax (Gibco, Invitrogen, Cergy Pontoise, France). Two days after, medium was removed and replaced with DMEM 2% FCS, 2 mM Glutamax containing increasing concentrations of either 1H12 mAb (●), the 3A11mAb (Δ), the 15G5 mAb (□) or the 6F12 mAb control against the LN5 beta3 chain (■). This step was repeated 3 times and after 2 additional days in culture, the medium was removed and quantitation of living cells was determined using the Cell proliferation kit II (XTT, Roche Molecular Biomedicals).

Figure 23:
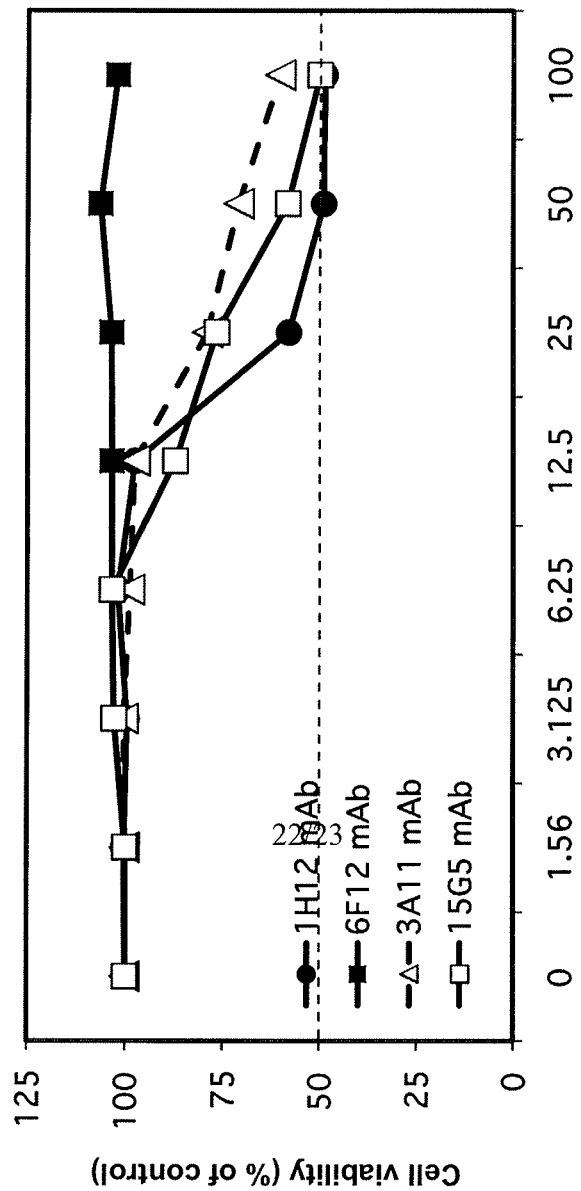

FIG. 23: Effect of the 1H12, 3A11 and 15G5 mAbs on ovary adenocarcinoma cell growth in vitro.

Human ovary adenocarcinoma NIH-OVCAR-3 cells (American Type Culture Collection, HTB-161) were plated in 96 well plates ($8 \times 10^3$ cells/well) in Dulbecco's modified Eagle medium (DMEM) containing 10% FCS and additives including 2 mM Glutamax (Gibco, Invitrogen, Cergy Pontoise, France). Two days after, medium was removed and replaced with DMEM 2% FCS, 2 mM Glutamax containing increasing concentrations of either 1H12 mAb (●), the 3A11mAb (Δ), the 15G5 mAb (□) or the 6F12 mAb control against the LN5 beta3 chain (■). This step was repeated 3 times and after 2 additional days in culture, the medium was removed and quantitation of living cells was determined using the Cell proliferation kit II (XTT, Roche Molecular Biomedicals).

Figure 24:
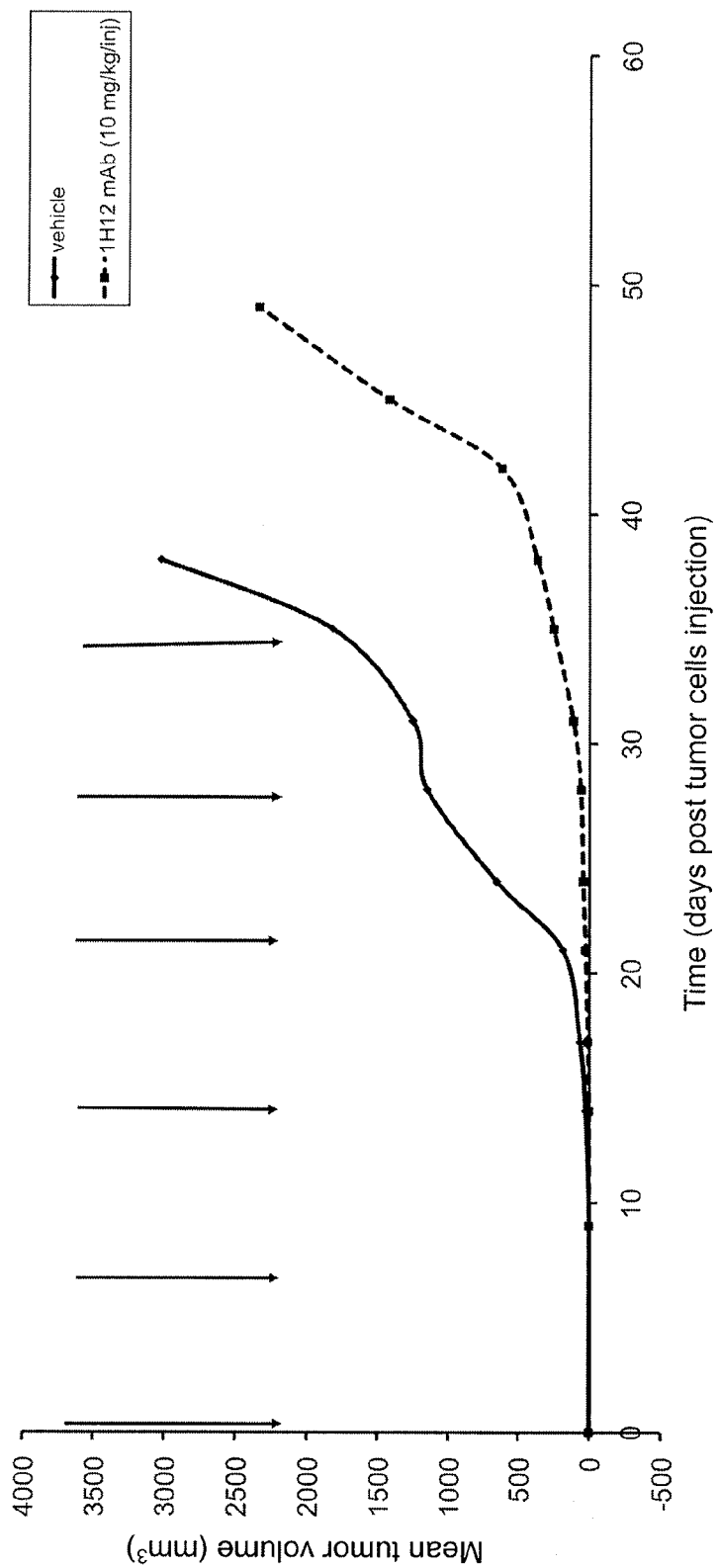

FIG. 24: Anti-tumor activity of the 1H12 mAb in mice bearing subcutaneous human breast tumors.

Two millions breast adenocarcinoma MDA-MB-231 cells were injected subcutaneously into the dorsal flank of immunodeficient SCID mice (Paine-Murrieta et al., 1997). Treatment groups included a control group of ten mice receiving the vehicle (saline buffer) and a second group of ten mice received treatment (one injection at the day following injection of tumor cells and weekly treatments thereafter at a concentration of 10 mg/kg/injection) with the 1H12 mAb. The tumor volume was evaluated and calculated weekly as (length X(width)2)/2 for each group. Mice were maintained under pathogen-free conditions in facilities approved by Accreditation of Laboratory Animal Care and in accordance with current regulations and standards of the French Department of Agriculture. Tolerance studies were beforehand performed on 3 groups of ten healthy mice receiving one IP injection of either vehicle or 1H12 mAb at 10 mg/kg/inj or 1H12 mAb at 50 mg/kg/inj twice a week for two consecutive weeks. Body weight determination from Day 0 to Day 17 revealed that no sign of toxicity was noticed.

EXAMPLES

Example 1

Method of Preparation of Monoclonal Antibodies Directed to LN5 Alpha3 LG4/5 Domain Inhibiting the Interaction Between this Domain and Syndecan-1

The inventors have recombinantly expressed the human alpha3LG4/5 fragment. They have also identified the heparan sulfate proteoglycan receptor syndecan-1 from normal human skin keratinocytes (NHK) and other epithelial cells as a receptor for this fragment (Okamoto et al. 2003).

LN5 is known for its role in promoting carcinoma cell migration, notably those with malignant characteristics, and may act as a ligand for invasiveness (Miyazaki K. 2006). However, it is not known whether the interaction between LN5 alpha3 LG4/5 domain and syndecan-1 is involved in malignant process. The inventors decided to address this question by providing specific inhibitors of this interaction.

In order to develop inhibitors of the LG4/5 domain and specifically block the syndecan-1 mediated interaction with pre-LN5, the inventors have raised mouse monoclonal antibodies against the LG4/5 fragment.

The method used for generating such monoclonal antibodies was the following:

In an attempt to develop new anti-tumour agents, a strategy to select antibodies that specifically inhibit syndecan-1 mediated cell adhesion to the LG4/5 fragment was developed. The strategy is based on a specific syndecan-1 mediated cell adhesion assay in which cells adhesion is only due to the recognition of LG4/5 fragment by syndecan-1 expressed at the surface of target cells.

To raise monoclonal antibodies to LG4/5, two female BALB/c mice were immunized with 100 μg of purified recombinant LG4/5 emulsified in complete Freund's adjuvant. Three, 6, 9 and 12 weeks later, mice were boosted with 100, 50, 50 and 50 μg of immunogen respectively. A test bleed followed by an enzyme-linked immunosorbent assay (ELISA) was performed and allowed to choose the most productive mouse. A final pre-fusion boost of 10 μg of immunogen was done at the $14^{th}$ week and spleen cells were fused with the myeloma cell line SP2/OAG14 using polyethylene glycol according to standard protocols. Viable hybridomas were selected and screened for the production of antigen specific antibodies by ELISA. All selected hybridoma supernatants were then tested for their potential capacity to inhibit the syndecan-1 mediated adhesion to the LG4/5 fragment. A specific cell adhesion assay was therefore developed with the fibrosarcoma cell line HT1080 (American Type Culture Collection, CCL-121), which express a high level of the receptor syndecan-1 (Okamoto et al., 2003). The experimental procedure was as follow.

Multiwell plates were coated with 0.2 μM of purified recombinant LG4/5 by overnight adsorption at 4° C. After saturation of the wells with 1% bovine serum albumin (BSA), hybridoma supernatants were applied (100 μL/well) for 2 h to allow the antibodies to bind to the LG4/5 fragment and potentially block the cell binding site. During that period of time, cultured HT1080 cells were detached with 5 mM EDTA-PBS, immediately rinsed in serum-free medium and counted.

Hybridoma supernatants were removed, the wells were rinsed with PBS and 8×10⁴ cells were seeded per well. A 100% inhibitory control was performed in each plate, by incubating LG4/5 coated wells with 50 pmole/ml of heparin (heparin from porcin intestinal mucosa, Sigma, Saint-Quentin Fallavier, France), which is known to bind to the heparan sulfate proteoglycan syndecan-1 binding site in the LG4/5 fragment (Okamoto et al., 2003). After 30 min to 1 h at 37° C., plates were washed with PBS to remove non-adherent cells and fixed with 1% glutaraldehyde in PBS. The extent of adhesion was determined after staining with 0.1% crystal violet and absorbance measurements at 570 nm after solubilisation. A blank value corresponding to BSA-coated wells (<5% of maximal cell adhesion) was automatically subtracted. Each point was derived from the average of triplicate determinations. Inhibition of adhesion in the presence of either heparin or the hybridoma supernatants was expressed as a percent of the control without inhibitor. Among all hybridoma supernatants tested, 3 clones (1H12, 3A11 and 15G5) produced a total inhibition of HT1080 cell adhesion to the LG4/5 fragment. Further cell adhesion analysis revealed that 1H12 was the most efficient function-blocking clone. The selected colonies were cloned by limiting dilution and gave rise to the 1H12f1h5 clone, namely adhesio-mAb. The 3A11 and 15G5 clones gave rise to the 3A11f7e6 and the 15G5b11e5 clones respectively. Antibody were collected from selected hybridoma clones either in the form of spent tissue culture medium or as ascites from BALB/c×A/J hybrid mice, pristane primed, and injected with at least 10⁷ hybridoma cells. The isotype of the 3 clones were determined: the 1H12f1h5 clone is an IgG1 Kappa, the 3A11f7e6 clone is an IgG1 Kappa, the 15G5b11e5 clone is an IgG1 Kappa.

The cDNAs encoding the LVCR and HVCR of each clone were isolated, cloned and sequenced. The resulting sequences are shown in FIGS. 1, 2, 14, 15, 16 and 17.

Identification of a Monoclonal Antibody Directed to LN5 Alpha3 LG4/5 Domain Inhibiting the Interaction Between this Domain and Syndecan-1

Figure 2:
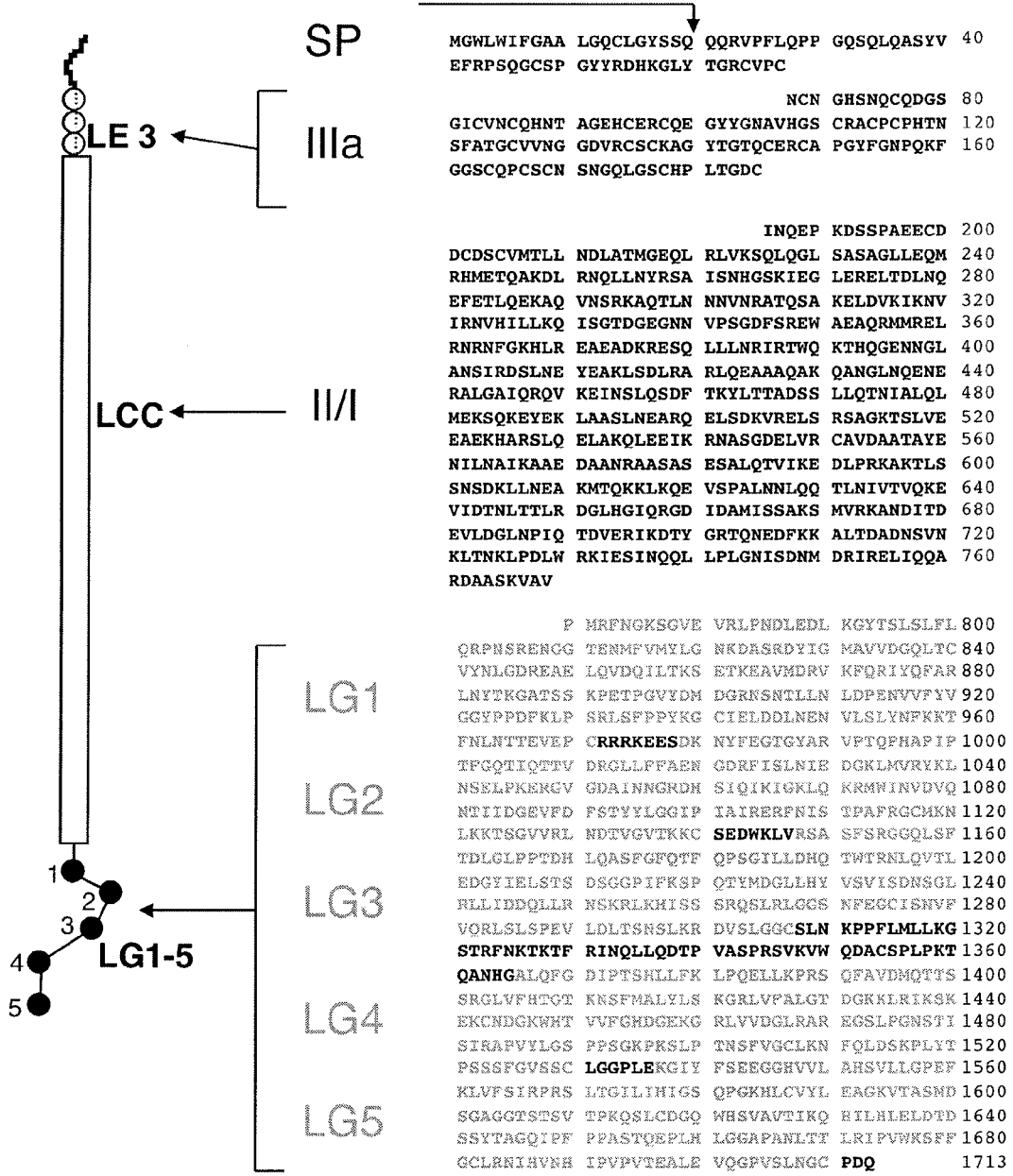
FIG. 2: Sequence of the alpha3 chain and composition of the LG domain The sequence of the human LN alpha3 chain is shown. The various domains within the chain are listed and their localization is shown. SP, signal peptide; LE, laminin epidermal growth factor like domain; LCC, laminin coiled-coil; LG1-5, laminin globular domains LG1, LG2, LG3, LG4 and LG5.

Preliminary experiments have revealed that one of the antibodies (1H12 mAb, produced by the hybridoma cell line named 1H12 deposited on Jan. 8, 2008 at the Collection Nationale de Cultures de Microorganismes (C.N.C.M.), INSTITUT PASTEUR, 25 rue du Docteur Roux, F-75724 PARIS Cedex 15, FRANCE) obtained in Example 1 specifically inhibits adhesion of the HT1080 fibrosarcoma cells to the LG4/5 fragment in a manner comparable to the positive control heparin (FIG. 2).

Figure 4:
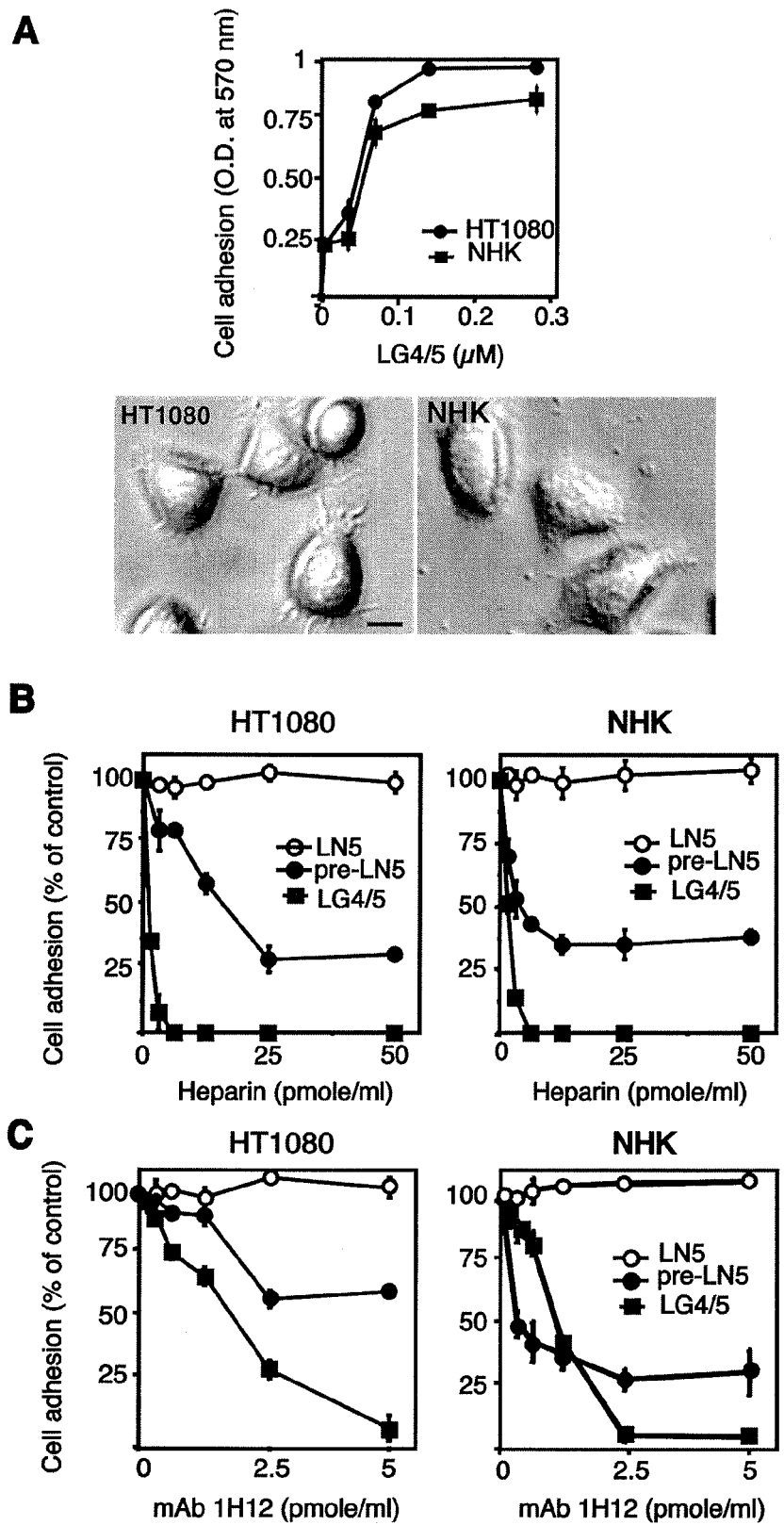
FIG. 4: The 1H12 mAb inhibits syndecan-1 mediated cell adhesion to the LG4/5 fragment (A) Dose-dependent syndecan-1 mediated cell adhesion of HT1080 cells and NHK to the alpha3LG4/5 fragment. Multiwell plates were coated with recombinantly expressed LG4/5 fragment as indicated. After saturation with 1% BSA, EDTA-released HT1080 cells and NHK were seeded ($8\times10^4$ cells/well) and incubated for 30 min to 1 hour. Non-adhered cells were washed with PBS and the extent of adhesion was determined after fixation of adherent cells, followed by staining with 0.1% crystal violet, and absorbance measurement at 570 nm. A blank value corresponding to BSA-coated wells was substracted and each assay point was derived from triplicate measurements. Spreading patterns of HT1080 cells and NHK adhered to alpha3LG4/5 through their receptor syndecan-1 as observed with an Axiovert 40 Zeiss microscope equipped with a PlasDIC filter. Bar, 10 µm. (B) Effect of soluble heparin on adhesion of EDTA-released HT1080 cells and normal human keratinocytes to pre-LN5 (5 nM), mature LN5 (5 nM) and the LG4/5 fragment (0.3 µM). After saturation with 1% BSA, the wells were incubated with the indicated concentration of heparin for 1 h at room temperature, and the cells were seeded in the presence of the same concentration of heparin. (—C) Effect of the 1H12 mAb on adhesion of EDTA-released HT1080 cells and NHK to pre-LN5 (5 nM), mature LN5 (5 nM) and the LG4/5 fragment (0.3 µM). After saturation with 1% BSA, the wells were incubated with the indicated concentration of the 1H12 mAb at room temperature. (B and C) HT1080 cells and NHK were seeded at a density of $8\times10^4$ for 1 h. In all cases, the extent of cell adhesion was determined as described above and expressed as a percentage of adhesion in the absence of competitor.

The inventors have previously shown that cell adhesion to alpha3LG4/5 fragment is mediated by the heparan sulfate proteoglycan (HSPG) receptor syndecan-1 and that integrins are not involved (Okamoto et al. 2003; Bachy et al., 2008; FIG. 4A). Indeed, as shown in FIG. 4B, heparin, which binds to HSPG, strongly inhibited NHK and HT1080 cell adhesion to the alpha3LG4/5 fragment alone (Okamoto et al. 2003), and partially inhibited cell adhesion to pre-LN5 while it had no effect on adhesion to mature LN5.

Furthermore, the anti-LG4/5 antibody (1H12 mAb), totally prevented NHK and HT1080 cell adhesion to alpha3LG4/5, suggesting that this antibody interferes with the epitope involved in syndecan-1 interaction. Pre-incubation of pre-LN5 and mature LN5 substrate coats with 1H12 mAb partially prevented cell adhesion to pre-LN5 and had no effect, as expected, on cell adhesion to mature LN5. These results demonstrate that 1H12 mAb blocks syndecan-1 mediated adhesion to the LG4/5 domain without affecting integrin mediated adhesion to the mature LN5. This suggests that the 1H12 antibody will selectively target the alpha3LG4/5 domain in pre-LN5 to inhibit human carcinoma tumorigenesis without disrupting mature LN5 adhesive function in normal tissues.

Figure 5:
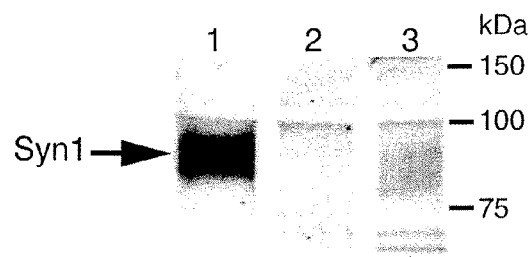
FIG. 5: The 1H12 mAb blocks the syndecan-1 binding site in the LG4/5 domain.

To further establish that 1H12 mAb blocks the syndecan-1 binding to the LG4/5 domain, the inventors performed pull-down experiments of syndecan-1 from cell lysates (FIG. 5). Capture of syndecan-1 was carried out by incubating NHK or HT1080 cell lysates with beads that were covalently covered with the LG4/5 fragment. Treatment of the HSPG-receptor with heparitinase I and chondoitinase ABC followed by immunoblotting with an antibody against syndecan-1 specifically revealed a band corresponding to the syndecan-1 core protein in the material bound to LG4/5 (lane 1). As expected, heparin, which binds to the HSPG binding site, prevented syndecan-1 binding to the LG4/5 beads (lane 2). The anti-LG4/5 1H12 mAb also prevented syndecan-1 binding, thus confirming the previous findings that it is a function-blocking antibody.

Example 2

Effect of 1H12 mAb on Cell Migration and Cancer Cells

Figure 3:
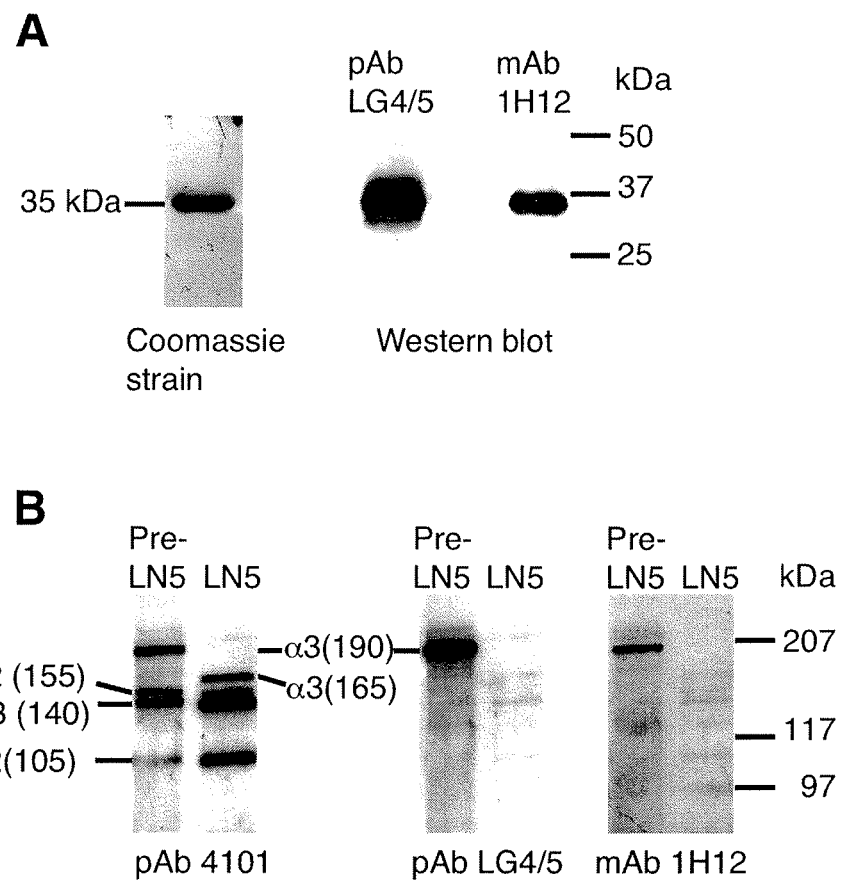
FIG. 3: The 1H12 mAb is specific for the alpha3LG4/5 domain of pre-LN5 (A) SDS-PAGE and immunoblot analysis of the purified recombinant LG4/5 fragment. As previously described (Okamoto et al., 2003) the recombinant LG4/5 fragment was affinity-chromatographed on an Heparin column and 2 µg of the pure eluted protein was resolved by 12% SDS-PAGE under non-reducing conditions. The protein was stained with Coomassie Brilliant Blue R-250 or transferred to nitrocellulose followed by immunodetection with either the pAb against LG4/5 or the mAb 1H12 as annotated. The migration positions of molecular weight markers are shown on the right. (B) SDS-PAGE and Western blot analysis of pre-LN5 purified from keratinocyte culture media. As previously documented (Bachy et al., 2008), pre-LN5 and LN5 were affinity purified from keratinocyte culture medium and 1 µg of each protein was analysed by 8% SDS-PAGE under reducing conditions. Immunoblot analysis were performed with the anti-alpha3,beta3gamma2 pAb 4101 (Rousselle et al., 1991), the anti-LG4/5 pAb and the anti-LG4/5 mAb 1H12 as indicated. Molecular masses of the LN5 and pre-LN5 subunits and markers are annotated.

Western blotting experiments using 1H12 mAb revealed that it specifically recognizes the LG4/5 fragment. In addition, this antibody binds specifically to the precursor form of the alpha3 chain while no binding was found to the mature form of alpha3 lacking the LG4/5 domain (FIG. 3). Indeed, epitope mapping experiments showed that the 1H12 monoclonal antibody specifically recognizes the peptide of sequence LDSKPLYTPSSSF (SEQ ID NO: 25) located in the LG4 domain (FIG. 18). This is confirmed by competition experiments showing that binding of LG4/5 to 1H12 is lost when a synthetic peptide of sequence: LDSKPLYTPSSSF (SEQ ID NO: 25) is added (FIG. 18).

As pre-LN5 was shown to be specifically and highly expressed by leading and migrating keratinocytes localized at the edges of wounds closure (Ryan et al. 1994; Goldfinger et al., 1999), the LG4/5 fragment in pre-LN5 could be involved in migration.

To test this hypothesis, the inventors assessed the effect of 1H12 mAb, which inhibits the interaction between LG4/5 and syndecan-1, in a NHK wound assay. Scrape wounds were introduced into confluent NHK culture and then allowed to heal for 16 h in the presence of the appropriate antibody. Wounds in cell populations incubated without antibody healed completely within the experimental frame (FIG. 6B). When 1H12 mAb was added to the wounded cultures (FIG. 6C), healing was completely inhibited. Interestingly, similar results were obtained with the 1H12, 3A11 and 15G5 antibodies using colon carcinoma cells (FIG. 20), thus reinforcing the statement that the LG4/5 fragment/syndecan-1 interaction plays a major role in epithelial cell migration.

These in vitro and in cellulo experiments clearly show that the syndecan-1 interaction with the LG4/5 domain in pre-LN5 plays a role in cell migration.

Many immunohistochemical studies have shown that LN5 or its subunits are highly expressed in various types of human cancers. In particular, the LN5 γ2 chain has been shown to be expressed in tumor cells at the invasion front or in budding tumor cells in many types of human cancers such as adenocarcinomas of the colon, breast, pancreas and lung, squamous cell carcinomas and melanomas.

The inventors have recently shown that LN5 is over expressed in human colorectal adenocarcinomas (Rémy et al. 2006). They have further analyzed the expression of the LG4/5 domain in these tumors and preliminary results indicate that this fragment is also over-expressed in carcinomas cells suggesting that LN5 might remain unprocessed.

LN5 is known for its role in promoting cell migration, notably those with malignant characteristics, and may act as a ligand for invasive carcinoma cells (Hinterman et al., 2004). Neoexpression of LN5 has been associated with the proliferating activity of carcinoma cells. Moreover, this expression is often located in invasive areas of carcinomas (Lohi, 2001). In vivo observations have reported the over-expression of LN5 in budding cells, which then escape from the tumor as part of the metastatic cascade (Pyke et al., 1995). Elevated expression of LN5 in cancer is considered a poor diagnostic factor and has been related to tumor invasiveness in the cervical cancer, pancreatic carcinoma, hypopharyngeal cancer, urinary bladder urothelial cancer, small-sized lung adenocarcinoma, malignant glioma, gastric cancer, squamous cell carcinoma (SCC) of the tongue, colorectal adenoma and hepatocellular carcinoma (Tsuruta et al., 2008). The inventors have recently documented the over-expression of LN5 in human colorectal adenocarcinomas (Remy et al. 2006). They have further analyzed the expression of the LG4/5 domain these tumors in comparison with that in normal colon. The inventors found that in normal human colon, the LG4/5 domain staining was never found in basement membranes (FIG. 12) but was rather found at the intracellular level of epithelial cells located along the cryptes axis and indicative of active synthesis of pre-LN5 by these cells. As expected mature LN5 staining was found at the basement membrane of epithelial cells as a gradient of decreasing intensity from the top to the base of the crypte axis (Sordat et al., 1998). In contrast, the inventors found that in colon carcinomas (FIG. 13), LG4/5 staining often colocalized with the mature LN5 staining at both intra and extracellular levels. Expression of both antigens appeared intense in close vicinity of epithelial cells suggesting that over-expressed LN5 may remain unprocessed in carcinomas.

The inventors also biochemically analyzed the ECM of cultured colon carcinoma HT29 cells. They have found that LN5 is mainly present under its precursor form showing that these cells do not maturate the alpha3 chain in LN5 and constantly interact with the LG4/5 domain (FIG. 7). Indeed, only a small amount of cleaved LG4/5 was found in this ECM and mature LN5 was not detected. The presence of pre-LN5 in the ECM of the HT29 confluent cells was surprising as this LN5 molecular form is usually associated with dividing and migrating cells or in subconfluent cultures (Ryan et al., 1999; Décline and Rousselle, 2001). Cleavage of the LG4/5 domain has usually always happened in confluent layers of normal cells (i.e. NHK) and the LG4/5 domain has never been found in normal epithelial basement membranes (Goldfinger et al., 1999; Tungall et al., 2002). Presence of pre-LN5 in the ECM of colon carcinoma cells HT29 is most likely the consequence of a decrease or a lack of LG4/5 cleavage, a biochemical feature that potentially plays a crucial role in the malignant phenotype of these carcinoma cells.

Inventors therefore analyzed whether the carcinoma cells HT29 express the LG4/5 receptor syndecan-1. The inventors performed pull-down experiments of syndecan-1 from HT29 cell lysates and compared it with that of NHK (FIG. 8). Capture of syndecan-1 was carried out by incubating NHK or HT29 cell lysates with beads that were covalently covered with the LG4/5 fragment. Treatment of the bound HSPG-receptor with heparitinase I and chondoitinase ABC followed by immunoblotting with an antibody against syndecan-1 specifically revealed a band corresponding to the syndecan-1 core protein in both the NHK (lane 1) and the HT29 (lane 2) fractions bound to LG4/5 (FIG. 8A). The slight difference in molecular weight of syndecan-1 from HT29 is most likely the result of an increased glycosylated core protein. To verify whether the mAb 1H12 inhibited the interaction of HT29 syndecan-1 with the LG4/5 fragment, the inventors performed the pull down experiment in the presence of the function blocking antibody. As expected, 1H12 mAb, which binds to the syndecan-1 binding site in LG4/5, prevented syndecan-1 binding.

To verify that this interaction occurs in cells, the inventors analysed the distribution of pre-LN5 and syndecan-1 in cultured HT29 by confocal microscopy (optical slides of 0.8 μm were selected at the cell-matrix interface). This experiment revealed that both antigens were strongly expressed and colocalized in cells located at the edges of colonies in location where cells divide and migrate. In agreement with the hypothesis of an interaction occurring between pre-LN5 and syndecan-1 in cells, disturbed migration of the HT29 cells was observed in the presence of the 1H12 antibody, whereas untreated control HT29 cells were capable of spreading or migrating over variable distances (FIGS. 19 and 20).

In order to test whether the LG4/5 domain in pre-LN5 might play a role in the proliferation and survival of these colon carcinoma cells, the inventors tested the effect of the 1H12, 3A11 and 15G5 mAbs on the growth of a sub-confluent culture of HT29 cells (FIG. 9 and FIG. 21). Most interestingly, the 1H12 mAb not only inhibited the growth of the HT29 cells but also induced cell death after repetitive application at concentration of 25 pmole/ml (FIG. 9). The 3A11 and 15G5 mAbs were also capable of inducing cell death of the colon carcinoma cells, albeit at a higher concentration of 50 pmole/ml (FIG. 21). This effect was not limited to colon carcinoma cells, since the 1H12, 3A11 and 15G5 mAbs were all capable of inducing cell death in subconfluent cultures of breast adenocarcinoma cells MCF7 or MDA-MB231 (FIG. 22), and of ovarian adenocarcinoma NIH-OVCAR-3 cells. The effects of 1H12 on the growth of pre-LN5 expressing tumor xenografts were tested. A study using MDA-MB-231 breast tumor xenograft model is shown in FIG. 24. The growths of MDA-MB-231 tumors were inhibited by the 1H12 antibody, as evidenced by the marked delay of tumor cell growth relative to saline control. Thus, the 1H12 antibody has potent growth inhibitory activities on pre-LN5 or LG4/5 expressing tumors in vivo, confirming the in vitro results.

The above results clearly show that:

carcinoma cells preferentially express non matured pre-LN5 expressing the alpha3 LG4/5 domain, the 1H12, 3A11 and 15G5 mAbs inhibit proliferation and growth of cells expressing pre-LN5, in particular of colon carcinoma HT29 cells, breast adenocarcinoma cells MCF7 and MDA-MB231, and ovarian adenocarcinoma NIH-OVCAR-3 cells, the 1H12 mAb inhibits the growth of MDA-MB-231 tumors in xenografted mice.

These results thus demonstrate that an antibody directed to the LN5 alpha3 LG4/5 domain and specifically targeting the interaction between this domain and syndecan-1 has antitumor activity.

As a result, although the LN5 alpha3 LG4/5 domain also contains binding domains for syndecan-2 and syndecan-4, monoclonal antibodies directed to the LN5 alpha3 LG4/5 domain should target the interaction between this domain and syndecan-1 to be efficient against cancer cells.

TABLE 2

Comparison of the 1H12-VH gene with the IMGT mouse immunoglobulin data base

| Result summary: | Productive IGH rearranged sequence (no stop codon and in-frame junction) |
|---|---|
| V-GENE and allele | IGHV1-18*01, or IGHV1-22*01 score = 1222 identity = 92.28% (263/285 nt) |
| J-GENE and allele | IGHJ4*01 [a] score = 171 identity = 79.63% (43/54 nt) |
| D-GENE and allele by IMGT/JunctionAnalysis | IGHD1-1*01 D-REGION is in reading frame 1 |
| [CDR1-IMGT.CDR2-IMGT.CDR3-IMGT] lengths and AA JUNCTION | [8.8.10] CASPDLPPMDYW |

[a] Other possibilities: IGHJ1*03 (highest number of consecutive identical nucleotides)

TABLE 3

Comparison of the 1H12-VL gene with the IMGT mouse immunoglobulin data base

| Result summary: | Productive IGK rearranged sequence (no stop codon and in-frame junction) |
|---|---|
| V-GENE and allele | IGKV1-135*01 score = 1348 identity = 95.58% (281/294 nt) |
| J-GENE and allele | IGKJ2*01 score = 152 identity = 94.12% (32/34 nt) |
| [CDR1-IMGT.CDR2-IMGT.CDR3-IMGT] lengths and AA JUNCTION | [11.3.9] CWQGTHFPHTF |

TABLE 4

Comparison of the 3A11-VH gene with the IMGT mouse immunoglobulin data base

| Result summary: | Productive IGH rearranged sequence (no stop codon and in-frame junction) |
|---|---|
| V-GENE and allele | IGHV5-12*02 score = 1273 identity = 93.75% (270/288 nt) |
| J-GENE and allele | IGHJ1*01, or IGHJ1*03 score = 220 identity = 90.57% (48/53 nt) |
| D-GENE and allele by IMGT/JunctionAnalysis | IGHD2-10*01 D-REGION is in reading frame 3 |
| [CDR1-IMGT.CDR2-IMGT.CDR3-IMGT] lengths and AA JUNCTION | [8.8.14] CARPPSYGNYGYFNVW |

TABLE 5

Comparison of the 3A11-VL gene with the IMGT mouse immunoglobulin data base

| Result summary: | Productive IGK rearranged sequence (no stop codon and in-frame junction) |
|---|---|
| V-GENE and allele | IGKV3-1*01 score = 1405 identity = 98.28% (286/291 nt) |
| J-GENE and allele | IGKJ2*01 score = 190 identity = 100.00% (38/38 nt) |

TABLE 5-continued

Comparison of the 3A11-VL gene with the IMGT mouse immunoglobulin data base

| Result summary: | Productive IGK rearranged sequence (no stop codon and in-frame junction) |
|---|---|
| [CDR1-IMGT.CDR2-IMGT.CDR3-IMGT] lengths and AA JUNCTION | [10.3.9] CQQSRKVPYTF |

TABLE 6

Comparison of the 15G5-VH gene with the IMGT mouse immunoglobulin data base

| Result summary: | Productive IGH rearranged sequence (no stop codon and in-frame junction) |
|---|---|
| V-GENE and allele | IGHV1-5*01 score = 1165 identity = 92.59% (250/270 nt) |
| J-GENE and allele | IGHJ4*01 [a] score = 207 identity = 87.04% (47/54 nt) |
| D-GENE and allele by IMGT/JunctionAnalysis | IGHD2-14*01 D-REGION is in reading frame 2 |
| [CDR1-IMGT.CDR2-IMGT.CDR3-IMGT] lengths and AA JUNCTION | [8.8.14] CTRERADVYYYGMDYW |

[a] Other possibilities: IGHJ1*01 and IGHJ1*03 (highest number of consecutive identical nucleotides)

TABLE 7

Comparison of the 15G5-VL gene with the IMGT mouse immunoglobulin data base

| Result summary: | Productive IGK rearranged sequence (no stop codon and in-frame junction) |
|---|---|
| V-GENE and allele | IGKV4-57*01 score = 1285 identity = 96.38% (266/276 nt) |
| J-GENE and allele | IGKJ4*01 score = 156 identity = 96.97% (32/33 nt) |
| [CDR1-IMGT.CDR2-IMGT.CDR3-IMGT] lengths and AA JUNCTION | [5.3.9] CHQRSSYPFTF |

BIBLIOGRAPHY

Baker et al, Laminin-5 and hemidesmosomes: role of the α3 chain subunit in hemidesmosome stability and assembly. J. Cell Sci, 109, 2509-2520 (1996);

Bachy et al. Syndecan-1 interaction with the LG4/5 domain in laminin-332 is essential for keratinocyte migration. J Cell Physiol. 2008 January; 214(1):238-49.

Carter W G, Ryan M C, and Gahr P J. Epiligrin, a new cell adhesion ligand for integrin alpha 3 beta 1 in epithelial basement membranes. Cell. 1991, 65:599-610

Champliaud M. F., Lunstrum G. P., Rousselle P., Nishiyama T., Keene D. R., and Burgeson R. E. Human amnion contains a novel laminin variant, laminin 7, which like laminin 6 covalently associates with laminin 5 to promote stable epithelial-stromal attachment. J. Cell Biol., 1996, 132: 1189-1198.

Chen M, Marinkovich M P, Jones J C, O'Toole E A, Li Y Y, Woodley D T. NC1 domain of type VII collagen binds to the beta3 chain of laminin 5 via a unique subdomain within the fibronectin-like repeats. J Invest Dermatol 1999: 112: 177-183.

Decline F, and Rousselle P. 2001. Keratinocyte migration requires alpha2beta1 integrin-mediated interaction with the laminin 5 gamma2 chain. J Cell Sci 114:811-823.

Frank and Carter, Laminin 5 deposition regulates keratinocyte polarization and persistent migration. J Cell Sci. 2004 Mar. 15; 117(Pt 8):1351-63.

Franzke C W, Has C, Schulte C et al. C-terminal truncation impairs glycosylation of transmembrane collagen XVII and leads to intracellular accumulation. J Biol Chem 2006: 281: 30260-30268. 44.

Goldfinger et al., The alpha3 laminin subunit, alpha6beta4 and alpha3beta1 integrin coordinately regulate wound healing in cultured epithelial cells and in the skin. J Cell Sci. 1999 August; 112 (Pt 16):2615-29.

Gonzales et al, A cell signal pathway involving laminin-5, alpha3beta1 integrin, and mitogen-activated protein kinase can regulate epithelial cell proliferation. MBC, 10, 259-270 (1999)

Hintermann E, Quaranta V. Epithelial cell motility on laminin-5: regulation by matrix assembly, proteolysis, integrins and erbB receptors. Matrix Biol 2004; 23:75-85.

Kim et al., Epithelial cell-specific laminin 5 is required for survival of early thymocytes. J. Immunol., 165, 192-201 (2000);

Lohi J. Laminin-5 in the progression of carcinomas. Int J Cancer 2001; 94:763-7.

Miyazaki K. Laminin-5 (laminin-332): Unique biological activity and role in tumor growth and invasion. Cancer Sci, 2006, 97, 91-8.

Mizushima et al. Identification of integrin-dependent and -independent cell adhesion domains in COOH-terminal globular region of laminin-5 alpha 3 chain. Cell Growth Differ. 1997 September; 8(9):979-87.

Okamoto O, Bachy S, Odenthal U, Bernaud J, Rigal D, Lortat-Jacob H, Smyth N and Rousselle P. Normal human keratinocytes bind to the alpha3LG4/5 domain of unprocessed laminin-5 through the receptor syndecan-1. J. Biol. Chem., 2003, 278: 1-10.

Orlandi R et al., Cloning immunoglobulin variable domains for expression by the polymerase chain reaction (chimeric antibodies/MBr1). Proc. Natl. Acad. Sci. USA, Vol. 86, 3833-3837, 1989.

Paine-Murrieta G D, Taylor C W, Curtis R A, Lopez M H, Dorr R T, Johnson C S, Funk C Y, Thompson F, Hersh E M., Human tumor models in the severe combined immune deficient (scid) mouse. Cancer Chemother Pharmacol. 1997, 40:209-14.

Pyke C, Salo S, Ralfkiaer E, Romer K, Dano K, Tryggvason K. Laminin-5 is a marker of invading cancer cells in some human carcinomas and is coexpressed with to receptor for urokinase plasminogen activator in budding cancer cells in colon adenocarcinomas. Cancer Res 1995; 55:4132-9.

Rémy L et al. Matrilysin 1 influences colon carcinoma cell migration by cleavage of the laminin-5 beta3 chain. Cancer Res. 2006 Dec. 1; 66(23):11228-37.

Rousselle P and Aumailley M. Kalinin is more efficient than laminin in promoting adhesion of primary keratinocytes and some other epithelial cells and has a different requirement for integrin receptors. J. Cell Biol., 1994, 125:205-214

Rousselle P, Lunstrum G P, Keene D R and Burgeson R E. 1991. Kalinin: an epithelium-specific basement membrane adhesion molecule that is a component of anchoring filaments. J Cell Biol 114:567-576.

Rousselle P, Keene D R, Ruggiero F, Champliaud M F, van der Rest M and Burgeson R E. 1997. Laminin 5 binds the NC-1 domain of type VII collagen. J Cell Biol 138:719-728.

Ryan M C, Tizard R, VanDevanter D R and Carter W G. 1994. Cloning of the LamA3 gene encoding the alpha 3 chain of the adhesive ligand epiligrin. Expression in wound repair. J Biol Chem 269:22779-22787.

Ryan M C, Lee K, Miyashita Y and Carter W G. 1999. Targeted disruption of the LAMA3 gene in mice reveals abnormalities in survival and late stage differentiation of epithelial cells. J Cell Biol 145:1309-1323.

Sasaki T, Gohring W, Mann K et al. Short arm region of laminin-5 gamma2 chain: structure, mechanism of processing and binding to heparin and proteins. J Mol Biol 2001: 314: 751-763. J Cell Sci 1990: 3: 463-471.

Shang et al. The LG3 module of laminin-5 harbors a binding site for integrin alpha3beta1 that promotes cell adhesion, spreading, and migration. Biol. Chem. 2001 Aug. 31; 276 (35):33045-53. Epub 2001 Jun. 6.

Sordat I, Bosman F T, Dorta G., Rousselle P., Aberdam D., Blum A L., Sordat B. Differential expression of laminin-5 subunits and integrin receptors in human colorectal neoplasia. J Pathol 1998; 185:44-52.

Tran et al. Targeting a tumor-specific laminin domain critical for human carcinogenesis. Cancer Res. 2008 Apr. 15; 68(8):2885-94

Tsuruta D, Kobayashi H, Imanishi H, Sugawara K, Ishii M, Jones J C. Laminin-332-integrin interaction: a target for cancer therapy? Curr Med. Chem. 2008; 15: 1968-75.

Tunggal L, Ravaux J, Pesch M, Smola H, Krieg T, Gaill F, Sasaki T, Timpl R, Mauch, C and Aumailley M. 2002. Defective laminin 5 processing in cylindroma cells. Am J Pathol 160:459-468.

Utani et al. unique sequence of the laminin alpha 3 G domain binds to heparin and promotes cell adhesion through syndecan-2 and -4. J Biol Chem. 2001 Aug. 3; 276(31): 28779-88. Epub 2001 May 23.

Wayner et al., Epiligrin, a component of epithelial basement membranes, is an adhesive ligand for alpha 3 beta 1 positive T lymphocytes. J Cell Biol. 1993 June; 121(5):1141-52.

WO 2000/26342
WO 2005/040219,
WO 2005/052003
WO 2005/056598,
WO 2005/073254
WO2008/005828

Xia Y et al., Anchorage mediated by integrin alpha6beta4 to laminin 5 (epiligrin) regulates tyrosine phosphorylation of a membrane-associated 80-kD protein. J Cell Biol. 1996 February; 132(4):727-40

The invention claimed is:

1. A monoclonal antibody, or fragment thereof, capable of binding to the LG4/5 domain of chain alpha3 of human protein laminin-5 (SEQ ID NO:3), and inhibiting the binding of syndecan-1 to said laminin-5 alpha3 chain LG4/5 domain, wherein:

A) said monoclonal antibody, or fragment thereof, binds to the epitope of sequence: LDSKPLYTPSSSF (SEQ ID NO: 25); or B)
1) said monoclonal antibody comprises:
 a) a light chain comprising three light chain complementary regions (CDRs) having the following amino acid sequences:
  i) the light chain CDR1: QSLLDSTGRTY (SEQ ID NO:4):
  ii) the light chain CDR2: LVS;
  iii) the light chain CDR3: WQGTHFPHT (SEQ ID NO:5); and
  a light chain framework sequence from an immunoglobulin light chain; and
 b) a heavy chain comprising three heavy chain complementary regions (CDRs) having the following amino acid sequences:
  i) the heavy chain CDR1: GYTFTEYT (SEQ ID NO:6);
  ii) the heavy chain CDR2: INPKNGDT (SEQ ID NO:7);
  iii) the heavy chain CDR3: ASPDLPPMDY (SEQ ID NO:8); and
  a heavy chain framework sequence from an immunoglobulin heavy chain; or 2) said monoclonal antibody comprises :
 a) a light chain comprising three light chain complementary regions (CDRs) having the following amino acid sequences:
  i) the light chain CDR1: ESVEYYGTSL (SEQ ID NO:32):
  ii) the light chain CDR2: TAS (SEQ ID NO: 33);
  iii) the light chain CDR3: QQSRKVPYT (SEQ ID N0:34); and
  a light chain framework sequence from an immunoglobulin light chain; and
 b) a heavy chain comprising three heavy chain complementary regions (CDRs) having the following amino acid sequences:
  i) the heavy chain CDR1: GFTFSDYY (SEQ ID NO:29);
  ii) the heavy chain CDR2: ITNIGGNT (SEQ ID NO:30);
  iii) the heavy chain CDR3: ARPPSYGNYGYFNV (SEQ ID NO:31); and
  a heavy chain framework sequence from an immunoglobulin heavy chain.; or 3) said monoclonal antibody comprises: :
 a) a light chain comprising three light chain complementary regions (CDRs) having the following amino acid sequences:
  i) the light chain CDR1: SSIAH (SEQ ID NO:38);
  ii) the light chain CDR2: STS (SEQ ID NO:39);
  iii) the light chain CDR3: HQRSSYPFT (SEQ ID NO:40); and
  a light chain framework sequence from an immunoglobulin light chain; and
 b) a heavy chain comprising three heavy chain complementary regions (CDRs) having the following amino acid sequences:
  i) the heavy chain CDR1: GYSLATYW (SEQ ID NO:35);
  ii) the heavy chain CDR2: IYPGNGET (SEQ ID NO:36);
  iii) the heavy chain CDR3: TRERADVYYYGMDY (SEQ ID NO:37); and
  a heavy chain framework sequence from an immunoglobulin heavy chain.

2. The monoclonal antibody, or fragment thereof, of claim 1, wherein said monoclonal antibody is a chimerized antibody and comprises the constant regions from human immunoglobulin light and heavy chains.

3. The monoclonal antibody, or fragment thereof, of claim 1, wherein:
1) said monoclonal antibody comprises:
   i) the light chain variable region (LCVR) with the amino acid sequence DIQLTQSPLTLSVTIGQPASISCKSSQSLLDSTGRTYLNWLLQRPGQSPKRLIYLVSKLDSGVPDRFTGSGSGTDFTLKISRVEAEDLGLYYCWQGTHFPHTFGGGTKLEIK (SEQ ID NO:9); and
   ii) the heavy chain variable region (HCVR) with the amino acid sequence VKLQQSGPELVKPGASVKISCKTSGYTFTEYTIHWVKQSHGKTLEWIGGINPKNGDTSYNQKFKGKATLTVDKSSNTAYMEFRSLTSEDSAVYYCASPDLPPMDYWGQGTTVTVSS (SEQ ID NO:10); or
2) said monoclonal antibody comprises:
   i) the light chain variable region (LVCR) with the amino acid sequence DIVVIQSPASLAVSLGQRATISCRASESVEYYGTSLMQWYQQKPGQPPKLLIYTASNVESGVPARFSGSGSGTDFSLNIHPVEEDDIAMYFCQQSRKVPYTEGGGTKLEIKRADAAPTVSIFPP (SEQ ID NO: 20), and
   ii) the heavy chain variable region (HCVR) with the amino acid sequence EVQLQQSGGGLVQPGGSLKLSCATSGFTFSDYYMFWVRQTPEKRLEWVAHITNIGGNTYYPDTVKGRFTISRDNDKNTLYLQMSRLKSEDTAMYYCARPPSYGNYGYFNVWGQGTTVTVS (SEQ ID NO: 18), or
3) said monoclonal antibody comprises:
   i) the light chain variable region (LVCR) with the amino acid sequence QIVLTQSPAIMSASPGEKVSITCSASSSIHMYWFQQKPDTSPKLWIYSTSNLASGVPSRFSGSGSGTSYSLTISRMEAEDAATYYCHQRSSYPFTFGSGTKLEVKRADAAPTVSIFPP (SEQ NO: 24), and
   ii) the heavy chain variable region (HCVR) with the amino acid sequence SGTVLARPGASVRMSCKASGYSLATYWMIWVKQRPGQGLEWIGSIYPGNGETTYNQKFKDKARLTAVTSASTAYMEFSSLTIEDSAVYYCTRERADVYYYGMDYWGQGTTVTVSSKG (SEQ ID NO: 22).

4. The monoclonal antibody, or fragment thereof, of claim 1, wherein said monoclonal antibody is a humanized antibody.

5. The monoclonal antibody, or fragment thereof, of claim 4, wherein said humanized antibody comprises:
   i) the light chain variable region (LCVR) with the amino acid sequence DI(QN/E)LTQSPL(T/S)L(S/P)VT(I/L)GQPASISC(K/R)SSQSLLSTGRTYL NW(L/F)(L/Q/H)QRPGQSP(K/R)RLIYLVS(K/N/D/H)(L/R/W)DSGVPDRF( T/S)GSGSGTDFTLKISRVEAED(LN)G(L/V)YYCWQGTHFPHTEGGGTK LEIK (SEQ ID NO:11), wherein said amino acid sequence SEQ ID NO:11 differs from at least one amino acid compared to SEQ ID NO:9; and
   ii) the heavy chain variable region (HCVR) with the amino acid sequence VKLQQSGPELVKPGASVKISCK(T/AN)SGYTFTEYT(I/MN)HWVKQSH GKTLEWIG(G/D/Y/M/W/E/I)INPKNGDTSYNQKFKGKATLTVDKSSNTA YME(F/L)RSLTSEDSAVYYCASPDLPPMDYWGQGTTVTVSS (SEQ ID NO:12), wherein the amino acid sequence SEQ ID NO:12 differs from at least one amino acid compared to SEQ ID NO:10.

6. The monoclonal antibody, or fragment thereof, of claim 1 wherein said monoclonal antibody is the 1H12 monoclonal antibody produced by the hybridoma cell line named 1H12 deposited on Jan. 8, 2008 at the Collection Nationale de Cultures de Microorganismes (C.N.C.M.., INSTITUT PASTEUR, 25 rue du Docteur Roux, F-75724 PARIS Cedex 15, FRANCE) under number 1-3890, the 3A11 monoclonal antibody produced by the hybridoma cell line named 3A11 deposited on Dec. 15, 2009 at the Collection Nationale de Cultures de Microorganismes (C.N.C.M.., INSTITUT PASTEUR, 25 rue du Docteur Roux, F-75724 PARIS Cedex 15, FRANCE) under number 1-4267, or the 15G5 monoclonal antibody produced by the hybridoma cell line named 15G5 deposited on Dec. 15, 2009 at the Collection Nationale de Cultures de Microorganismes (C.N.C.M.., INSTITUT PASTEUR, 25 rue du Docteur Roux, F-75724 PARIS Cedex 15, FRANCE) under number 1-4268.

7. A hybridoma cell line selected from the group consisting of the hybridoma cell line named 1H12 deposited on Jan. 8, 2008 at the Collection Nationale de Cultures de Microorganismes (C.N.C.M.., INSTITUT PASTEUR, 25 rue du Docteur Roux, F-75724 PARIS Cedex 15, FRANCE) under number 1-3890, the hybridoma cell line named 3A11 deposited on Dec. 15, 2009 at the Collection Nationale de Cultures de Microorganismes (C.N.C.M.., INSTITUT PASTEUR, 25 rue du Docteur Roux, F-75724 PARIS Cedex 15, FRANCE) under number 1-4267, or the hybridoma cell line named 15G5 deposited on Dec. 15, 2009 at the Collection Nationale de Cultures de Microorganismes (C.N.C.M,.., INSTITUT PASTEUR, 25 rue du Docteur Roux, F-75724 PARIS Cedex 15, FRANCE) under number 1-4268.

8. A pharmaceutical composition comprising a monoclonal antibody, or fragments thereof, according to claim 1.

* * * * *

UNITED STATES PATENT AND TRADEMARK OFFICE
CERTIFICATE OF CORRECTION

PATENT NO. : 8,431,686 B2  
APPLICATION NO. : 13/140579  
DATED : April 30, 2013  
INVENTOR(S) : Patricia Rousselle and Francois Letourneur Page 1 of 1

It is certified that error appears in the above-identified patent and that said Letters Patent is hereby corrected as shown below:

In the Specifications

Column 12, Lines 33-45 please delete:

"sequence selected from the group consisting of DIQLIQS-PLTLSVTIGQPASISCKSSQSLLDSTGR-TYLNWLLQRPGQSPKRLIYLV SKLDSGVP-DRFTGSGSGTDFTLKISRVEAEDLGLYYCWQGTHFP-HTFGGGTKLE IK (SEQ ID NO: 9), DIVVIQSPASLAVS-LGQRATISCRASESVEYYGTSLMQW-YQQKPGQPPKLLYT ASNVESGVPARFSGSGSGTDF-SLNIHPVEEDDIAMYFCQQSRKVPYTFGGGTKL EIKRADAAPTVSIFPP (SEQ ID NO: 20), and QIVLTQS-PAIMSASPGEKVSITCSASSSIHMYW-FQQKPDTSPKLWIYSTSNLASG VPSRFSGSGSGTSYS-LTISRMEAEDAATYYCHQRSSYPFTFGSGTKLEVKR-ADA APTVSIFPP (SEQ NO: 24)."

and replace with:

-- sequence selected from the group consisting of DIQLTQSPLTLSVTIGQPASISCKSSQSLLDSTGRTYLNWLLQRPGQSPKRLIYLV SKLDSGVPDRFTGSGSGTDFTLKISRVEAEDLGLYYCWQGTHFPHTFGGGTKLE IK (SEQ ID NO: 9), DIVVIQSPASLAVSLGQRATISCRASESVEYYGTSLMQWYQQKPGQPPKLLIYT ASNVESGVPARFSGSGSGTDFSLNIHPVEEDDIAMYFCQQSRKVPYTFGGGTKL EIKRADAAPTVSIFPP (SEQ ID NO: 20), and QIVLTQSPAIMSASPGEKVSITCSASSSIHMYWFQQKPDTSPKLWIYSTSNLASG VPSRFSGSGSGTSYSLTISRMEAEDAATYYCHQRSSYPFTFGSGTKLEVKRADA APTVSIFPP (SEQ NO: 24).--

Signed and Sealed this  
Twenty-fifth Day of March, 2014

Michelle K. Lee  
*Deputy Director of the United States Patent and Trademark Office*